United States Patent
Chamness et al.

(10) Patent No.: US 11,622,887 B2
(45) Date of Patent: *Apr. 11, 2023

(54) DEVICES AND METHODS FOR OCULAR SURGERY

(71) Applicant: Carl Zeiss Meditec Cataract Technology Inc., Reno, NV (US)

(72) Inventors: Scott Chamness, Reno, NV (US); Luke W. Clauson, Reno, NV (US); Brendan Reese, Reno, NV (US); Michael P. Schaller, Reno, NV (US)

(73) Assignee: Carl Zeiss Meditec Cataract Technology Inc., Reno, NV (US)

( * ) Notice: Subject to any disclaimer, the term of this patent is extended or adjusted under 35 U.S.C. 154(b) by 867 days.

This patent is subject to a terminal disclaimer.

(21) Appl. No.: 16/436,648

(22) Filed: Jun. 10, 2019

(65) Prior Publication Data

US 2019/0321223 A1  Oct. 24, 2019

Related U.S. Application Data

(63) Continuation of application No. 15/970,439, filed on May 3, 2018, now Pat. No. 11,278,450.
(Continued)

(51) Int. Cl.
*A61F 9/007* (2006.01)
*A61B 17/22* (2006.01)
(Continued)

(52) U.S. Cl.
CPC ........ *A61F 9/00763* (2013.01); *A61B 17/221* (2013.01); *A61B 17/22031* (2013.01);
(Continued)

(58) Field of Classification Search
CPC .............. A61F 9/00763; A61F 9/00754; A61F 2009/00887; A61B 17/22031; A61B 17/221; A61B 17/320758
See application file for complete search history.

(56) References Cited

U.S. PATENT DOCUMENTS 1,833,687 A   11/1931   Neivert
2,947,470 A    8/1960   Ruben et al.
(Continued)

FOREIGN PATENT DOCUMENTS

DE   10 2007 031722 A1   1/2009
DE      102007040290 B4   7/2019
(Continued)

OTHER PUBLICATIONS

U.S. Appl. No. 15/970,439, filed May 3, 2018, US 2018-0318132.
(Continued)

*Primary Examiner* — Diane D Yabut
*Assistant Examiner* — Christina C Lauer
(74) *Attorney, Agent, or Firm* — Mintz Levin Cohn Ferris Glovsky and Popeo, P.C.

(57) ABSTRACT

Devices, systems, and methods for performing an ophthalmic procedure in an eye are disclosed. The devices include a hand-held portion and a distal, elongate member coupled to the hand-held portion having a lumen operatively coupled to a vacuum source. A drive mechanism operatively coupled to the elongate member is configured to oscillate the elongate member. When in use, the device is configured to aspirate ocular material from the eye through the lumen. The drive mechanism retracts the elongate member with a retraction speed profile and advances the elongate member with an extension speed profile. The retraction speed profile is different from the extension speed profile.

19 Claims, 53 Drawing Sheets

Related U.S. Application Data

(60) Provisional application No. 62/597,826, filed on Dec. 12, 2017, provisional application No. 62/501,710, filed on May 4, 2017.

(51) Int. Cl.
*A61B 17/221* (2006.01)
*A61F 9/008* (2006.01)
*A61B 17/3205* (2006.01)
*A61B 17/32* (2006.01)
*A61B 17/30* (2006.01)

(52) U.S. Cl.
CPC .... *A61F 9/00754* (2013.01); *A61B 17/32056* (2013.01); *A61B 2017/306* (2013.01); *A61B 2017/32006* (2013.01); *A61B 2017/320024* (2013.01); *A61B 2217/005* (2013.01); *A61F 2009/00887* (2013.01)

(56) References Cited

U.S. PATENT DOCUMENTS

| | | |
|---|---|---|
| 3,183,849 A | 5/1965 | Raymond |
| 3,589,363 A | 6/1971 | Banko et al. |
| 3,957,052 A | 5/1976 | Topham |
| 3,990,452 A | 11/1976 | Murry et al. |
| 4,368,734 A | 1/1983 | Banko |
| 4,493,706 A | 1/1985 | Borsanyi et al. |
| 4,508,532 A | 4/1985 | Drews et al. |
| 4,643,187 A | 2/1987 | Okada |
| 4,705,500 A | 11/1987 | Reimels et al. |
| 4,732,150 A | 3/1988 | Keener, Jr. |
| 4,764,165 A | 8/1988 | Reimels et al. |
| 4,854,825 A | 8/1989 | Bez et al. |
| 4,869,716 A | 9/1989 | Smirmaul |
| 4,891,044 A | 1/1990 | Mitchell |
| 4,908,015 A | 3/1990 | Anis |
| 4,921,477 A | 5/1990 | Davis |
| 5,146,921 A | 9/1992 | Terwilliger et al. |
| 5,222,959 A | 6/1993 | Anis |
| 5,275,607 A | 1/1994 | Lo et al. |
| 5,279,547 A | 1/1994 | Costin |
| 5,337,780 A | 8/1994 | Kee et al. |
| 5,350,390 A | 9/1994 | Sher |
| 5,437,678 A | 8/1995 | Sorensen |
| 5,651,783 A | 7/1997 | Reynard |
| 5,676,649 A | 10/1997 | Boukhny et al. |
| 5,693,062 A | 12/1997 | Stegmann et al. |
| 5,788,667 A | 8/1998 | Stoller et al. |
| 5,788,679 A | 8/1998 | Gravlee, Jr. |
| 5,807,401 A | 9/1998 | Grieshaber et al. |
| 5,843,071 A | 12/1998 | Bath |
| 5,891,153 A | 4/1999 | Peterson |
| 5,911,699 A | 6/1999 | Anis et al. |
| 5,938,677 A | 8/1999 | Boukhny et al. |
| 6,004,284 A | 12/1999 | Sussman et al. |
| 6,013,049 A | 1/2000 | Rockley et al. |
| 6,059,765 A | 5/2000 | Cole et al. |
| 6,074,396 A | 6/2000 | Geuder |
| 6,117,149 A | 9/2000 | Sorensen et al. |
| 6,132,436 A | 10/2000 | Portney |
| 6,165,190 A | 12/2000 | Nguyen |
| 6,183,433 B1 | 2/2001 | Bays |
| 6,186,148 B1 | 2/2001 | Okada |
| 6,241,700 B1 | 6/2001 | Leukanech |
| 6,254,587 B1 | 7/2001 | Christ et al. |
| 6,299,591 B1 | 10/2001 | Banko |
| 6,319,222 B1 | 11/2001 | Andrew et al. |
| 6,322,557 B1 | 11/2001 | Nikolaevich et al. |
| 6,328,747 B1 | 12/2001 | Nun |
| 6,398,754 B1 | 6/2002 | Sutton et al. |
| 6,428,508 B1 | 8/2002 | Ross |
| 6,485,499 B1 | 11/2002 | Oberkamp et al. |
| 6,506,176 B1 | 1/2003 | Mittelstein et al. |
| 6,520,929 B2 | 2/2003 | Zaleski |
| 6,520,955 B2 | 2/2003 | Reynard |
| 6,527,766 B1 | 3/2003 | Bair |
| 6,544,254 B1 | 4/2003 | Bath |
| 6,589,201 B1 | 7/2003 | Sussman et al. |
| 6,592,541 B1 | 7/2003 | Kurwa |
| 6,605,054 B2 | 8/2003 | Rockley |
| 6,623,477 B1 | 9/2003 | Elbrecht et al. |
| 6,852,092 B2 | 2/2005 | Kadziauskas et al. |
| 6,860,868 B1 | 3/2005 | Sussman et al. |
| 6,939,317 B2 | 9/2005 | Zacharias |
| 6,939,341 B2 | 9/2005 | Vijfvinkel |
| 7,041,078 B1 | 5/2006 | Peyman |
| 7,083,589 B2 | 8/2006 | Banko et al. |
| 7,141,047 B2 | 11/2006 | John |
| 7,172,601 B2 | 2/2007 | Ben-Nun |
| 7,182,759 B2 | 2/2007 | Kadziauskas et al. |
| 7,204,820 B2 | 4/2007 | Akahoshi |
| 7,285,107 B1 | 10/2007 | Charles |
| 7,303,566 B2 | 12/2007 | Kishimoto et al. |
| 7,544,178 B2 | 6/2009 | Kadziauskas et al. |
| 7,549,972 B2 | 6/2009 | Luloh et al. |
| 7,588,553 B2 | 9/2009 | Dewey |
| 7,845,235 B2 | 12/2010 | Sandu et al. |
| 7,846,126 B2 | 12/2010 | Steen et al. |
| 7,857,794 B2 | 12/2010 | Dimalanta et al. |
| 7,876,025 B2 | 1/2011 | Ma et al. |
| 7,955,060 B2 | 6/2011 | Gottschalk |
| 7,967,775 B2 | 6/2011 | Hong |
| 8,070,711 B2 | 12/2011 | Bassinger et al. |
| 8,080,029 B2 | 12/2011 | Charles |
| 8,142,388 B2 | 3/2012 | Gomez |
| 8,187,293 B2 | 5/2012 | Kirchhevel |
| 8,216,246 B2 | 7/2012 | Luloh et al. |
| 8,246,644 B2 | 8/2012 | Rockley et al. |
| 8,287,484 B2 | 10/2012 | Rockley |
| 8,298,253 B2 | 10/2012 | Charles |
| 8,308,735 B2 | 11/2012 | Dimalanta |
| 8,317,739 B2 | 11/2012 | Kuebler |
| 8,376,983 B2 | 2/2013 | Ross et al. |
| 8,423,126 B2 | 4/2013 | Mackool |
| 8,475,480 B2 | 7/2013 | Mackool |
| 8,545,462 B2 | 10/2013 | Ghannoum |
| 8,771,301 B2 | 7/2014 | Boukhny et al. |
| 8,784,361 B2 | 7/2014 | Lane |
| 8,801,653 B2 | 8/2014 | Maaskamp et al. |
| 8,852,139 B2 | 10/2014 | King et al. |
| 8,876,745 B2 | 11/2014 | Escaf |
| 8,876,747 B2 | 11/2014 | Kadziauskas et al. |
| 8,939,927 B2 | 1/2015 | Sorensen et al. |
| 8,986,290 B2 | 3/2015 | Patton |
| 9,050,171 B2 | 6/2015 | Foster |
| 9,144,517 B2 | 9/2015 | Kuebler et al. |
| 9,259,597 B2 | 2/2016 | Romano et al. |
| 9,351,871 B2 | 5/2016 | Ghannoum et al. |
| 9,370,611 B2 | 6/2016 | Ross et al. |
| 9,387,122 B2 | 7/2016 | Mackool |
| 9,402,766 B2 | 8/2016 | Akahoshi et al. |
| 9,433,725 B2 | 9/2016 | Schaller et al. |
| 9,439,807 B2 | 9/2016 | Koplin |
| 9,445,943 B2 | 9/2016 | Wilson et al. |
| 9,486,359 B2 | 11/2016 | Hauger et al. |
| 9,486,360 B2 | 11/2016 | Chon |
| 9,498,377 B2 | 11/2016 | McCary et al. |
| 9,498,378 B2 | 11/2016 | McDonell |
| 9,504,604 B2 | 11/2016 | Alvarez |
| 9,561,129 B2 | 2/2017 | Ross et al. |
| 9,566,188 B2 | 2/2017 | Raney et al. |
| 9,592,156 B2 | 3/2017 | Huang |
| 9,629,747 B2 | 4/2017 | Clauson et al. |
| 9,693,896 B2 | 7/2017 | Sussman |
| 9,724,238 B2 | 8/2017 | Heitel |
| 9,731,065 B2 | 8/2017 | Bourne et al. |
| 9,750,639 B2 | 9/2017 | Barnes et al. |
| 9,775,743 B2 | 10/2017 | Clauson et al. |
| 9,827,142 B2 | 11/2017 | Sasazaki et al. |
| 9,839,738 B2 | 12/2017 | Beauvais et al. |
| 9,861,522 B2 | 1/2018 | Sorensen et al. |
| 9,867,635 B2 | 1/2018 | Alvarez et al. |
| 9,878,075 B2 | 1/2018 | Sussman et al. |

(56) References Cited

U.S. PATENT DOCUMENTS

| | | |
|---|---|---|
| 9,889,247 B2 | 2/2018 | Akahoshi |
| 9,913,752 B2 | 3/2018 | Hauger |
| 10,231,870 B2 | 3/2019 | Clauson et al. |
| 10,251,782 B2 | 4/2019 | Farley |
| 10,278,861 B2 | 5/2019 | Bourne |
| 10,294,934 B2 | 5/2019 | Bourne et al. |
| 10,603,213 B2 * | 3/2020 | Clauson ............. A61F 9/00763 |
| 11,278,450 B2 * | 3/2022 | Clauson ............. A61F 9/00763 |
| 2002/0052617 A1 | 5/2002 | Anis et al. |
| 2002/0099400 A1 | 7/2002 | Wolf et al. |
| 2002/0151835 A1 | 10/2002 | Ross |
| 2003/0004455 A1 | 1/2003 | Kadziauskas et al. |
| 2003/0055387 A1 | 3/2003 | Sutton et al. |
| 2003/0109867 A1 | 6/2003 | Gluche et al. |
| 2004/0010284 A1 | 1/2004 | Maloof et al. |
| 2004/0049217 A1 | 3/2004 | Ross et al. |
| 2004/0082902 A1 | 4/2004 | Kadziauskas et al. |
| 2004/0092800 A1 | 5/2004 | MacKool |
| 2004/0153093 A1 | 8/2004 | Donovan |
| 2005/0113741 A1 | 5/2005 | Huang et al. |
| 2005/0234441 A1 | 10/2005 | Bisch et al. |
| 2005/0234473 A1 | 10/2005 | Zacharias |
| 2006/0135974 A1 | 6/2006 | Perkins |
| 2006/0253056 A1 | 11/2006 | Kadziauskas et al. |
| 2007/0060926 A1 | 3/2007 | Escaf |
| 2007/0260173 A1 | 11/2007 | Boukhny et al. |
| 2008/0188792 A1 | 8/2008 | Barrett |
| 2008/0300531 A1 | 12/2008 | Gills, Jr. |
| 2009/0048607 A1 | 2/2009 | Rockley |
| 2009/0054904 A1 | 2/2009 | Holmen |
| 2009/0137993 A1 | 5/2009 | Kurtz |
| 2009/0149840 A1 | 6/2009 | Kurtz |
| 2009/0156985 A1 | 6/2009 | Hottmann et al. |
| 2009/0171242 A1 | 7/2009 | Hibner |
| 2010/0030134 A1 | 2/2010 | Fitzgerald et al. |
| 2010/0191178 A1 | 7/2010 | Ross et al. |
| 2010/0286651 A1 | 11/2010 | Sorensen |
| 2010/0292631 A1 | 11/2010 | Holden |
| 2010/0312170 A1 | 12/2010 | Maaskamp et al. |
| 2010/0331911 A1 | 12/2010 | Kovalcheck et al. |
| 2011/0015562 A1 | 1/2011 | Akahoshi |
| 2011/0054384 A1 | 3/2011 | Brown |
| 2011/0112466 A1 | 5/2011 | Dimalanta |
| 2011/0137231 A1 | 6/2011 | Sorensen et al. |
| 2011/0144638 A1 | 6/2011 | Heeren et al. |
| 2011/0290854 A1 | 12/2011 | Timm et al. |
| 2011/0295192 A1 | 12/2011 | Geuder |
| 2012/0004595 A1 | 1/2012 | Dubois et al. |
| 2012/0022434 A1 | 1/2012 | Lue et al. |
| 2012/0041358 A1 | 2/2012 | Mann et al. |
| 2012/0072197 A1 | 3/2012 | Ovchinnikov |
| 2012/0078181 A1 | 3/2012 | Smith et al. |
| 2012/0089080 A1 | 4/2012 | Ross et al. |
| 2012/0157908 A1 | 6/2012 | Underwood et al. |
| 2012/0158030 A1 | 6/2012 | Underwood et al. |
| 2012/0158130 A1 | 6/2012 | Moradian et al. |
| 2012/0184892 A1 | 7/2012 | Bigler et al. |
| 2012/0259320 A1 | 10/2012 | Loesel et al. |
| 2013/0060210 A1 | 3/2013 | Ross et al. |
| 2013/0231605 A1 | 9/2013 | Walter |
| 2013/0282020 A1 | 10/2013 | Hunter |
| 2014/0005681 A1 | 1/2014 | Gee et al. |
| 2014/0012186 A1 | 1/2014 | Thyzel |
| 2014/0052113 A1 | 2/2014 | Kuehnert et al. |
| 2014/0074013 A1 | 3/2014 | McCary et al. |
| 2014/0081151 A1 | 3/2014 | Saimovici |
| 2014/0081266 A1 | 3/2014 | Dubois et al. |
| 2014/0114335 A1 | 4/2014 | Banko |
| 2014/0163455 A1 | 6/2014 | Wilson et al. |
| 2014/0194860 A1 | 7/2014 | Dick et al. |
| 2014/0236163 A1 | 8/2014 | Olson et al. |
| 2014/0257258 A1 | 9/2014 | Kurtz |
| 2014/0271251 A1 | 9/2014 | Bourne et al. |
| 2014/0309649 A1 | 10/2014 | Alvarez et al. |
| 2014/0358155 A1 | 12/2014 | DeBoer et al. |
| 2014/0360494 A1 | 12/2014 | Herskovic |
| 2014/0364885 A1 | 12/2014 | Wells et al. |
| 2015/0005753 A1 | 1/2015 | Walter |
| 2015/0025450 A1 | 1/2015 | King et al. |
| 2015/0038894 A1 | 2/2015 | Urich et al. |
| 2015/0045806 A1 | 2/2015 | Urich et al. |
| 2015/0105791 A1 | 4/2015 | Truckai |
| 2015/0125328 A1 | 5/2015 | Bourne et al. |
| 2015/0141801 A1 | 5/2015 | Jean et al. |
| 2015/0144514 A1 | 5/2015 | Brennan et al. |
| 2015/0148615 A1 | 5/2015 | Brennan et al. |
| 2015/0196426 A1 | 7/2015 | Kuebler et al. |
| 2015/0202081 A1 | 7/2015 | Eichler |
| 2015/0216728 A1 | 8/2015 | Keller |
| 2015/0257927 A1 | 9/2015 | Olson |
| 2015/0297407 A1 | 10/2015 | Saimovici |
| 2015/0306286 A1 | 10/2015 | Ross et al. |
| 2015/0328047 A1 | 11/2015 | Falck, Jr. |
| 2015/0359672 A1 | 12/2015 | Van Valen et al. |
| 2016/0022489 A1 | 1/2016 | Hartstra |
| 2016/0058614 A1 | 3/2016 | Ross et al. |
| 2016/0067091 A1 | 3/2016 | Wells et al. |
| 2016/0089268 A1 | 3/2016 | Chon et al. |
| 2016/0095749 A1 | 4/2016 | Raney et al. |
| 2016/0095750 A1 | 4/2016 | Raney et al. |
| 2016/0106580 A1 | 4/2016 | Banko |
| 2016/0106893 A1 | 4/2016 | Zacharias |
| 2016/0128869 A1 | 5/2016 | Zacharias |
| 2016/0135991 A1 | 5/2016 | Farley et al. |
| 2016/0143780 A1 | 5/2016 | Gunn |
| 2016/0166432 A1 | 6/2016 | Kahook et al. |
| 2016/0175578 A1 | 6/2016 | Roholt |
| 2016/0220807 A1 | 8/2016 | Bono |
| 2017/0007451 A1 | 1/2017 | Depenbusch |
| 2017/0007452 A1 | 1/2017 | Depenbusch |
| 2017/0020728 A1 | 1/2017 | McDonell |
| 2017/0027750 A1 | 2/2017 | Wiley |
| 2017/0087013 A1 | 3/2017 | Prats et al. |
| 2017/0151091 A1 | 6/2017 | Bourne et al. |
| 2017/0151378 A1 | 6/2017 | Raney et al. |
| 2017/0312125 A1 | 11/2017 | Clauson et al. |
| 2017/0333252 A1 | 11/2017 | Biancalana et al. |
| 2017/0360607 A1 | 12/2017 | Price et al. |
| 2017/0367885 A1 | 12/2017 | Bourne |
| 2018/0028360 A1 | 2/2018 | Kozawa |
| 2018/0036171 A1 | 2/2018 | Clauson et al. |
| 2018/0049920 A1 | 2/2018 | Charles |
| 2018/0058438 A1 | 3/2018 | Ochoa |
| 2018/0064578 A1 | 3/2018 | Clauson et al. |
| 2018/0318133 A1 | 11/2018 | Clauson et al. |
| 2019/0015252 A1 | 1/2019 | Lake et al. |
| 2019/0041665 A1 | 2/2019 | Widman et al. |
| 2019/0099292 A1 | 4/2019 | Strayer et al. |
| 2019/0133825 A1 | 5/2019 | Clauson et al. |
| 2019/0151149 A1 | 5/2019 | Clauson et al. |
| 2019/0183679 A1 | 6/2019 | Sawicz |
| 2019/0183681 A1 | 6/2019 | Schaller et al. |
| 2019/0254872 A1 | 8/2019 | Clauson et al. |
| 2019/0269557 A1 | 9/2019 | Clauson et al. |
| 2019/0282402 A1 | 9/2019 | Clauson et al. |
| 2019/0365567 A1 | 12/2019 | Balkenbush et al. |
| 2019/0388272 A1 | 12/2019 | Clauson et al. |
| 2020/0016001 A1 | 1/2020 | McDonell et al. |
| 2020/0022841 A1 | 1/2020 | Chamness et al. |
| 2020/0060875 A1 | 2/2020 | Clauson et al. |
| 2020/0197222 A1 | 6/2020 | Clauson et al. |
| 2020/0306083 A1 | 10/2020 | Clauson et al. |

FOREIGN PATENT DOCUMENTS

| | | |
|---|---|---|
| EP | 1832259 B1 | 6/2009 |
| EP | 1556099 B1 | 7/2013 |
| EP | 2 168 540 B1 | 4/2015 |
| EP | 2 094 173 B1 | 3/2016 |
| EP | 1735030 B1 | 8/2016 |
| EP | 2 892 438 B1 | 10/2018 |
| GB | 1304324 A | 1/1973 |
| GB | 2018601 A | 10/1979 |
| JP | H0779826 B2 | 8/1995 |

(56) References Cited

FOREIGN PATENT DOCUMENTS

| JP | 6654763 B2 | 2/2020 |
|---|---|---|
| WO | WO-2006/119557 A1 | 11/2006 |
| WO | WO-2013/039742 A2 | 3/2013 |
| WO | WO-2014/039093 A1 | 3/2014 |
| WO | WO-2015/161149 A1 | 10/2015 |
| WO | WO-2018/081295 A1 | 5/2018 |
| WO | WO-2018/217579 A1 | 11/2018 |

OTHER PUBLICATIONS

U.S. Appl. No. 16/221,239, filed Dec. 14, 2018, US 2019-0183681.
U.S. Appl. No. 16/257,533, filed Jan. 25, 2019, US 2019-0151149.
U.S. Appl. No. 16/345,182, filed Apr. 25, 2019, US 2019-0282402.
U.S. Appl. No. 16/404,252, filed May 6, 2019, US 2019-0254872.
U.S. Appl. No. 16/778,755, filed Jan. 31, 2020, US 2020-0289319.
PCT/US2020/16155, Jan. 31, 2020, WO 2020/160434.
PCT/US/2020/33141, May 15, 2020, WO 2020/236593.
PCT/US/2020/33142, May 15, 2020, WO 2020/247165.
U.S. Appl. No. 14/894,299, filed Nov. 25, 2015, US 2016-0166432.
U.S. Appl. No. 15/418,764, filed Jan. 29, 2017, US 2018-0064578.
U.S. Appl. No. 15/460,256, filed Mar. 16, 2017, US 2017-0312125.
U.S. Appl. No. 15/688,024, filed Aug. 28, 2017, US 2018-0036171.
U.S. Appl. No. 16/240,186, filed Jan. 4, 2019, US 2019-0133825.
U.S. Appl. No. 16/415,986, filed May 17, 2019, US 2019-0269557.
PCT/US2018/030964, May 3, 2018, WO 2018/204699.
PCT/US2018/033464, May 18, 2018, WO 2018/217579.
PCT/US2018/65800, Dec. 14, 2018, WO 2019/118901.
U.S. Appl. No. 16/404,262, filed May 6, 2019, US 2019-0254872.
U.S. Appl. No. 16/431,560, filed Jun. 4, 2019, US 2019-0365567.
U.S. Appl. No. 16/577,418, filed Sep. 20, 2019, US 2020-0022841.
U.S. Appl. No. 16/667,030, filed Oct. 29, 2019, US 2020-0060875.
U.S. Appl. No. 16/690,881, filed Nov. 21, 2019, US 2020-0197222.
U.S. Appl. No. 16/811,786, filed Mar. 6, 2020, US 2020-0306083.
U.S. Appl. No. 16/875,421, filed May 15, 2020, US 2020-0383833.
U.S. Appl. No. 16/875,426, filed May 15, 2020, US 2020-0360185.
U.S. Appl. No. 17/177,017, filed Feb. 16, 2021, US 2021-0161712.
U.S. Appl. No. 17/570,094, filed Jan. 6, 2022, US 2022-0233353.
Vibration, First recorded in 1645-1655, Dictionary.com (Year: 1645). 5 pages.

* cited by examiner

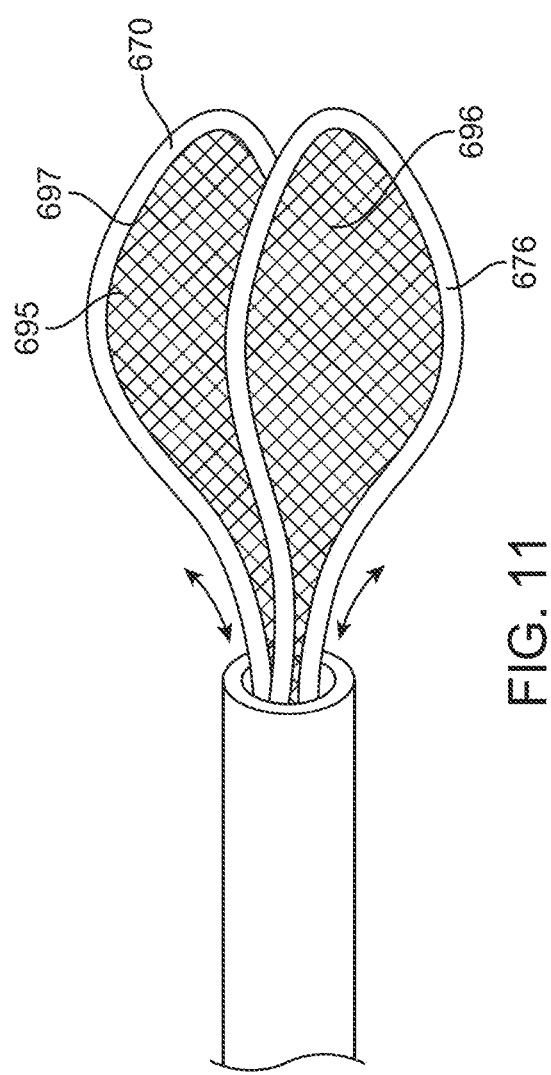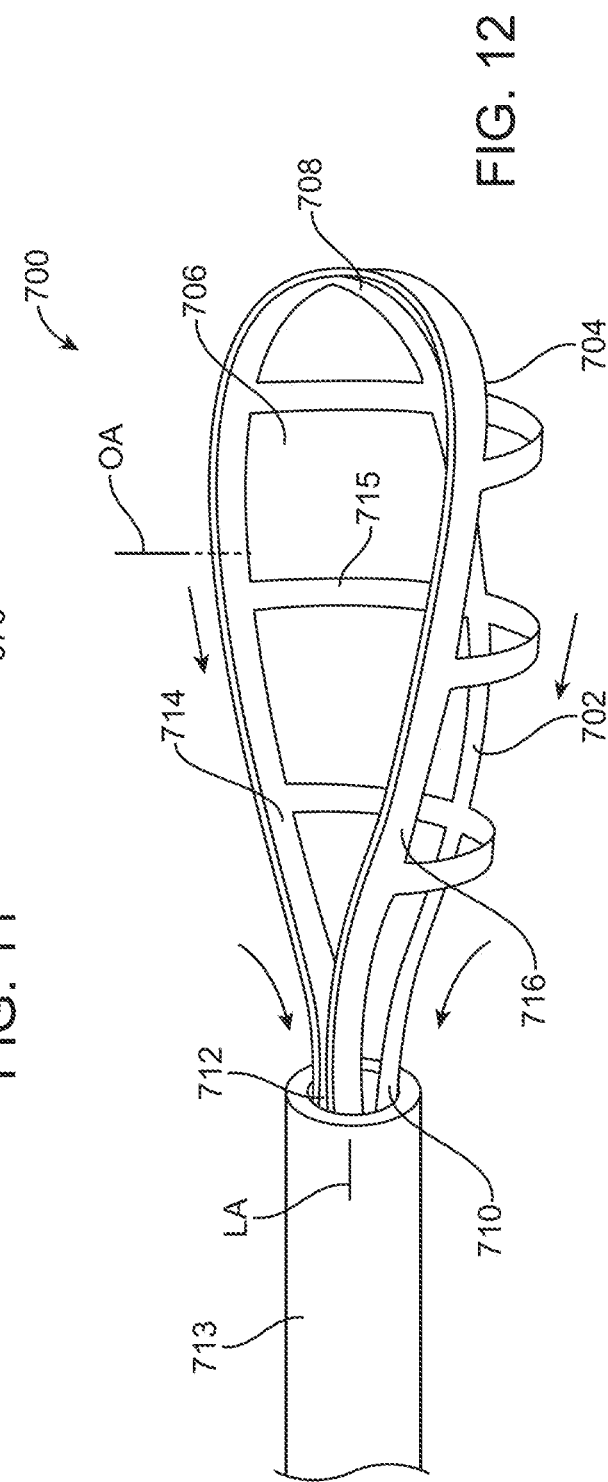

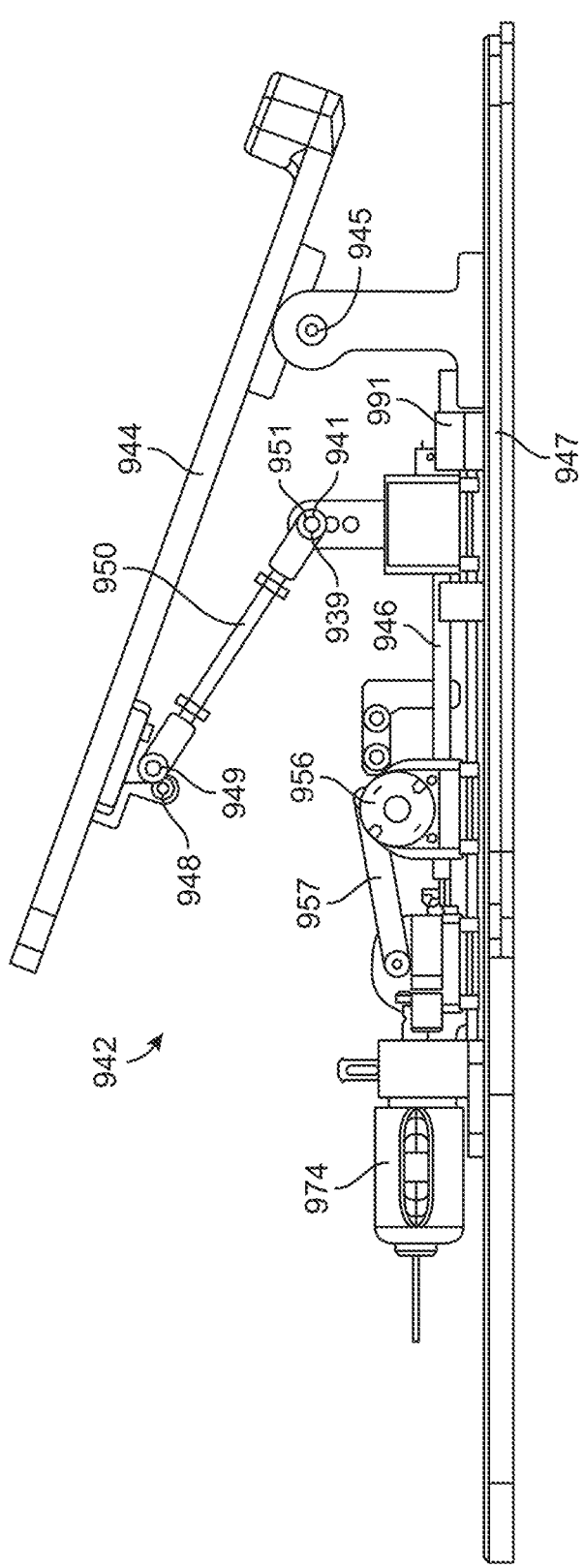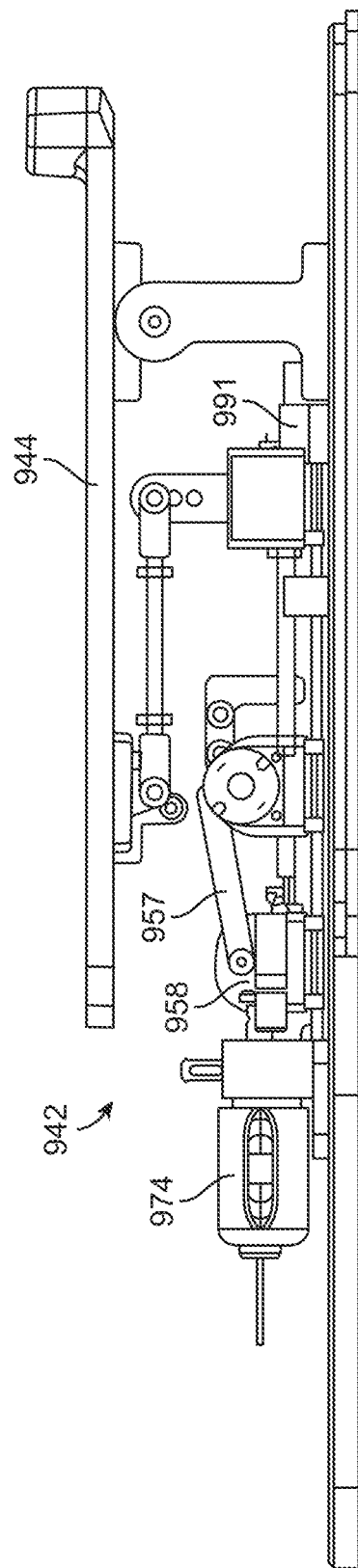

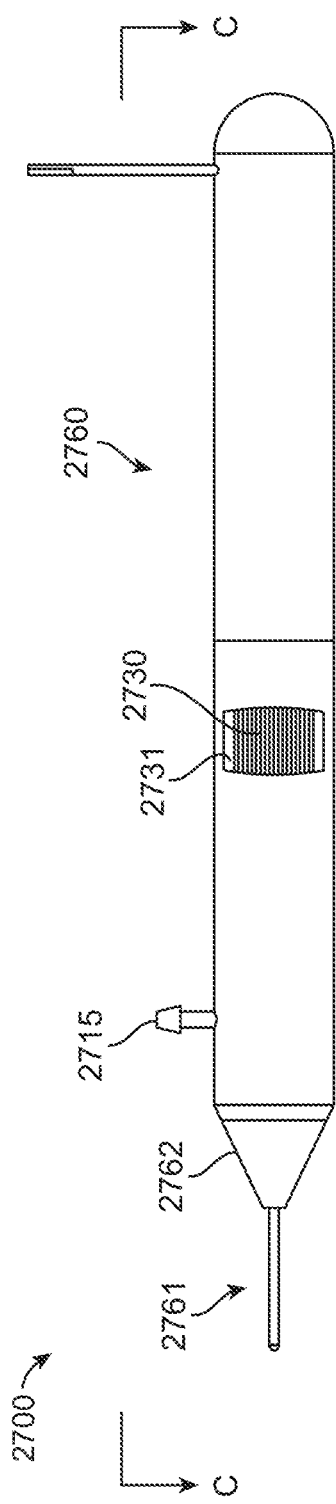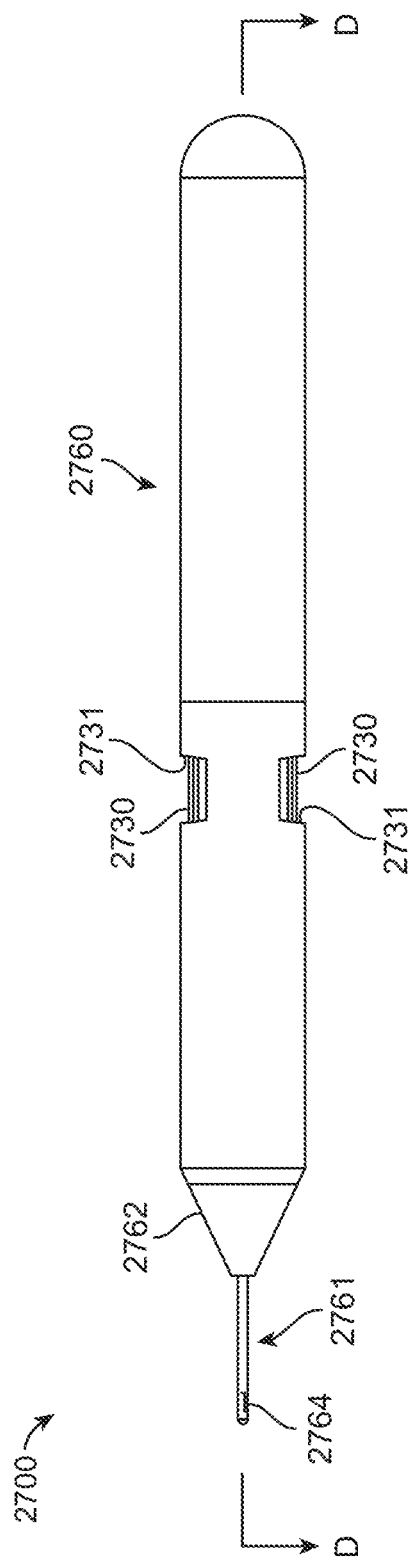

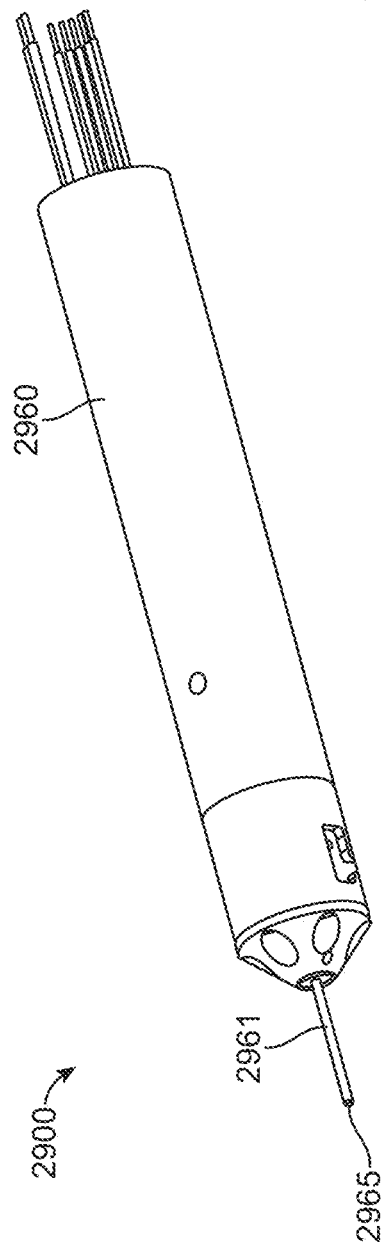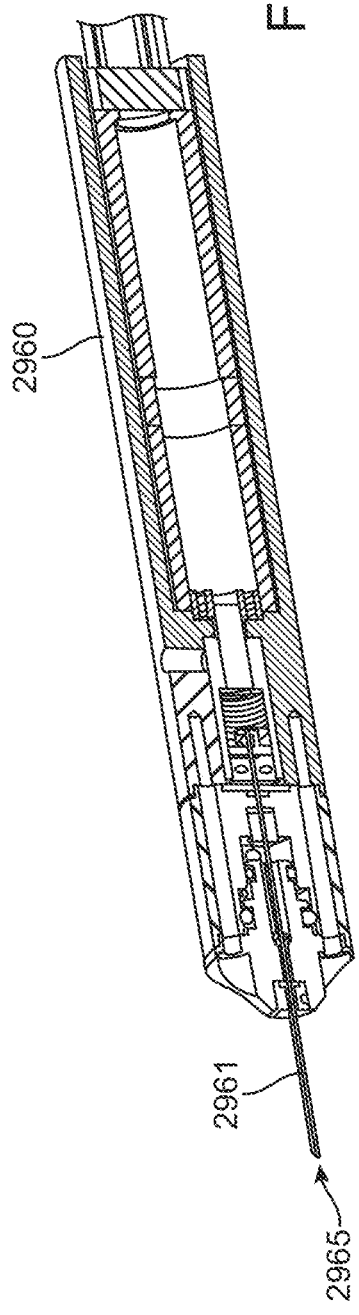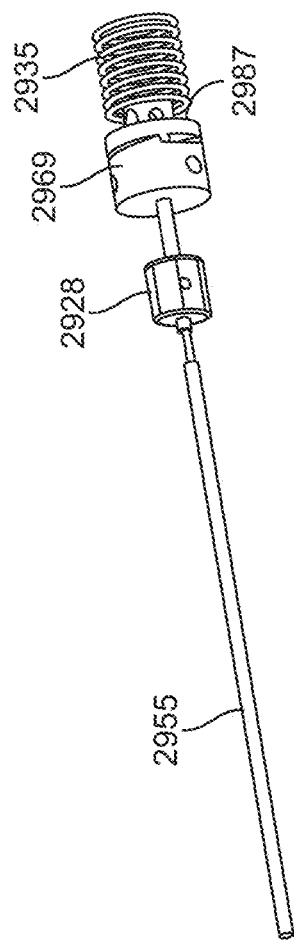

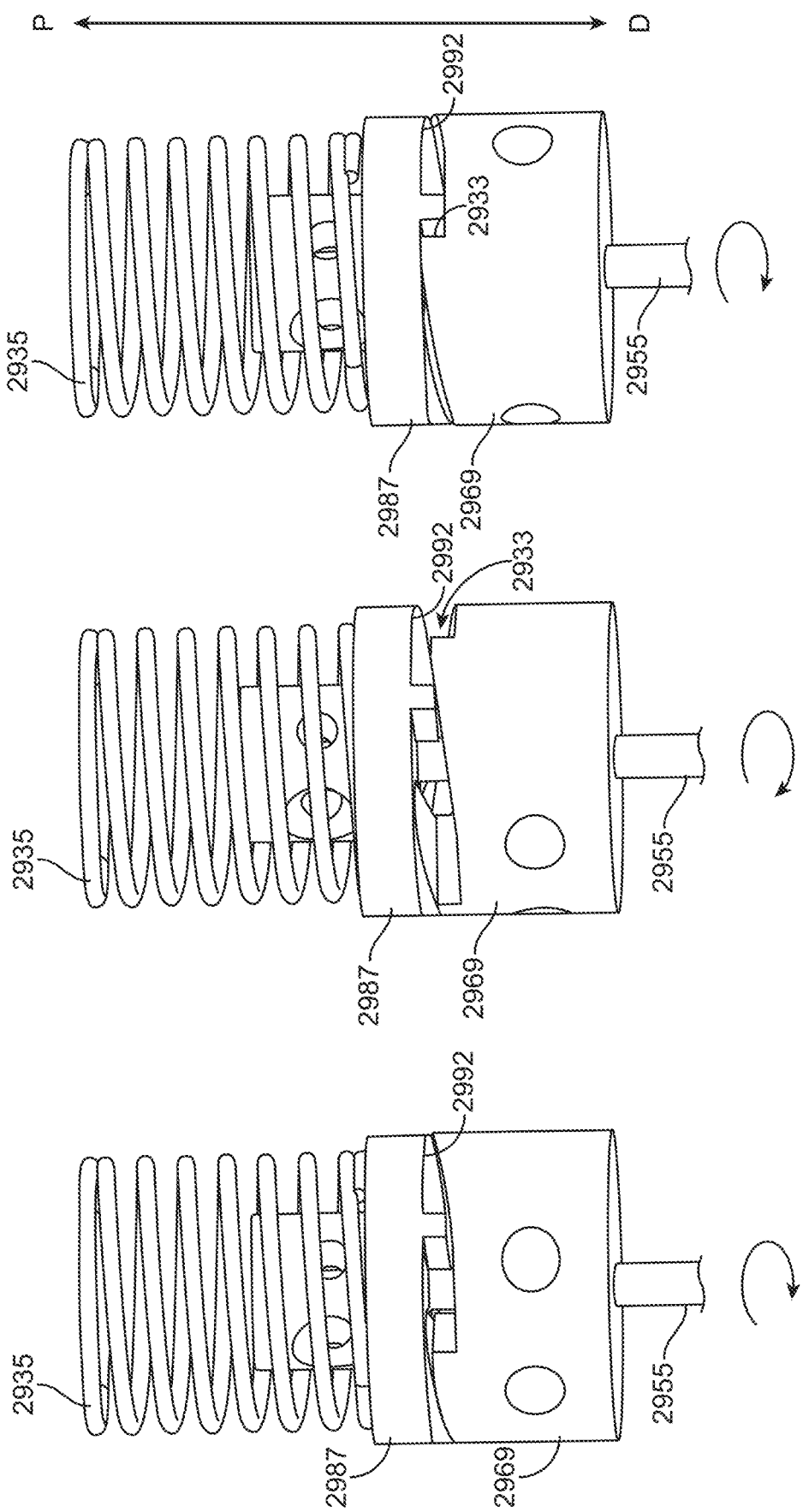

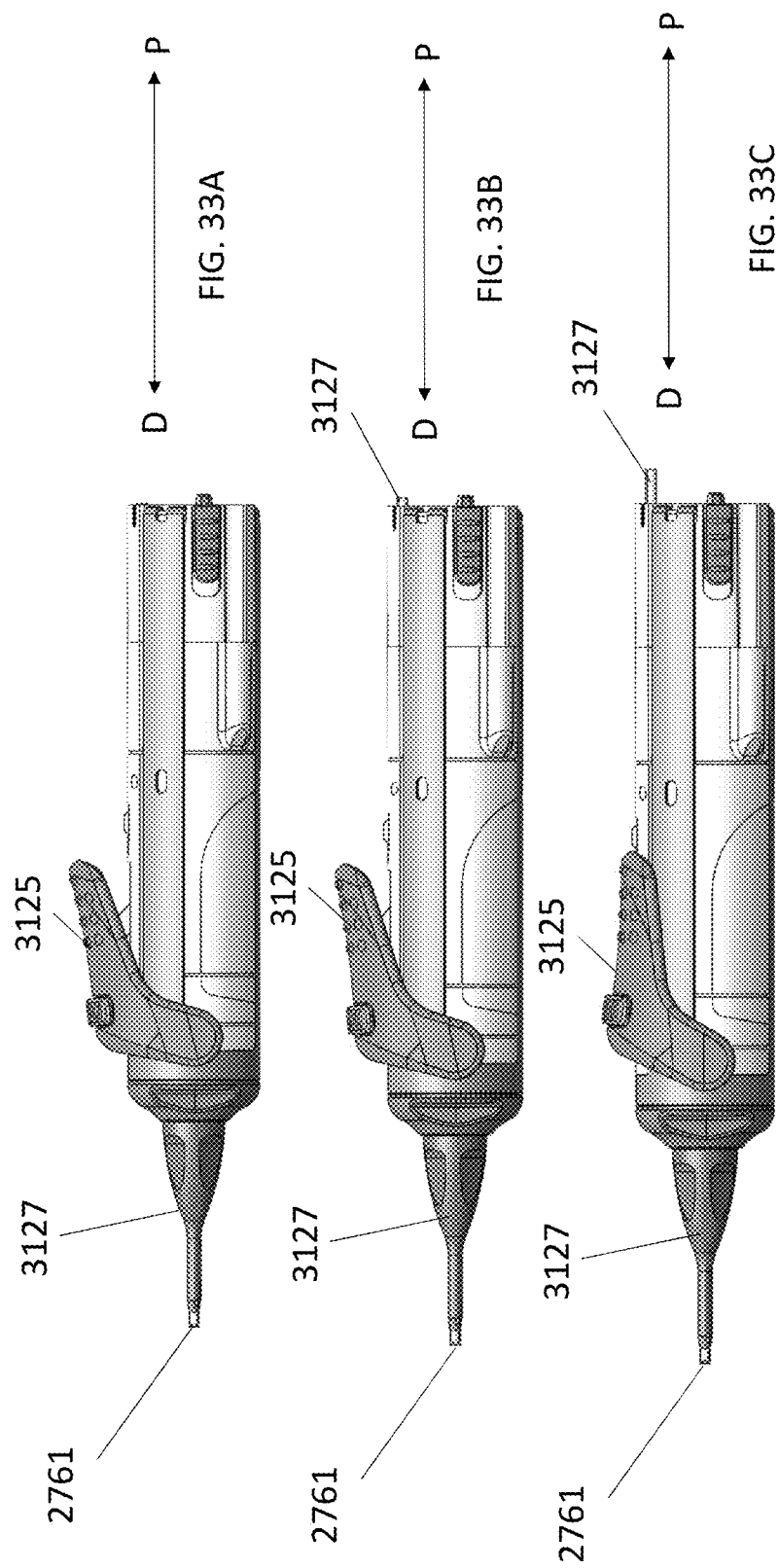

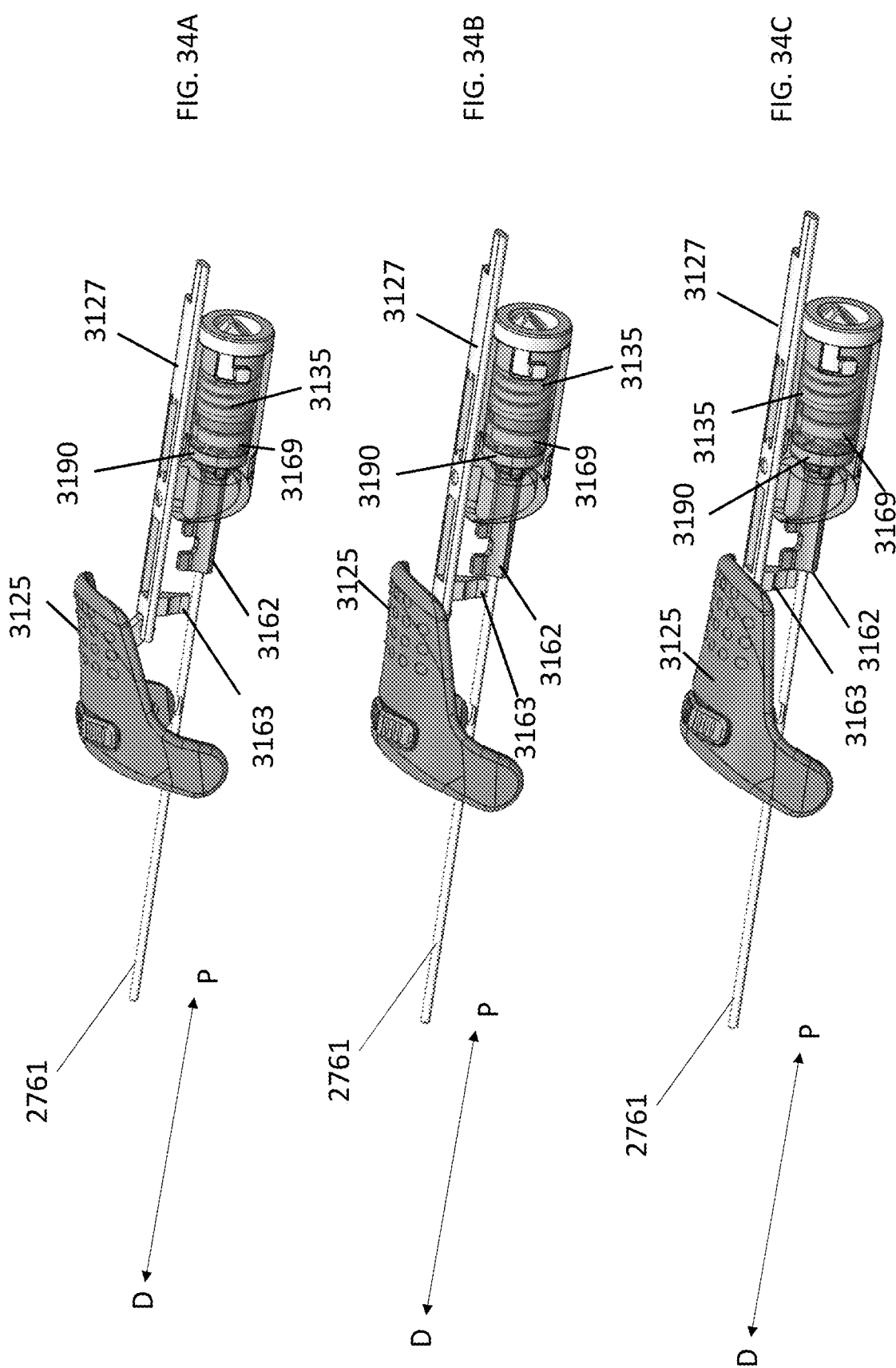

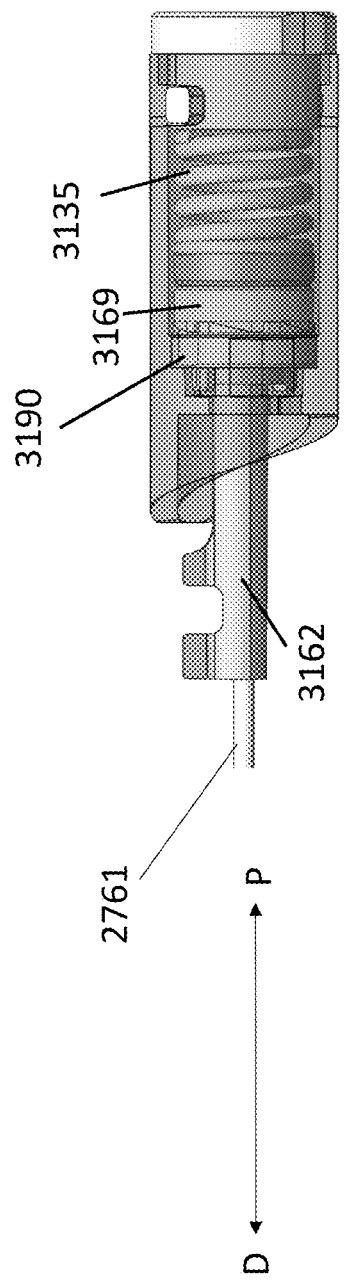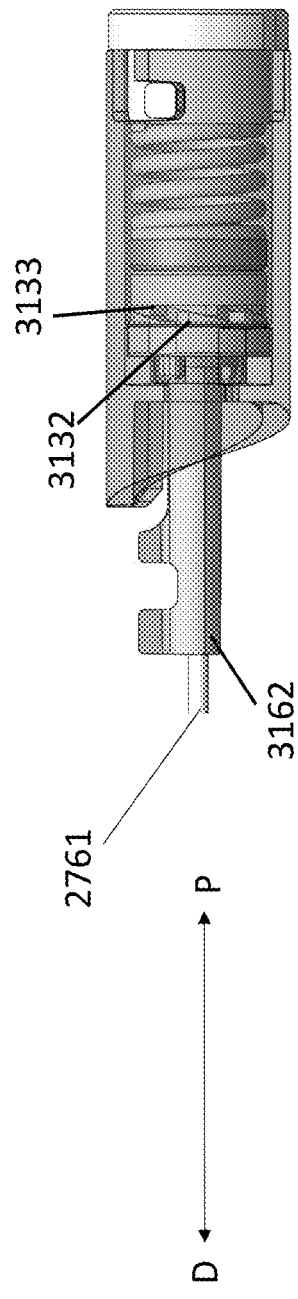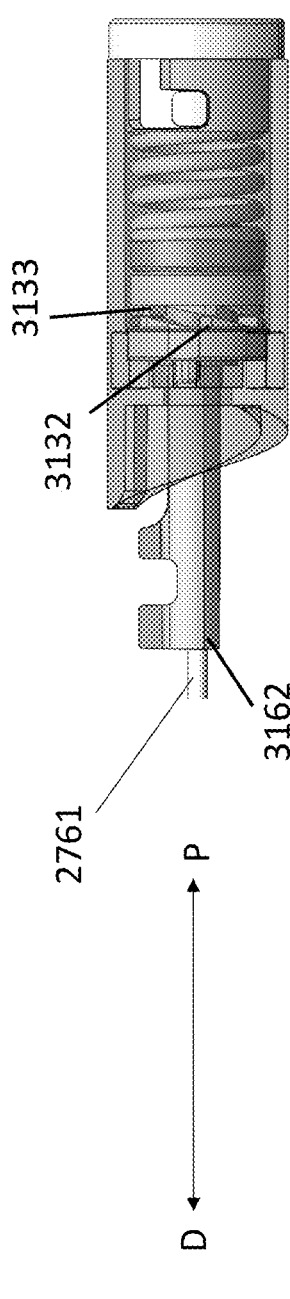

DEVICES AND METHODS FOR OCULAR SURGERY

CROSS-REFERENCE TO RELATED APPLICATIONS

This application is a continuation of co-pending U.S. application Ser. No. 15/970,439, filed May 3, 2018, which claims the benefit of priority under 35 U.S.C. § 119(e) to U.S. Provisional Patent Application Ser. Nos. 62/501,710, filed May 4, 2017, and 62/597,826, filed Dec. 12, 2017, which are each incorporated by reference in their entireties.

FIELD

The present technology relates generally to devices and methods for ocular surgery with one such procedure being removal of a lens from a human eye. More specifically, the technology relates to fragmenting, capturing, and extracting of lenticular or other tissue in ophthalmic surgery.

BACKGROUND

Certain types of conventional ophthalmic surgery require breaking up lenticular tissue and solid intraocular objects, such as the intraocular lens into pieces so that it can be extracted from the eye. For example, extraction of lenses for cataract surgery is one of the most common outpatient surgical fields with more than 3 million cases performed annually in the United States alone. During cataract surgery a commonly used method for lens extraction is phacoemulsification, which incorporates using ultrasonic energy to break up the lens and then aspiration to remove the lens fragments through the instrument. Other methods of lens fragmentation and extraction may include the use of instruments such as hooks, knives, or laser to break up the lens into fragments and then extract through an incision in the cornea in an ab interno approach. Intraocular, ab interno fragmentation of the lenticular tissue is extremely important in cataract surgery in order to allow removal of cataracts from ocular incisions that are typically not exceeding 2.8-3.0 mm.

A disadvantage of some lens extraction techniques are unwanted complications from aspiration of the lens particularly with the use of phacoemulsification. Ultrasonic energy and high volume during phacoemulsification may create turbulent flow that may have a deleterious effect on the tissue within the eye such as the corneal endothelium.

Additionally, certain aspiration and inspiration configurations require large pieces of capital equipment as in the case of phacoemulsification or may require certain resources such as wall vacuum that may not be available in all surgical settings, particularly in underdeveloped areas. Convention aspiration devices may be an independent tube or cannula or may be associated with another device such as a phacoemulsification unit ("phaco system"). Flow control and pressure control of phaco systems typically requires electronic control by a main console. A hand piece is used that has a suction line extending from the hand piece to the main console. The hand piece also typically has an inspiration line with inspiration driven by simple gravity feed or by flow controlled by the main console with a fluid bag/cartridge mounted to the console.

Another problem with phaco devices and other devices using a remote vacuum source is that the suction lines are long that means that they will often contain compressible material during the procedure, such as gas or compressible tissue. Long suction lines of compressible material affects the responsiveness of suction at the tip when suction is turned on and off. The problem of responsiveness is exacerbated by manually deformable/compliant hoses and lines that also respond to changes in pressure when starting and stopping suction, which further delays initiation and termination of suction at the tip. Yet another problem with some systems is that the disposal enclosure is also exposed to vacuum pressure and, as such, the container and gas or other compressible material therein, also responds to changes in pressure and further contributing to the delay in initiation and termination of suction at the tip and contributing to the low responsiveness of some systems.

Still another problem with conventional methods and devices for aspirating material from the eye is that the suction opening can readily clog during the procedure. Suction must be stopped and, if necessary, the material removed independently with another instrument inside the eye. The necessity to stop the procedure and unclog the distal opening undesirably increases the procedure time and need for unnecessary manipulations of the instrument(s) in the eye.

A final problem with some devices is the cost and complexity of the systems. A lower cost alternative with the same or better performance would also be desirable alternative such as one not requiring a costly control console and electronic control system.

SUMMARY

In an aspect, described is device for performing an ophthalmic procedure in an eye, the device includes a hand-held portion and a distal, elongate member coupled to the hand-held portion. The distal, elongate member includes a lumen operatively coupled to a vacuum source. The device includes a drive mechanism operatively coupled to the elongate member and configured to oscillate the elongate member. When in use, the device is configured to aspirate ocular material from the eye through the lumen and the drive mechanism is capable of retracting the elongate member in a proximal direction with a retraction speed profile and advancing the elongate member in a distal direction with an extension speed profile. The retraction speed profile is different from the extension speed profile.

An average retraction speed of the elongate member from the retraction speed profile can be lower than an average extension speed of the elongate member from the extension speed profile. The drive mechanism operatively coupled to the elongate member can be configured to asymmetrically oscillate the elongate member. The extension speed profile can include a maximum extension speed and the retraction speed profile can include a maximum retraction speed. The maximum retraction speed can be less than the maximum extension speed. The maximum retraction speed of the elongate member can be below a threshold speed at which cavitation bubbles would be generated in the eye.

A distal tip of the elongate member can be configured to move relative to the hand-held portion from a fully retracted configuration to a fully extended configuration to define a travel distance. The travel distance can be between approximately 0.05 mm and 1.0 mm. A pulse of aspiration can be drawn through the lumen of the elongate member during at least a portion of the travel distance as the elongate member advances in the distal direction. A pulse of aspiration can be drawn through the lumen of the elongate member during at least a portion of the travel distance as the elongate member retracts in the proximal direction. The device can further include an actuator configured to adjust the travel distance. The actuator can be configured to be mechanically adjusted by a user.

The device further include a control processor responsive to user input. The control processor can control one or more aspects of the drive mechanism. The one or more aspects can include the travel distance, an aspiration pulse frequency, or a frequency of an extension and retraction cycle. The control processor can be programmable and accept user input to adjust at least one aspect of the extension speed profile and the retraction speed profile. The control processor can be programmable and accept user input to adjust at least one of a maximum extension speed and a maximum retraction speed. The control processor can be programmable and accept user input to set a retraction speed limit. The control processor can be programmable and can be configured to be programmed by an input on the device. The control processor can be programmable and can be configured to be programmed remotely by an external computing device. The control processor can operate according to program instructions stored in a memory, the program instructions defining at least one of the extension speed profile of the elongate member and the retraction speed profile of the elongate member. The memory storing the program instructions can include a portion of a phacoemulsification system. At least one of the extension speed profile of the elongate member and the retraction speed profile of the elongate member can be adjustable through one or more changes to hardware, the hardware in operable communication with the control processor. The hardware can include a portion of a phacoemulsification system.

The drive mechanism can be pneumatic, electromagnetic, piezoelectric, or mechanical. The drive mechanism can include a piezoelectric element configured to oscillate the elongate member according to a voltage frequency that forms a non-sinusoidal motion pattern of the elongate member. The voltage frequency sent to the piezoelectric element can have a generally non-sinusoidal waveform. The voltage frequency sent to the piezoelectric element can include two or more overlapping sinusoidal waveforms configured to create an interference forming a generally non-sinusoidal waveform. The voltage frequency can contract the piezoelectric element slower than the voltage frequency allows the piezoelectric element to expand.

The drive mechanism can include a cam mechanism operatively coupled to the elongate member. A first amount of rotation of the cam mechanism can retract the elongate member in the proximal direction along the retraction speed profile. A second amount of rotation of the cam mechanism can advance the elongate member in the distal direction along the extension speed profile. The retraction speed profile can be at least in part a function of a rotational speed of the cam mechanism. The drive mechanism further can include a spring configured to be compressed by the cam mechanism. The first amount of rotation of the cam mechanism can compress the spring and the second amount of rotation of the cam mechanism can release the spring from compression. The extension speed profile can be a function of a force of the spring and a mass of the inner elongate member.

The elongate member can include a wall and a port through the wall, the port having a cutting surface. The elongate member can include a cutting tip. The cutting tip can be beveled. The cutting tip can include a distal opening from the lumen having a first dimension, the first dimension smaller than a second inner, cross-sectional dimension of the lumen of the elongate member. The distal opening of the cutting tip can have a first area, the first area smaller than a second inner cross-sectional area of the lumen of the elongate member.

The device further can include an outer tube comprising an outer tube lumen. The elongate member can be positioned within the outer tube lumen. The ocular material can be aspirated through the outer tube lumen. The ocular material can be aspirated through both the outer tube lumen and the lumen of the elongate member. The device can further include an outermost tube having an outermost tube lumen. The outer tube can be positioned within the outermost tube lumen. The outermost tube can include one or more ports for delivering irrigation fluid to the eye. The outermost tube can include an elastic material.

The elongate member can be capable of being repeatedly advanced and retracted along a longitudinal axis of the elongate member. The elongate member can be capable of being repeatedly advanced and retracted along an elliptical pathway relative to a longitudinal axis of the elongate member. The elongate member can be capable of being repeatedly advanced and retracted along a non-linear pathway relative to a longitudinal axis of the elongate member. The non-linear pathway can be curvilinear. The non-linear pathway can be elliptical. The elongate member can be torsionally oscillated. The extension speed profile can include a first angular rotational speed profile produced through being torsionally oscillated. The retraction speed profile can include a second, different angular rotational speed profile.

The vacuum source can deliver a pulsed vacuum to a distal portion of the lumen of the elongate member. The vacuum source can be located within a housing of the hand-held portion. The vacuum source can be located on a housing of the hand-held portion. The drive mechanism can be repeatedly advanced and retracts the elongate member while the vacuum source delivers the pulsed vacuum. After the elongate member completes a single cycle of one advancement and one retraction, the vacuum source can deliver at least one pulse of vacuum to the distal portion of the lumen. As the elongate member passes through a single cycle of one advancement and one retraction, the vacuum source can deliver a plurality of pulses of vacuum to the distal portion of the lumen. After each pulse of vacuum, the device can produce a pulse of positive-pressure regurgitation. As the elongate member passes through an oscillation cycle of one advanced and one retraction, the vacuum source can deliver at least one pulse of vacuum to the distal portion of the lumen. As the elongate member retracts during the oscillation cycle, the vacuum source can deliver at least one pulse of vacuum to the distal portion of the lumen. As the elongate member advances during the oscillation cycle, the vacuum source can deliver at least one pulse of vacuum to the distal portion of the lumen.

The ocular material can include at least one of fragmented lens material or emulsified lens material. The ocular material can include vitreous material. The drive mechanism can be configured to oscillate the elongate member at a frequency of oscillation that is ultrasonic. The drive mechanism can be configured to oscillate the elongate member at a frequency of oscillation that is greater than about 20,000 Hz. The drive mechanism can be configured to oscillate the elongate member at a frequency of oscillation that is between about 0.5 Hz and about 5000 Hz. The frequency of oscillation can be selectable by a user through an input to a control processor, the control processor being in operative communication with the drive mechanism.

In an interrelated aspect, described is a method for performing an ophthalmic procedure in an eye. The method includes inserting a distal portion of a device into an anterior chamber of the eye and accessing a lens of the eye with the distal portion of the device. The device further includes a hand-held portion having a vacuum source configured to create pulses of discontinuous negative pressure and to create pulses of discontinuous positive pressure. The pulses of discontinuous negative pressure being interspersed by the pulses of discontinuous positive pressure and having a frequency. The device includes a distal, elongate member coupled to the hand-held portion and forming part of the distal portion. The elongate member has an internal lumen and an opening at a distal end region of the elongate shaft. The method further includes activating the device to create the pulses of discontinuous negative pressure through the internal lumen of the elongate member to aspirate a first amount of material into the internal lumen through the opening at the frequency, and to create the pulses of discontinuous positive pressure interspersed with the pulses of discontinuous negative pressure to expel, from the internal lumen through the opening, a second amount of material at the frequency. The second amount is substantially less than the first amount.

In an interrelated aspect, described is a device for performing an ophthalmic procedure in an eye including a hand-held portion and a distal, elongate member coupled to the hand-held portion. The distal, elongate member includes a lumen and an opening at a distal end region of the elongate member. The device includes a vacuum source in fluid communication with the opening at the distal end region of the elongate member. The vacuum source is configured to deliver pulses of discontinuous negative pressure to the distal end region of the lumen.

The vacuum source can include a pump positioned within an interior of the hand-held portion. The pump can include at least one pumping chamber having an inlet opening and an outlet opening, the inlet opening in fluid communication with the lumen of the elongate member. The pump can include a piston positioned within the at least one pumping chamber; and a drive mechanism configured to oscillate the piston within the at least one pumping chamber to create the pulses of discontinuous negative pressure. The negative pressure can be from 10 inHg up to about 30 inHg. The pulses of discontinuous negative pressure can have a cycling frequency of between about 1 Hz and about 100 Hz. A first pulse of negative pressure can draw a first amount of fluid from the lumen of the elongate member into at least one pumping chamber positioned within the hand-held portion through an inlet opening. A first pulse of positive pressure within the at least one pumping chamber can expel the first amount of fluid from the at least one pumping chamber through an outlet opening. A volume of the first amount of fluid can be between about 0.1 mL up to about 1.0 mL. Movement of a piston in a first direction within the at least one pumping chamber can create the first pulse of negative pressure. Movement of the piston in a second, opposite direction can create the first pulse of positive pressure. A compliant valve can be positioned within the inlet opening. Movement of the piston a second distance in the second, opposite direction can seal the inlet opening and transmit an amount of the first pulse of positive pressure through the compliant valve to the lumen of the elongate member. The amount transmitted can cause a second amount of fluid to be expelled out the opening at the distal end region of the elongate member. The outlet opening can be regulated by a valve. The valve can be a ball type check valve. The outlet opening can be in fluid communication with an evacuation chamber.

The device can further include a drive mechanism operatively coupled to the elongate member and configured to oscillate the elongate member. In use, the drive mechanism can retract the elongate member in a proximal direction with a retraction speed profile and advance the elongate member in a distal direction with an extension speed profile. The retraction speed profile can be different from the extension speed profile. An average retraction speed of the elongate member from the retraction speed profile can be lower than an average extension speed of the elongate member from the extension speed profile. The drive mechanism operatively coupled to the elongate member can be configured to asymmetrically oscillate the elongate member. The extension speed profile can include a maximum extension speed and the retraction speed profile can include a maximum retraction speed. The maximum retraction speed can be less than the maximum extension speed. The maximum retraction speed of the elongate member can be below a threshold speed at which cavitation bubbles would be generated in the eye. A distal tip of the elongate member can be configured to move relative to the hand-held portion from a fully retracted configuration to a fully extended configuration to define a travel distance.

In some variations, one or more of the following can optionally be included in any feasible combination in the above methods, apparatus, devices, and systems. More details of the methods, apparatus, devices, and systems are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking, the figures are not to scale in absolute terms or comparatively, but are intended to be illustrative. Also, relative placement of features and elements may be modified for the purpose of illustrative clarity.

FIG. 11 shows still another tissue manipulator with a net-like material within the loops.

FIG. 12 shows still another tissue manipulator having a loop with an integrally formed concave element.

FIG. 23A shows an actuator having a foot pedal in a resting or off position.

FIG. 23B shows the actuator in the fully on position.

FIGS. 28A-28B show side views of an implementation of a device for cutting and aspirating material from an eye.

FIGS. 29A and 29B is a perspective view and a cross-sectional view, respectively, of an interrelated implementation of a device for cutting and aspirating material from an eye.

FIG. 29C is a perspective view of an elongate member coupled to an implementation of an oscillating drive mechanism.

FIGS. 29D-29F are side views of the oscillating mechanism of FIG. 29C in various stages of rotation.

FIGS. 33A-33C illustrate various stages of actuation of a device having an elongate member.

FIGS. 34A-34C illustrate partial views of the device of FIGS. 33A-33C in the various stages of actuation.

FIGS. 35A-35C illustrate partial views of the device of FIGS. 33A-33C in the various stages of actuation.

Figure 1:
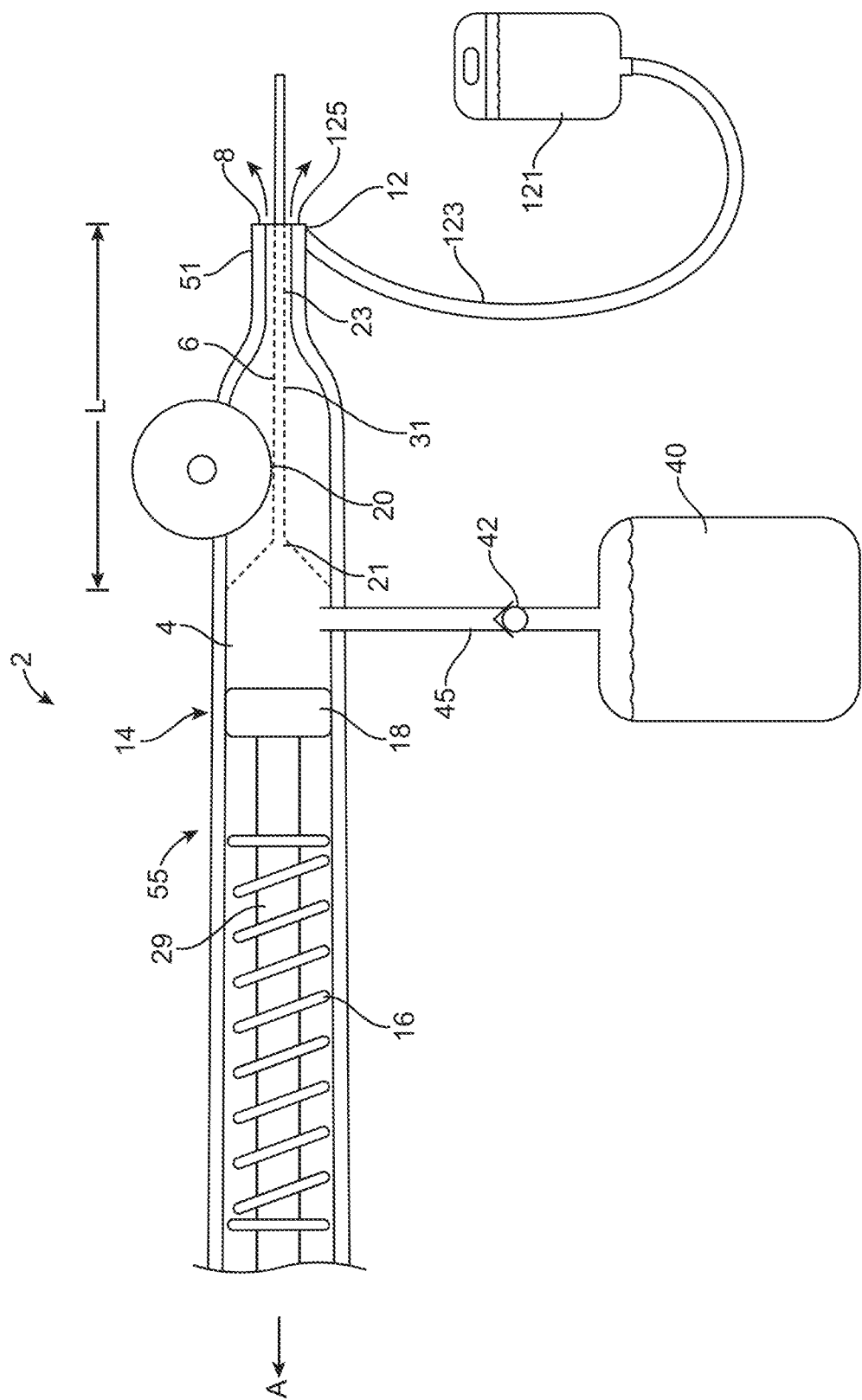
FIG. 1 shows a device for suctioning material.

It should be appreciated that the drawings are for example only and are not meant to be to scale. It is to be understood that devices described herein my include features not necessarily depicted in each figure.

DETAILED DESCRIPTION

Described herein are methods and devices for intraocular fragmentation and removal of the lens and other tissues during intraocular surgery. The devices described herein allow for extracting tissue from the anterior chamber without damaging other ocular structures. The devices and methods described herein are capable of inspiration or aspiration with less capitally intensive equipment.

In various embodiments an ocular surgical device is described that uses cutting strings, filaments, snares, baskets, bags, loops and other devices designed to engage and fragment the lenticular tissue and aid in its removal from the eye in a minimally invasive, ab-interno approach. In other embodiments, described are devices and methods for inspiration and aspiration of fluids from the eye. The aspiration devices described herein have improved responsiveness as compared to devices using remote suction with long manually deformable/compliant suction lines. In one aspect, provided is a hand-held device that can also be powered (manually) by the user and does not require electronic control. The device can further have a short suction path with a small suction volume. The device can include a hand-held suction source thereby eliminating the need for hoses from the hand piece to the console. This greatly reduces the length of line and also the amount of material subject to the suction pressure that can compress or expand to reduce responsiveness. In some implementations, the devices described herein can be "all-in-one" devices providing cutting, fragmenting, infusing, and/or aspirating functions all within the same hand-held device.

The devices described herein can include a purging mechanism that purges the material from the suction path and into the disposal enclosure. The purging mechanism may be part of the suction device or may be a separate mechanism. In a specific aspect, the purging mechanism is a plunger that pushes the material in direction opposite the suction direction and into the disposal enclosure. A valve, which may be a one-way valve, permits the material to enter the disposal enclosure. The valve (or one-way valve) may also prevent the material from entering the disposal enclosure when material is suctioned along the suction path during use. Purging the suction path during the procedure reduces the volume of material in the suction path compared to systems having long fluid lines to remote suction systems. Purging the suction line may occur in-between suction times and may be accomplished using a movable element that also creates the suction pressure. In a specific aspect, the movable element may be a spring-loaded plunger that is manually set.

In still another aspect, the suction device may include a movable element within the suction path. For example, the suction device may be the spring-loaded plunger that is manually actuated. Other suction devices are considered herein, including a pneumatic system with bladders and/or balloons, a deformable wall and roller system, or any other suitable system for creating suction pressure such as a venturi. The movable element of the suction device may also be used to purge the suction path but the two functions may be separated and performed in different manners.

In still another aspect, a valve may be coupled to the hand held unit and positioned along the suction path. The valve is coupled to a wire and a spring acts on the valve to bias the valve closed. The wire is coupled to an actuator that may include a foot pedal to control movement of the wire and the valve. The foot pedal is also operably coupled to the suction source so that movement of the foot pedal by the user controls the vacuum source. When the actuator is initially actuated (by pressing the foot pedal), the actuator moves the valve to a partially open position during a first phase of displacement. The actuator controls the vacuum or suction source to gradually increase the vacuum pressure as the actuator displacement increases during the first phase. During the first phase, the suction pressure may be increased to a target or maximum pressure that may be at least 570 mm Hg. Stated another way, the actuator controls the valve to be no more than half open until a target pressure is reached during the first phase of displacement. The actuator may have a second phase of displacement that follows the first phase. The second phase may be carried out by with the valve progressively opening from the partially open position to increase the cross-sectional flow area as the actuator increases in displacement. Alternatively, during the second phase, the actuator controls the valve to increase and decrease the suction pressure exerted at the opening (and the flow rate) in a cyclic manner at a rate of at least 1 Hz in any suitable manner such as moving the valve (as discussed below) between the first position and the second positions. The second phase may be carried out with the suction pressure being constant and may also be at maximum.

The actuator may also have a third phase of displacement that follows the second phase of displacement. In the third phase of operation the valve is moved between an initial (or first) position and a second position at a varying duty cycle to modulate the time-average flow rate while the suction source pressure may remain constant and/or maximized. The first position has a smaller cross sectional flow area than the second position. As greater flow is required by the user the time the valve is held in or nearer to the second position increases. This corresponds to an increased duty cycle between the two positions with the duty cycle of the second position increasing relative to the first position. A pulse rate of at least 1 Hz may be appropriate. Stated another way, the shift in the duty cycle during the third phase causes the valve to increase a time that the valve is nearer to the second position than to the first position as the displacement of the actuator increases. Alternately, the same effect can be achieved keeping the pulse rate duty cycle constant but increasing the displacement of the actuator during the third phase by increasing the distance between the first position and the second position so that more of the aperture is exposed during each cycle and, therefore, typically a higher volume flow rate is achieved. The increase in displacement of the actuator causes the second position of the valve during the third phase to define an increasing cross-sectional flow area. Stated another way, the increase in displacement of the actuator during the third phase increases a distance between the first position and the second position so that more of the aperture is exposed and, therefore, typically a higher volume flow rate of suction is achieved.

The devices and methods described herein can reduce the likelihood of clogging by providing a restrictor that restricts material in the vicinity of the distal opening. The restrictor reduces the likelihood of clogging by restricting the material that can enter the distal opening. The restrictor may also be movable (longitudinally and/or rotationally) to clear material from in and around the opening and to gather material as well. It should be appreciated that the devices can also include an elongate member having a distal tip having a reduced inner diameter compared to an inner diameter of regions proximal to the distal tip. Clogging can be mitigated by narrowing the size of the opening at the distal tip compared to the size of the lumen.

Described herein is a tissue manipulator and method of manipulating tissue. The tissue manipulator has a shaft having a lumen with a distal opening. A first loop has a first leg and a second leg with at least one of the first and second legs extending through the lumen. The first loop is movable from a collapsed position to an expanded position when the at least one of the first and second legs is advanced through the lumen and out the distal opening in the lumen. A second loop has a first leg and a second leg with at least one of the first and second legs extending through the lumen. The second loop being movable from a collapsed position to an expanded position when the at least one of the first and second legs is advanced through the lumen and out the distal opening in the lumen. The shaft may be sized for introduction of a distal end of the shaft into an eye.

The first loop may have an unbiased shape that bounds an area defined in an orientation that maximizes the area. The area has an effective diameter that is equal to the diameter of a circle having the same area. The first loop moves toward the unbiased shape when moving from the collapsed position to the expanded position. The effective diameter of the area of the first loop is 4.5 mm to 6.5 mm or can be 5.0 mm to 6.0 mm in the expanded position. The effective diameter of the unbiased shape of the second loop may be within 20% of an effective diameter of the expanded position of the first and/or second loops. In this manner, the first and/or second loops provide for a soft deployment and are flexible during use. Use of a superelastic material further enhances the flexibility of the first and second loops. To this end, the first and second loops may be formed of superelastic wire having a diameter of about 0.003" to about 0.006" although any size may be used with any suitable cross-sectional shape.

The tissue manipulator may also include an intermediate element positioned between the first loop and the second loop. The intermediate element may be a third loop positioned between the first loop and the second loop. The intermediate element may include an interconnecting element extending between the first loop and the second loop. The interconnecting element may be integrally formed with the first loop and the second loop. Alternatively, the interconnecting element may be a flexible filament extending between the first loop and the second loop. The third loop may have the features of the first and second loops.

The first and second loops provide a controlled amount of exposed surface therebetween to control, and optionally cut, a controlled amount of the material. The exposed surface between the first loop and the second loop has an area of 15 $mm^3$ to 60 $mm^3$. Stated another way, the exposed surface between the first loop and the second loop is 3-10 times the effective diameter in the expanded position (or the unbiased position since they may be the same). The exposed surface between the first loop and the second loop may have 2-8, 2-6, 2-4 or even just 2 independent cells when viewed in a radially inward direction relative to the orientation axis of the first and second loops. The exposed surface has an area that is at least 4 times larger than a surface area of the intermediate element when expanded between the first and second loops and viewed radially inward with respect to the loops. In this manner, the intermediate element does not take up an excessive amount of room as compared to some net-type devices.

The device may include a first support element extending from a distal end of the shaft when the first loop is expanded. The first support element may be an elongate element that extends to a free end. The first support element is positioned with the free end positioned within an area of the first loop when viewing the first loop along an orientation that maximizes the area of the first loop. A second support element that cooperates with the second loop in the same manner may also be provided. The first loop and/or second loop may have at least one interconnecting element extending from a first connection to the first loop to a second connection to the first loop or may be substantially free of any such interconnecting elements depending upon the desired use.

In yet another aspect, the tissue manipulator can have a concave element coupled to a first loop to form a basket. The concave element may have one end integrally formed with the first loop with the other end movable within the lumen independent of the first and second legs. Alternatively, both ends may be integrally formed with the loop. A second loop having another concave element may be provided to form another basket with the two baskets being movable relative to one another between a nested position and a position in that the two baskets oppose one another.

In use, the device is introduced into the eye with a distal end and distal opening of the shaft inside the eye. The first loop is expanded and the second loop is also expanded (simultaneously or independently). Material is positioned within the first and/or second loop and then the first and/or second loop is collapsed around the material to contain, manipulate or cut the material. Furthermore, a suction source may be coupled to the lumen to suction the material, fluid, and the cut material into the lumen or another lumen. The method may include all features of the device that are expressly incorporated here for all purposes.

Another device is provided that has a shaft having an elongate element that is bowed outwardly by biasing the elongate element with a load when deployed. The loop is movable from a collapsed position to an expanded position when a first shaft part (coupled to the first end of the elongate element) and a second shaft part (coupled to the second end of the elongate element) are moved relative to one another from a first position to a second position. Material is positioned in the loop and then cut by collapsing the loop. The loop may be expanded so that the loop advances between the capsular bag and a whole lens contained within the capsular bag.

The elongate element may have a first and a second flexible portion with an intermediate portion therebetween that is at least 1.5 more stiff in bending than the flexible portions. In another aspect, the first end may change in orientation relative to the proximal end of the shaft when deployed. The change in orientation may be provided by simply pinning or otherwise rotatably coupling the first end to the shaft so that the angle (orientation) changes by at least 120 degrees or 180 degrees+/−45 degrees when the first and second shaft parts move from the first position to the second position. The distal end of the shaft may also include a flexible portion that changes in orientation relative to the proximal portion of the shaft when the loop is expanded. The distal end may change in orientation by at least 30 degrees. The first end rotates so that the loop advances distally beyond a distal end of the shaft as the loop moves from the collapsed position to the expanded position. The second end may also be rotatably coupled to the shaft or may include the flexible portion. Use of and discussion of all aspects of the first flexible portion or the first end are equally applicable to the second end and are specifically incorporated herein. Furthermore, a mixture of first end and second end are also expressly incorporated such as a flexible first end and a rotatable second end.

A plunger device may be depressed in order to create a vacuum to provide suction when connected to the hand piece. During cataract surgery it is desirable to have a supply of balanced saline solution (BSS) delivered to the eye as well as a supply of suction to remove fluids and other materials. Certain ophthalmic surgical tips have the ability to inspirate and aspirate fluid through dual lumen designs. These devices are connected to a supply of suction and pressurized BSS fluid. Described herein are devices that include the ability to provide suction or BSS pressurized fluid through simple mechanisms, some of which may be manually powered or regulated. The hand piece may also be connected to a pressurized BSS source such as a hanging bag or any number of other pressurized sources such as spring loaded syringes and the like. Alternatively vacuum may be supplied by any number of other mechanisms such as a bellows mechanism, diaphragm pump, venturi pump, entrapment pump, positive displacement pump, regenerative pump, momentum transfer pump, sealed containers of vacuum that are released, micro pumps, or the like. When connected to a hand piece, suction is supplied to the tip to provide aspiration. In one embodiment, a compressible bulb such as a turkey baster may be used to provide suction. The user may depress the bulb with a finger and control the amount of suction by the release of the finger from the bulb. Other lever mechanisms may additionally create vacuum in a hand held instrument. In some embodiments, a nurse or assistant may create vacuum with a device that is connected to the hand held instrument. For example, a foot pedal may be used to create suction that is connect to the surgeon's device. The hand piece may contain any number of waste containers that contain the withdrawn fluid and store it in the hand piece or off the hand piece. The various vacuum mechanisms may be powered in any number of ways such as a manual operation by the user or assistant. In this embodiment, the user may 'charge' the device with energy such as by depressing a spring loaded plunger before beginning the procedure and then controlling the amount of vacuum with a valve or other input mechanism. In some embodiments, the BSS pressurized supply may be coupled to the hand piece and may be 'charged' at the same time as the vacuum or separately. For example, the surgeon may depress one plunger that creates a spring force on the vacuum and the BSS fluid such that the surgeon may control the release of both with a single button or multiple buttons during the procedure. In other embodiments, the BSS may be in a hanging bag or other pressurized system and piped into the hand piece.

In some embodiments, the hand piece may include a flow control valve for additionally allowing the surgeon to select the rate or pressure of the fluids aspirated or inspirated. The surgeon may adjust the amount of flow desired by rotating a knob that compresses a tube a certain amount or opens a ball valve a certain amount or any number of other flow control mechanisms. The device may also include a button that can be depressed to regulate when the device is inspirating or aspirating. The amount the surgeon depresses the button may in itself control the variable flow. There may be a single button for controlling inspiration and aspiration or individual buttons for each. Where a button is described herein, it should be appreciated that the button can be a multi-way button to activate more than a single function. Similarly, the device can incorporate more than a single button to access the various functions of the device (i.e. aspiration, inspiration, cutting, etc.) It should be understood that button simply means a control interface for the user and that any number of interfaces may be contemplated. Additionally the control interface may be on the hand held device itself or may be in another location. For example a foot pedal may be used to control the flow or a separate device held with a different hand may be used.

In some embodiments, the device may include a dual lumen design for inspiration and aspiration. In other embodiments, there may be more than 2 lumens or the lumens may be oriented concentrically.

In various other embodiments, device and methods for the removal or fragmentation of the lenticular tissue is described. Bags or meshes that are attached to snares or loops may be incorporated to grab lenticular tissue that is either whole or partially fragmented. The bags and meshes may be used to pull the tissue from the eye through a paracentesis. In some embodiments, a separate tool may be inserted into the bag or mesh after a fragment of the lens is captured and the separate tool may be used to break the tissue into smaller fragments. For example, a spinning cutter instrument may be inserted either with a different device or through a lumen of the bag device to cut the tissue into smaller pieces while it is within the bag or container so that may be withdrawn through the paracentesis.

In other embodiments, various baskets are used to capture the lens material and either pull it from the eye or further fragment the material into smaller pieces that may be aspirated. In each embodiment, the bags and meshes and baskets may be made of any number of materials. For example, Nitinol material may be used and shaped into the proper orientation. Certain material such as Nitinol may be elastically changed between multiple shapes and used to enter the eye through a small profile and expand within the eye to capture the lens material. Any number of shapes are contemplated such as coin purses, expanding balloons, curved bags, and the like. The devices may be comprised any plurality of materials such as stainless steel, Nitinol, biocompatible plastics, and the like. Additionally, Nitinol may be used in either its super elastic state or shape memory state or both in multiple components.

In some embodiments, cutter and augers and the like may be used to mechanically fragment the lens into multiple pieces. These devices may additionally include integrated suction for the aspiration of the lens material.

The aspects mentioned above are applicable to all suitable embodiments described herein. Thus, use of Nitinol as described above is applicable to all suitable aspects concerning any cutting filament, element or device described herein. Similarly, any aspect of the aspiration device described above are equally applicable to all aspiration embodiments described herein. Finally, the features, aspects and methods of using each of the devices and methods is equally applicable to the other devices and methods described herein (including cutting) and all such features are expressly incorporated herein.

Referring now to the figures, FIG. 1 shows a device 2 for removing material during procedures on the eye. The device 2 has a suction path 4 that extends through a lumen 6 to an opening 8 from the lumen 6 at or near a distal end 12 of the lumen 6. The opening 8 can be positioned in the eye for removal of material from the eye, such as lens fragments within a capsular bag. A suction source 14 can be coupled to the suction path 4 to draw material into the opening 8. The suction source 14 can be a manually-loaded spring 16 coupled to a plunger 29 having a sliding seal 18. Other suitable sources of suction are considered herein. The suction source 14 can be located within the hand-held portion of the device 2 near the distal end region providing for a short suction path 4 and the benefits of such a short path and small suction volume within the suction path 4.

The suction path 4 can have a proximal suction volume 21 and a distal suction volume 23. The proximal suction volume 21 may be substantially under the influence of suction pressure by the suction source 14 at all times so that the system is prepared or "primed," in a sense, to suction material at any time during a procedure. The proximal suction volume 21 of the suction path 4 may be less than 25 ml and already under suction pressure proximal to an actuator 20 of the device 2. The proximal suction volume 21 can be defined by the volume of the suction path 4 between the actuator 20 and the suction source 14 (in this case the sliding seal 18). The distal suction volume 23 of the suction path 4 is also small since the actuator 20 is positioned relatively near the opening 8. In some implementations, the distal suction volume 23 may be less than 2 ml. The actuator 20 may be movable to a number of different positions and may be continuously variable to allow for the desired amount of suction by the user. The term actuator 20 is used herein to refer to the element that acts on the suction path 4. The actuator 20 may include one or more inputs such as a slider, switch, button, or other type of physical element configured to be manually or otherwise activated. The input may be located directly on the handheld component of the device and interface directly with the actuator 20 or the input may be remote to the actuator 20. In some implementations, the button may act directly on the actuator 20 and may also have elastic properties itself. The input, whether a slider, switch, button, or other type of actuator, can be a multi-way input to access more than a single function of the device or the device can incorporate a plurality of inputs each with the capability of actuating a particular function (i.e. aspiration, infusion, cutting, etc.).

The suction source 14 can include a movable element that can be displaced in a direction shown by arrow A to draw the material into the opening 8 and through the suction path 4. The movable element is displaced in an opposite direction to the direction A to move material into the suction path 4 into the disposal enclosure 40 as explained in greater detail below. The configuration of the suction source 14 can vary. In some implementations, the suction source 14 can be hand-held in that the movable element is part of a hand-held unit. The device also may have no electronic control and no electric powered parts and may even be powered by the user in that the spring 16 is manually loaded (extended). The movable element can include a plunger 29 having a sliding seal 18. The spring 16 can be coupled to the plunger 29 to manually load the movable element with a spring load. The configuration of the movable element can vary including a piston, a plug, stopper, ball or a movable part of a wall such as a bladder or balloon. Once loaded, the plunger 29 and sliding seal 18 of the movable element continuously exerts suction pressure until the spring 16 is completely relaxed or otherwise restrained.

The actuator 20 can serve as a valve for the suction path 4 and may act on a deformable part 31 of the suction path 4. The opening 8 can be exposed to suction pressure in that suction pressure may be applied by exposing the opening 8 to the suction pressure when activating the actuator 20. Alternatively, the opening 8 may be exposed to the suction pressure when activating the suction device itself. For example, even the spring-loaded mechanism of the device 2 may be coupled to a controller (not shown) so that suction pressure is applied and released and, when applied, exposes the opening 8 to suction pressure to draw material into the opening 8. The actuator 20 may be continuously variable by simply depressing more or less to deform more or less of the deformable part 31 between at least two different open positions. FIG. 1 shows a continuously variable actuator 20 between the fully open and fully closed positions by simply varying the amount the deformable part 31 is deformed.

A disposal enclosure 40 is coupled to the suction path 4 to receive material from the suction path 4. A valve 42, such as a one-way valve, can be positioned between the disposal enclosure 40 and the suction path 4. The valve 42 permits material to move to the disposal enclosure 40 and isolates the disposal enclosure 40 during suction operation. The valve 42 may be an actuated valve or a passive one-way valve that opens and closes automatically as necessary, for example, upon increase in fluid pressure on one side of the valve 42 relative to the other. The valve 42 isolates the disposal enclosure 40 so that the compressibility of the material does not affect the responsiveness of the system as described herein. The suction path 4 may increase in diameter at parts outside the eye similar to or the same as a syringe. Furthermore, the suction path 4 may take any of a variety of shapes. The disposal enclosure 40 is configured to be supported independently, for example, by the table a traditional hanger, or any other suitable structure. Furthermore, the disposal enclosure 40 may be hand-held or remotely located. The disposal enclosure 40 has a disposal lumen 45 extending from the suction path 4 to the disposal enclosure 40. As mentioned above, the valve 42 (or one-way valve) isolates the disposal enclosure 40 from the suction pressure thereby preventing any pressure response by the disposal enclosure 40 during use.

The device 2 can be hand-held to a large extent in that the suction path 4 is hand-held and the suction source 14 is hand-held as well. The suction source 14 need not include tubing or the like from the suction machine, but defines the mechanical source that is creating the suction pressure. It should be appreciated that any of a number of suction mechanisms are considered herein. For example, a roller with tubing, a pneumatic system, a bladder or venturi may be used to create suction pressure. The suction path 4 may also be more than half non-manually deformable or even at least 90% non-manually deformable. Most systems with remote suction devices include manually deformable tubes and hoses that may respond to pressure changes and can further reduce responsiveness. The suction path 4 may be small to further improve responsiveness. To this end, the suction path 4 may have a length (longitudinal) L of less than 20 cm or a volume of less than 25 ml and even less than 15 ml.

As mentioned above, the devices described herein are particularly useful for removing material from the eye. As such, the lumen 6 may be appropriately sized. The suction path 4 includes a shaft 51 having the lumen 6. The lumen 6 is sized for introduction into the eye and has a longitudinal axis with a cross-sectional area of the outer perimeter (or diameter) of the shaft 51 being no more than 0.8 $mm^2$ while the lumen has a cross-sectional area of at least 0.28 $mm^2$.

The plunger 29 and sliding seal 18 can be operated to manually purge the suction path 4. Purging the suction path 4 reduces the material in the suction path 4 when suction is reinitiated. A purging mechanism 55 may be the movable element (e.g. plunger 29 and sliding seal 18) or may be a separate element that moves the material from the suction path 4 to the disposal enclosure 40. In one aspect, the purging mechanism 55 moves the material through the suction path 4 in an opposite direction to suction of material along the suction path 4 as shown by arrow A. The valve 42 permits flow from the suction path 4 to the disposal enclosure 40 when the movable element is advanced. The purging mechanism 55 may also include an element separate from the movable element that forms part of the suction device 14 and may be completely independent of the suction source 14. As defined herein, the suction path 4 includes volumes occupied by movable element. For example, the sliding seal 18 moves between fully retracted and fully advanced positions with the suction path 4 essentially changing in length and in volume. As used herein, the defined length and volume of the suction paths shall be defined with the minimum volume contained therein by the suction source 14. Thus, the length and volume is defined by the most advanced position of the plunger/movable element that minimizes the length and volume.

As described herein, "compressible" material such as a gas may also refer to the "expansibility" of the material in that suction pressure applied to entrained gas and material may permit the gas and material to expand slightly under the lower suction pressure (rather than compress). The compressibility (or expandability) of gasses and the effect on pressure responsiveness is typically deemed a problem of "compressibility" of gasses and is also so described herein and it is understood that this term also applies to the expandable nature of gasses and materials. With respect to the hoses and lines, the ability to resist compression by the suction pressure is a material property relevant to the responsiveness of such systems with manually deformable materials typically also responding mechanically to pressure variations.

Figure 2:
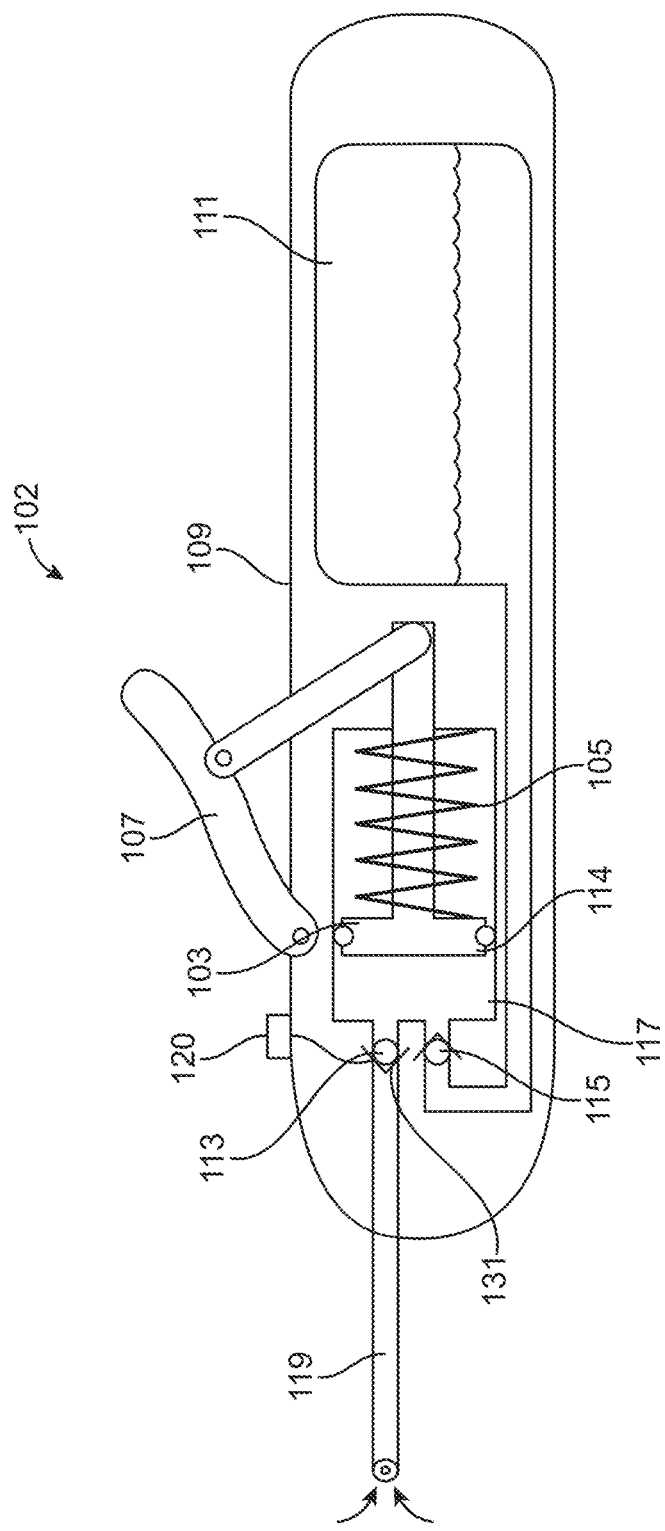
FIG. 2 shows another device for suctioning material.

Referring to FIG. 2, shows an interrelated device 102 for removing material during a procedure. In this implementation, the suction source 114 can include a plunger 103 that is manually loaded with a spring 105. The spring 105 can be loaded with a pivoting lever 107 attached to a housing 109. The disposal enclosure 111 can be mounted to and within the housing 109 such that it is hand-held with the device 102. Pressing the lever 107 advances the plunger 103 to purge the material in suction path 4 to the disposal enclosure 111. A first valve 113 and a second valve 115 (which may be one-way valves) permit suction through the lumen and purging of material into the disposal enclosure 111.

The lever 107 may be selectively locked and unlocked once advanced or the user may continue to apply pressure to the lever 107 to essentially stop suction. When suction is desired again, the lever 107 may be released with variable pressure to vary the amount of suction produced. Alternatively, the first valve 113 may include an interface 120, such as a button, which is actuated to open and close the suction path. The interface 120 may act as an actuator described herein and separates a proximal volume 117 from a distal volume 119 of the suction path. The first valve 113 may be formed over a deformable portion 131 of the suction path along the valve 113 for use as described herein and all such uses of the deformable portion and actuator are expressly incorporated here. The second valve 115 (which may be a one-way valve) regulates flow to the disposal enclosure 111. As shown in FIG. 1, a source of irrigation fluid 121 may also be coupled to the shaft 51 for irrigating the eye using a source of irrigation fluid 121. The source of irrigation fluid 121 may be a gravity fed bag or part of a fluid delivery system such as a phacoemulsification system. An irrigation lumen 123 has an opening 125 positioned in the eye for delivery the irrigation fluid.

Figure 3:
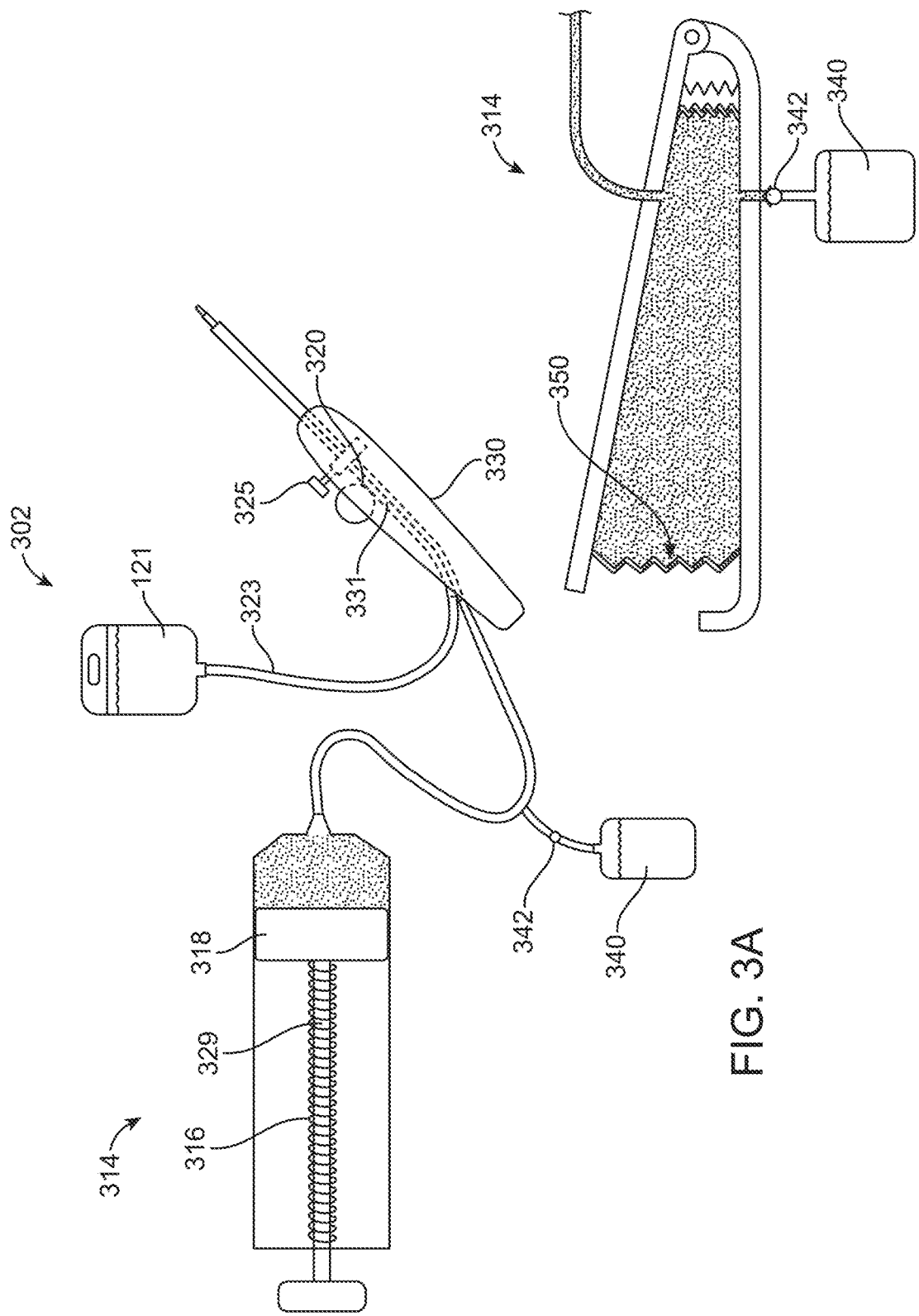
FIG. 3A shows still another device for suctioning material.
FIG. 3B shows an alternative suction source using a bellows.

Referring to FIGS. 3A-3B, another suction device 302 is shown wherein the same or similar reference numbers refer to the same or similar structure. The suction source 314 can include a movable element that includes a sliding seal 318 coupled to a plunger 329 manually loaded with a spring 316. In this implementation, the suction source 314 is shown to be remote from the hand-held housing 330. The spring 316 is loaded manually. An irrigation source 121, such as a bag of balanced saline solution, can be coupled to an irrigation lumen 323. A valve 325 can control flow of the irrigation fluid. The actuator 320 is used in the same manner as the actuator 20 above and suction path includes the deformable portion 331 and all aspects and methods of these elements are incorporated expressly here. Purging of the suction path is also accomplished in the same manner with the material moving into the disposal enclosure 340 when the plunger 329 and sliding seal 318 are advanced. A valve 342 may be provided in the same manner as described above for controlling the flow into the disposal enclosure 340 and discussion of these aspects are also incorporated here.

Referring to FIGS. 3A-3B, the suction source 314 may also include a movable element that is a bellows 350 (rather than the plunger) that may be actuated by foot with a foot pedal. The bellows 350 are biased to an open position so that the bellows 350 provides suction after the foot pedal is depressed. Similar to other embodiments, when the bellows 350 is compressed by the user's foot the material within the bellows 350, which also constitutes part of suction path as described herein, is moved to the disposal enclosure 340.

Figure 4:
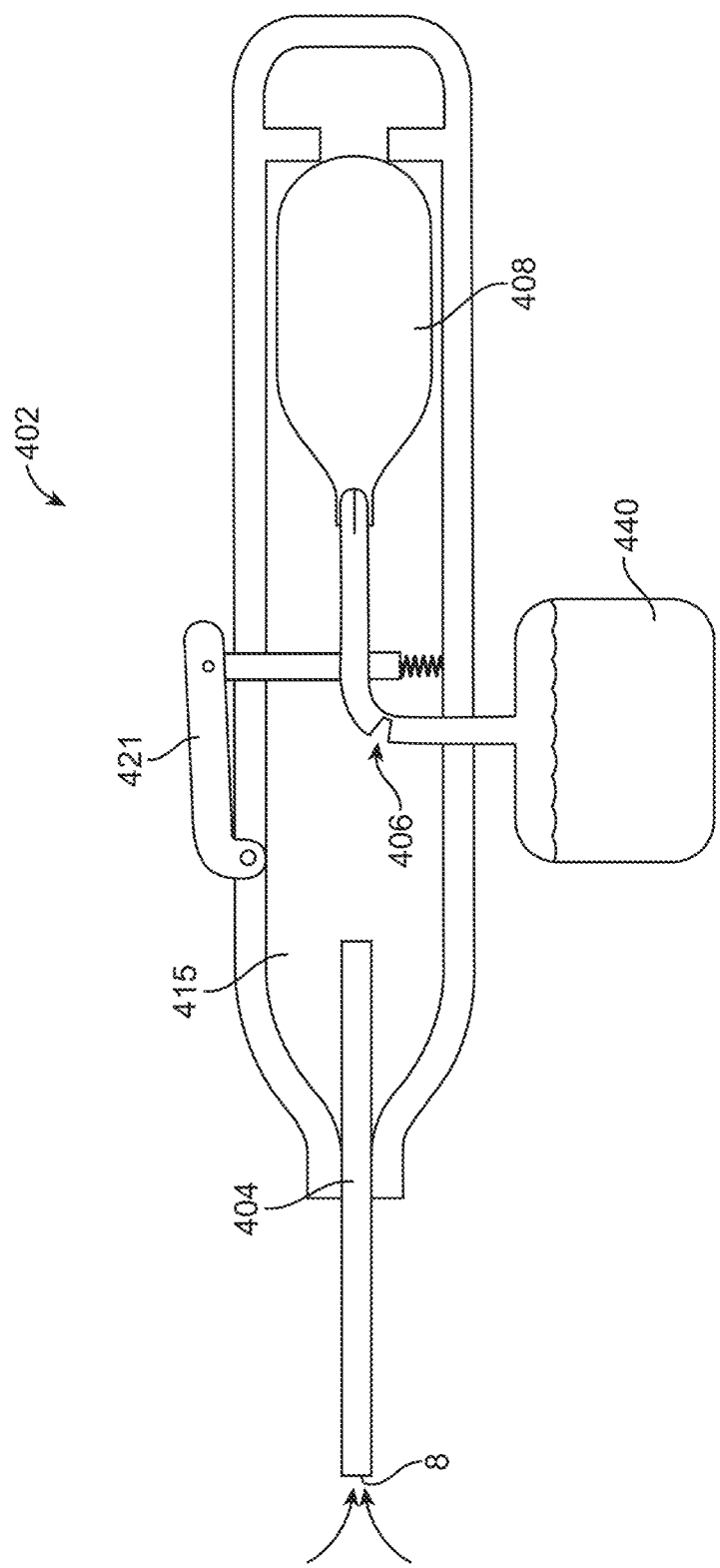
FIG. 4 shows yet another suction device using a venture.

Referring to FIG. 4, yet another suction device 402 is shown wherein the same or similar reference numbers refer to the same or similar structure. The device 402 has a venturi 406 coupled to a source of pressurized gas 408. The venturi 406 directs the pressurized gas toward the disposal enclosure 440 that also directs the material within suction path 404 also toward the disposal enclosure 440. The venturi 406 also acts as the suction source producing suction pressure along the suction path 404. The suction path 404 includes a chamber 415 in communication with the venturi 406 so suction pressure is created in the chamber 415 by the venturi 406. The venturi 406 is opened and closed with a pivoting lever 421.

Figure 5:
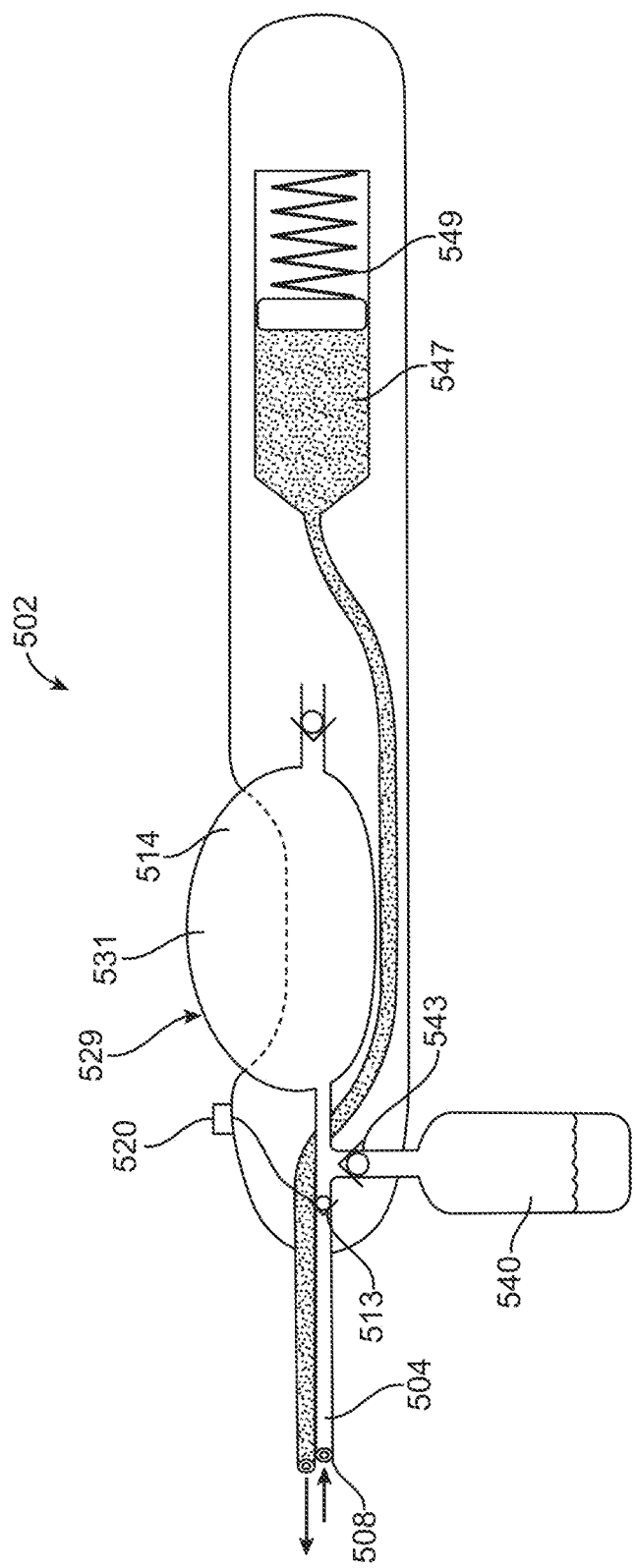
FIG. 5 shows still another suction device having a bladder as the suction source.

Referring to FIG. 5, another suction device 502 is shown wherein the same or similar reference numbers refer to the same or similar structure. The suction source 514 has a movable element 529 that is a bladder 531 configured to be deformed manually by the user. Once compressed, compression is maintained on the bladder 531 to stop suction and reduced to produce suction. Stated another way, the bladder 531 is moved from an unbiased stated to a compressed state with the user releasing compression to begin suctioning material into the opening 508. Movement of the bladder 531 from the unbiased state to the compressed state may also move material from the suction path 504 (which includes the internal volume of the bladder) to the disposal enclosure 540. A first valve 513 may also include an interface 520, such as a button, so that the first valve 513 acts as the actuator described herein and separates a proximal volume (i.e. proximal of the valve 513) from a distal volume (i.e. distal of the valve 513) of the suction path 504. The first valve 513 may be formed over a deformable portion of the suction path 504 along the valve 513 as described herein. A second valve 543 (which may be a one-way valve) regulates flow to the disposal enclosure 540. An irrigation source 547 may also be provided with a spring loaded delivery mechanism 549 coupled to an actuator (not shown).

All aspects and methods of the suction devices described herein are applicable to the other suction devices and all such methods and aspects are expressly incorporated for each from the others. For example, the suction path length and volume as well as dimensions of the lumen and shaft are applicable to each of the other suitable embodiments described herein.

Referring now to FIGS. 6A-6C and FIG. 7, a suction tip 600 is shown for suctioning material from the eye. The suction tip 600, whether removable or integral to the device, can be positioned on a front end of the devices described herein to restrict the material suctioned to a size that reduces issues with clogging. The suction tip 600 can include a shaft 602 with a lumen 604 extending through the shaft 602. A distal opening 608 in the shaft 602 has an area that is defined by an opening axis OA that maximizes a size of the opening 608. The opening area OA may be circular, oval or any other suitable shape. The opening area OA defines an effective diameter defined as the diameter equivalent for a circle having the same area as the opening area. The distal opening 608 in the shaft 602 can be smaller than an inner diameter of the lumen 604 thereby mitigating issues with clogging inside the shaft 602.

Figure 7:
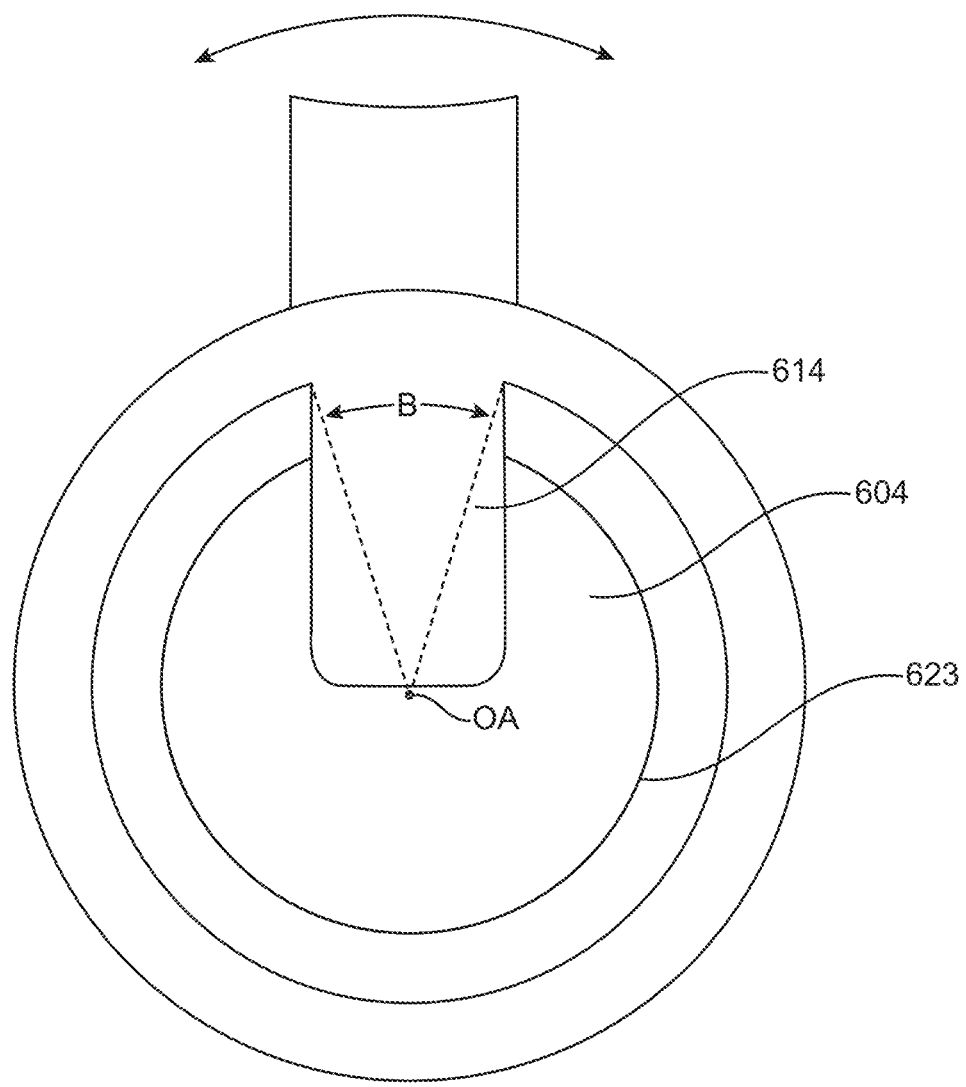
FIG. 7 shows an end view of the flow restrictor.

The suction tip 600 also can include a restrictor 610 that extends over the distal opening 608 when viewed along the opening axis OA. The restrictor 610 has a support arm 612 extending from the shaft 602. The restrictor 610 may have a stop 614 attached to the support arm 612 with the stop 614 spaced apart from the distal opening and positioned over the distal opening when viewed along the opening axis OA as shown in FIG. 7. The restrictor 610 is spaced apart from the distal opening 608 between 0.80 to 1.10 times, or 0.85 to 1.00 times, the effective diameter measured along the opening axis and aligned with the distal opening 608 when viewed along the opening axis OA. The restrictor 610 also may optionally extend a short distance from the distal end of the shaft 602 so that it does not impede use. To this end, the restrictor 610 may have a distal end 615 that extends no more than 1.5 times the effective diameter from the distal opening 608 measured along the opening axis. The restrictor 610 has an area when viewed along the opening axis OA that can be 0.1 to 1.2 times the area of the distal opening 608 when viewed along the opening axis OA. Thus, the restrictor 610 may be somewhat small when less concerned with moving, gathering or clearing material from the opening 608.

The support arm 612 may have an angular extent B when viewed along the opening axis OA of no more than 90 degrees as shown in FIG. 7. The distal opening 608 may be free of obstruction apart from the support arm 612 between the distal opening 608 and a stop 614 on the restrictor 610 when viewed along the opening axis OA. The restrictor 610 forms a feed opening 622 leading to the distal opening 608 when the restrictor 610 is in the working position shown by the dotted-line position of FIG. 6B. The feed opening 622 defines a surface 626 extending between and defined by the restrictor 610 and a distal end of the shaft 623 around the opening 608. The surface 626 may be an elongate surface that, essentially, extends from one side of the support arm 612 to the other. In this manner, an average length of the surface 626 is 2.5-3.5 times the effective diameter. The surface 626 may have a width of 0.8 to 1.1 times the effective diameter.

The support arm 612 may be longitudinally and/or rotatably movable relative to the shaft 602 to adjust a longitudinal or rotational position of the support arm 612 as shown in the dotted-line and solid line positions. The support arm 612 is movable from a working position (as defined above) to a displaced position with the working position being a position used when suctioning material into the distal opening 608. The shaft 602 has a longitudinal axis LA and the restrictor 610 is formed with the support arm 612 rotating and/or longitudinally displaceable. The restrictor 610 may be formed so that the displaced position moves material toward the distal opening 608. The restrictor 610 may also be extended outwardly to help gather or otherwise organize material to be suctioned. The restrictor 610 may be movable to a position that is at least two effective diameters from the distal opening 608 measured along the opening axis OA.

The restrictor 610 can be mounted over the shaft, for example, in a concentric manner although an interlocking or independent lumens are considered herein so long as the restrictor 610 is over the shaft and outside the lumen in some embodiments. The restrictor 610 is movable to a stored position in that the entire restrictor 610 is positioned proximal to the distal opening 608 and optionally completely outside the lumen 604 as shown in the dotted-line position of FIG. 6A. Thus, the user may elect to use the suction device without restriction, for example, when the likelihood of clogging the opening is low. The restrictor 610 may be deformed when in the stored position and, to this end, the restrictor 610 has a living hinge 640 with the support arm 612 forming part, or all, of the living hinge 640 that is deformed in the stored position.

Figure 6A:
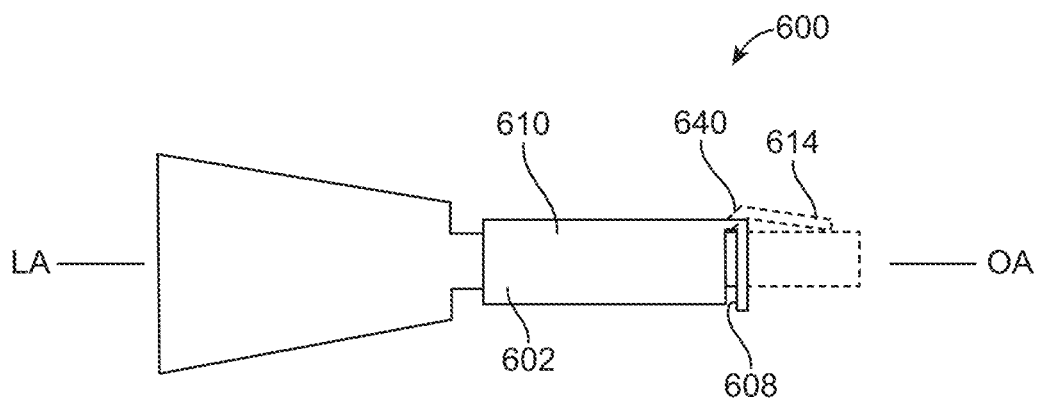
FIG. 6A shows a flow restrictor covering an opening in a shaft and in a stored position in the dotted-line position.
Figure 6B:
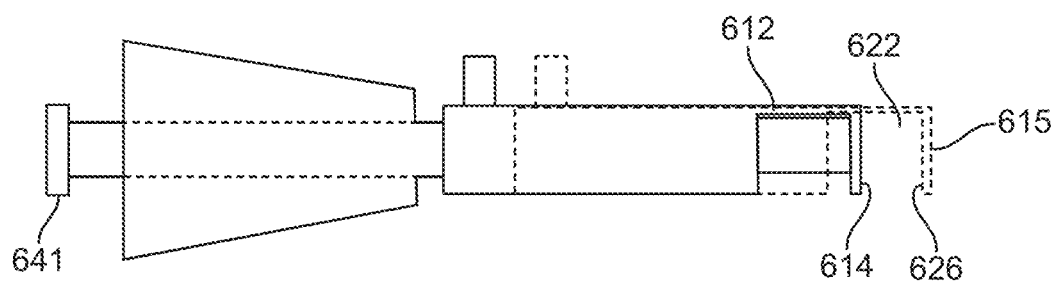
FIG. 6B shows the flow restrictor movable longitudinally relative to the shaft with the dotted line position showing a working position.
Figure 6C:
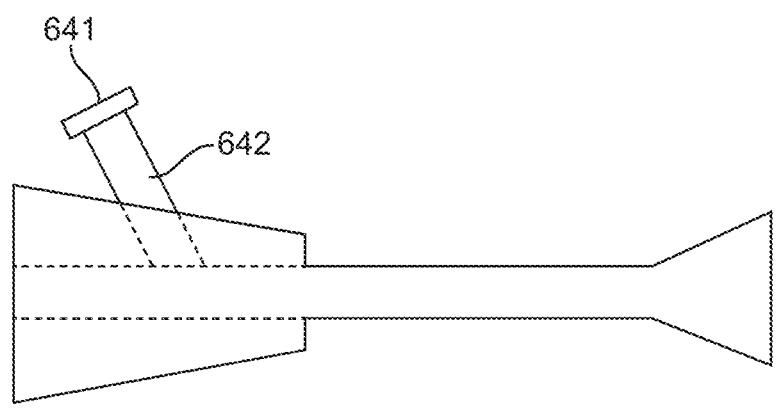
FIG. 6C shows show an alternative shaft having a y-arm.

The stop 614 may be part of the support arm 612 in that the distal end of the support arm 612 simply forms the stop 614. Furthermore, the restrictor 610 may also simply be part of an extension of the shaft. Finally, the restrictor 610 and methods associated with the restrictor 610 may be used with any of the other devices described herein including those associated with cutting and/or removing the lens. Furthermore, the devices may be used through the lumen of any of the devices described herein by simply providing a y-arm 642 and a suitable connector 641 that forms a seal around the cutting device. Thus, the lumen may be a substitute for any lumen described herein and the method of cutting the lens in combination and aspirating material and the device combination including any lens cutting device coupled with any aspirating device being specifically incorporated herein. For example, referring to FIGS. 6B and 6C, a seal is provided at the Y-arm 642 in the lumen and suction path through which any of the cutting devices described herein (or another cutting device) may be introduced. FIG. 6B shows the seal centrally located rather than on a Y-arm so the cutting device extends directly through the lumen with suction in the annular space between the cutting device and the shaft. Furthermore, an irrigation lumen, which may be concentric or separate, may be provided and the process of irrigating may be practiced with any method or combination method described herein and such methods are specifically incorporated here as shown in one or more embodiments and expressly incorporated into those that do not.

In use, the distal end of the shaft is positioned in the eye for any procedure on the eye including cataract surgery. During cataract surgery pieces of the cataract are removed using suction. Material can be suctioned into the distal opening by applying suction that draws material into the distal opening. The restrictor 610 may help to reduce clogging of the distal opening compared to conventional suction devices that permit unrestricted flow toward the distal opening. As mentioned above, a problem with the conventional method is that material that is larger than the suction opening is free to approach and, thus, clog the opening. Suction must be stopped and, if necessary, the material removed independently by another instrument. Described herein are devices that reduce the likelihood of clogging whether by providing the restrictor or other mechanisms as will be described in more detail below. It should be appreciated that devices described herein can be used with any device including a stand-alone aspiration device, a re-usable phacoemulsion tip, or a disposable aspect of any aspiration device.

Figure 8A:
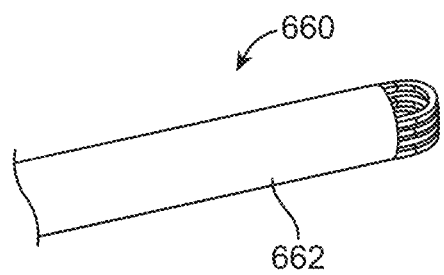
FIG. 8A shows a tissue manipulator in a collapsed position within a lumen of a shaft.
Figure 8B:
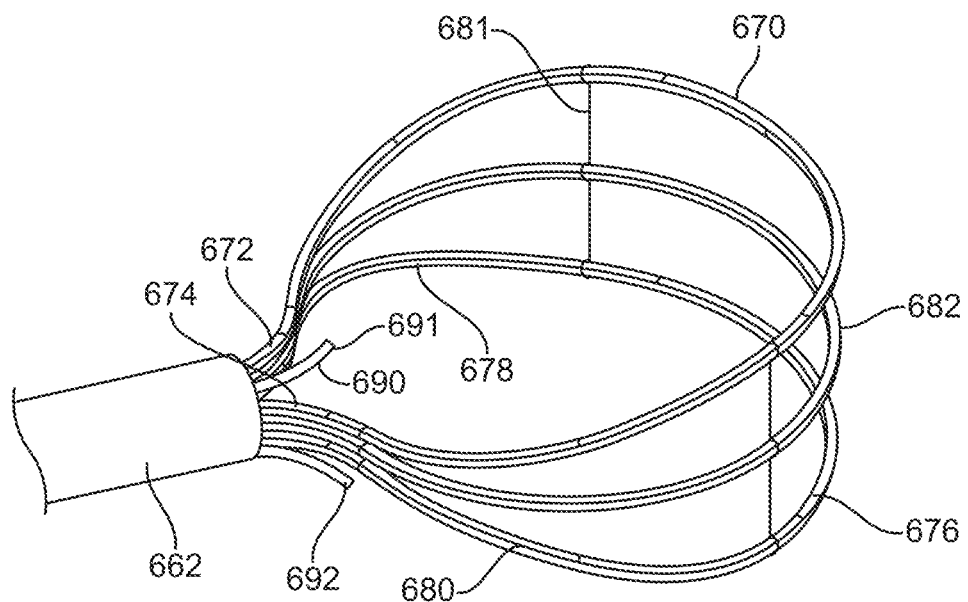
FIG. 8B shows the tissue manipulator expanded with filaments extending between loops.
Figure 8C:
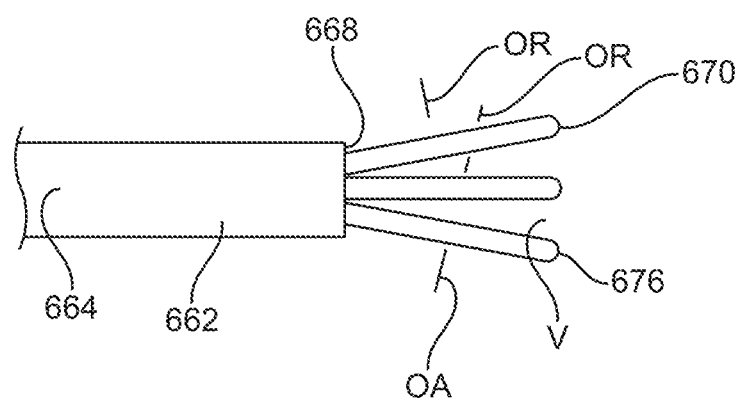
FIG. 8C shows another view of the loops with the filaments removed.

In another aspect, tissue manipulators and method of manipulating tissue are described. The tissue manipulator can be positioned on a separate surgical device or a surgical device incorporating suction as described elsewhere herein. FIGS. 8A-8C illustrate an implementation of a tissue manipulator 660 having a shaft 662 with a lumen 664 and a distal opening 668. A source of suction may be coupled to the lumen 664 with suction being used together with or separately from the tissue manipulator 660. Irrigation may also be supplied with the other shafts incorporated herein and such incorporation is expressly provided here. The tissue manipulator 660 can include a plurality of loops. In some implementations, a first loop 670 has a first leg 672 and a second leg 674 with at least one of the first and second legs 672, 674 extending through the lumen 664. The first loop 670 is movable from a collapsed position of FIG. 8A to an expanded position of FIG. 8B when the first and second legs 672, 674 are advanced through the lumen 664 and out the distal opening 668. A second loop 676 can also have a first leg 678 and a second leg 680 with the first and second legs

678, 680 extending through the lumen 664. The second loop 676 is also movable from a collapsed position to an expanded position when the first and second legs are advanced through the lumen and out the distal opening 668. The shaft 662 may be sized for introduction of a distal end of the shaft into an eye.

The first loop 670 may have an unbiased shape that bounds an area defined in an orientation OR that maximizes the area. The area has an effective diameter that is equal to the diameter of a circle having the same area. The first loop 670 moves toward the unbiased shape when moving from the collapsed position to the expanded position. The effective diameter of the area of the first loop 670 can be 4.5 mm to 6.5 mm or can be 5.0 mm to 6.0 mm. The effective diameter of the unbiased shape of the first and/or second loops 670, 676 may be within 20% of an effective diameter of the expanded position of the first and/or second loops 670, 676, respectively. In this manner, the first and/or second loops 670, 676 provide for a soft deployment and are flexible during use. Use of a superelastic material further enhances the flexibility of the first and second loops 670, 676. To this end, the first and second loops 670, 676 may be formed of superelastic wire having a diameter of about 0.003" to about 0.006" although any size may be used with any suitable cross-sectional shape.

The first and second loops 670, 676 are each defined by the orientation OA that maximizes an area of the first loop 670 and second loop 676 when in the expanded position when viewed along each orientation. The orientation of the first and/or second loop 670, 676 may be within 45 degrees of perpendicular to the longitudinal axis LA at a distal end of the shaft 662. The first loop 670 can be spaced apart from the second loop 676 to define a volume V therebetween when the first and second loops 670, 676 are in the expanded position with the volume therebetween being 48-84 mm³. As will be described in more detail below, the plurality of loops of the tissue manipulator 660 can be spaced apart from one another during expansion of the loops or in a separate step following expansion of the loops.

Figure 9:
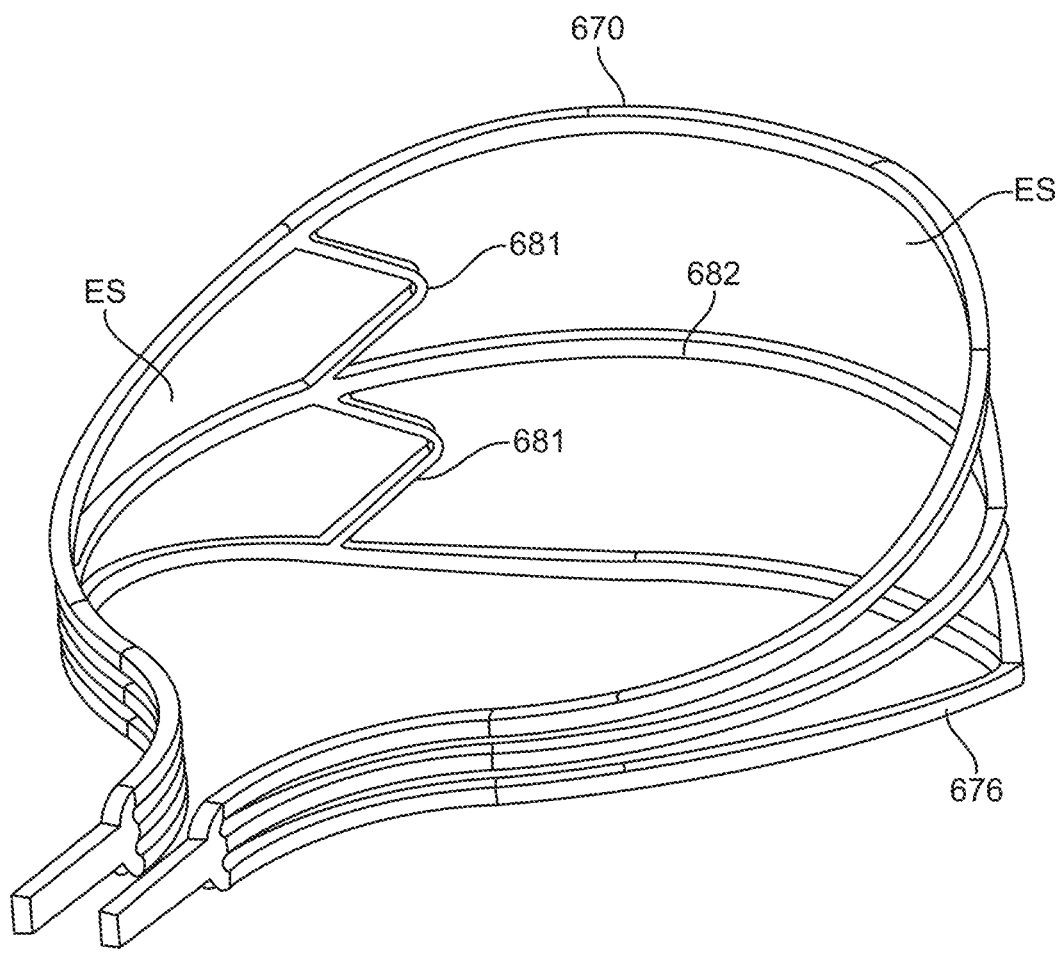
FIG. 9 shows another tissue manipulator with integrally formed intermediate elements.
Figure 10:
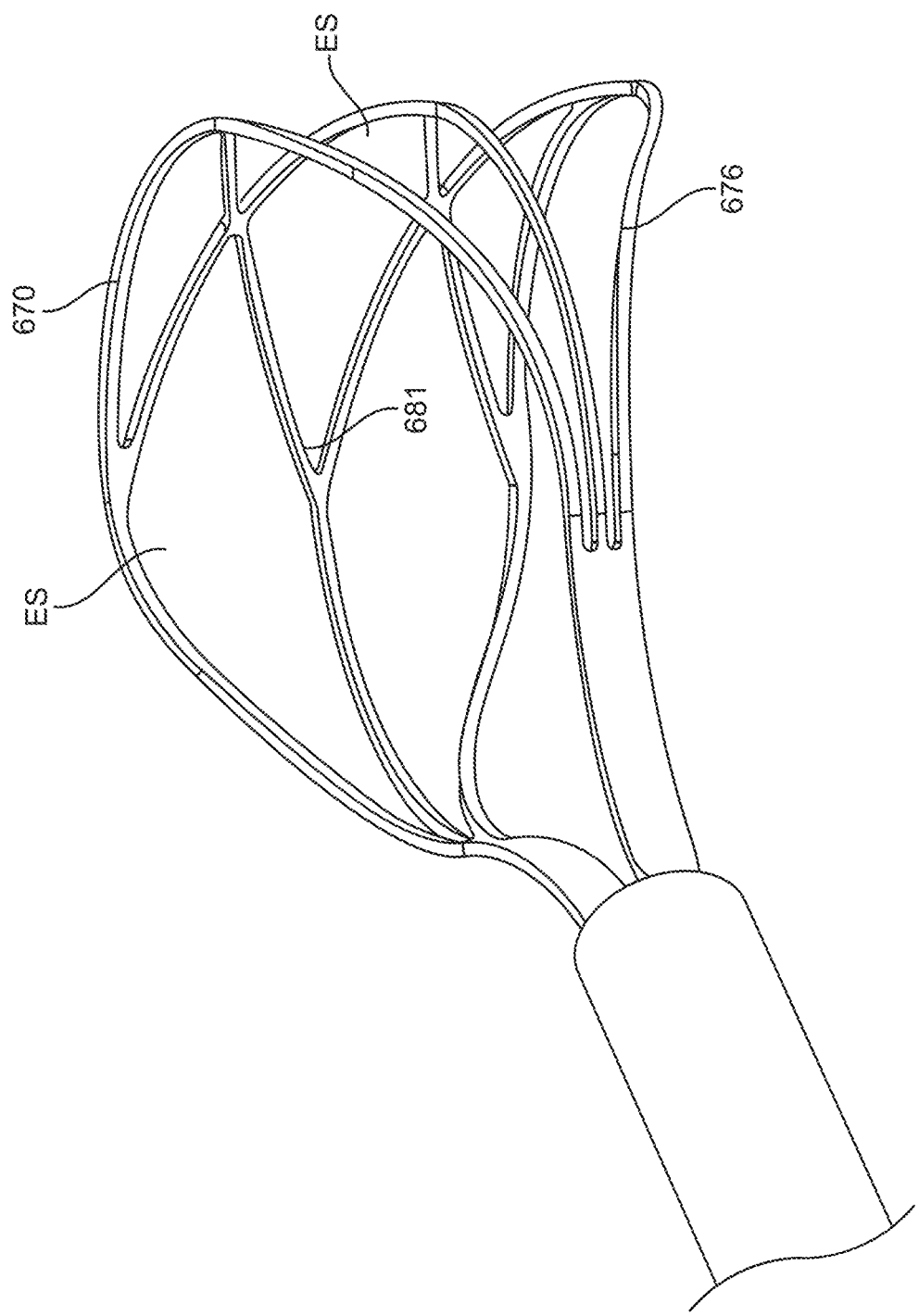
FIG. 10 shows another tissue manipulator with integrally formed intermediate elements.

The tissue manipulator 660 may also include an intermediate element or third loop 682 positioned between the first loop 670 and the second loop 676. The intermediate element 682 may include an interconnecting element 681 extending between the first loop 670 and the second loop 676. The interconnecting element 681 may be integrally formed elements with the first loop 670 and the second loop 676 as shown in FIGS. 9 and 10. Alternatively, the interconnecting element 681 may be a flexible filament extending between the first loop 670 and the second loop 676 as shown in FIG. 8B. The third loop 682 may have the features of the first 670 and second loops 676. The orientation OA that maximizes an area of the third loop 682 may be within 30 degrees of perpendicular to the longitudinal axis LA.

The first and second loops 670, 676 provide a controlled amount of exposed surface therebetween to control, and optionally cut, a controlled amount of the material. The exposed surface ES between the first loop 670 and the second loop 676 has an area of 15 mm² to 60 mm². Stated another way, the exposed surface between the first loop 670 and the second loop 676 is 3-10 times the effective diameter in the expanded position (or the unbiased position since they may be the same).

The exposed surface between the first loop 670 and the second loop 676 may have 2-8, 2-6, 2-4 or even just 2 independent cells when viewed in a radially inward direction relative to the orientation axis of the first and second loops 670, 676. The exposed surface ES has an area that is at least 4 times larger than an area of the intermediate element 682 positioned between the first loop 670 and the second loop 676 when the exposed surface ES is viewed radially inward with respect to the first and second loops 670, 676. In this manner, the intermediate element 682 does not take up an excessive amount of room as compared to some net-type devices.

The first loop 670 may also be formed so that at least 80% of the loop is 1.5-3.5 mm from the second loop 676. The first and second loops 670, 676 (and optional intermediate element 682) may also be configured to cut material contained within therein when collapsed.

Again with respect to FIG. 8B, the device 660 may include a first support element 690 extending from a distal end of the shaft when the first loop 670 is in the expanded position. The first support element 690 may be an elongate element that extends to a free end 691. The first support element 690 is positioned with the free end 691 positioned within an area of the first loop 670 when viewing the first loop along the orientation OA that maximizes the area of the first loop 670. The first loop 670 has an effective diameter when in the expanded position while the first support element 690 extends into the area of the first loop 670 so that the free end 691 is positioned 0.05 to 0.30 times the effective diameter of the first loop 670 within the first loop 670 when viewed along the orientation OA. A second support element 692 cooperating with the second loop 676 in the same manner may also be provided.

Referring to FIG. 11, the first loop 670 and/or second loop 676 may have at least one interconnecting element 695 extending from a first connection 696 on the loop to a second connection 697 on the same loop or the loop(s) may be substantially free of any such interconnecting elements depending upon the desired use. For example, a net-like material as shown in FIG. 11 may be provided or the loops may be free of interconnecting elements so that the open area is free. All discussion and limitation of the first loop 670 are applicable to the first loop 670, the second loop 676 and the third loop 682 as well as discussion of the first support 690 applicable to the second support 692. The first support 690 may extend independently or simultaneously with the first loop 670. The first support 690 helps to secure material within the first loop 670 by extending into the opening area formed by the loop.

The first and second legs of the first and second loop(s) may be movable within the lumen. Alternatively, the first leg 672 and the second leg 674 of the first loop 670 are coupled to an actuator extending through the lumen so that movement of the actuator moves the first leg 672 and the second leg 674 between the collapsed position and the expanded position. The first leg 678 and the second leg 680 of the second loop 676 are coupled to an actuator extending through the lumen so that movement of the actuator moves the first leg 678 and the second leg 680 between the collapsed position and the expanded position. The first loop 670 and/or the second loop 676 may be positioned entirely distal to the distal opening in the expanded position. The first loop 670 and the second loop 676 may include a superelastic material within a superelastic range when in the collapsed position.

Referring to FIG. 12, a tissue manipulator 700 can have a concave element 702 coupled to a first loop 704 to form a basket 706 to receive material. The concave element 702 may have one end 708 integrally formed with the first loop 704 with the other end 710 movable within a lumen 712 of a shaft 713 independent of a first leg 714 and a second leg 716 of the first loop 704. Cross-elements 715 are also integrally formed with the first loop 704 and may also be integrally formed with the concave element 702. Alternatively, both ends 708, 710 may be integrally formed with the loop 704.

Figure 13:
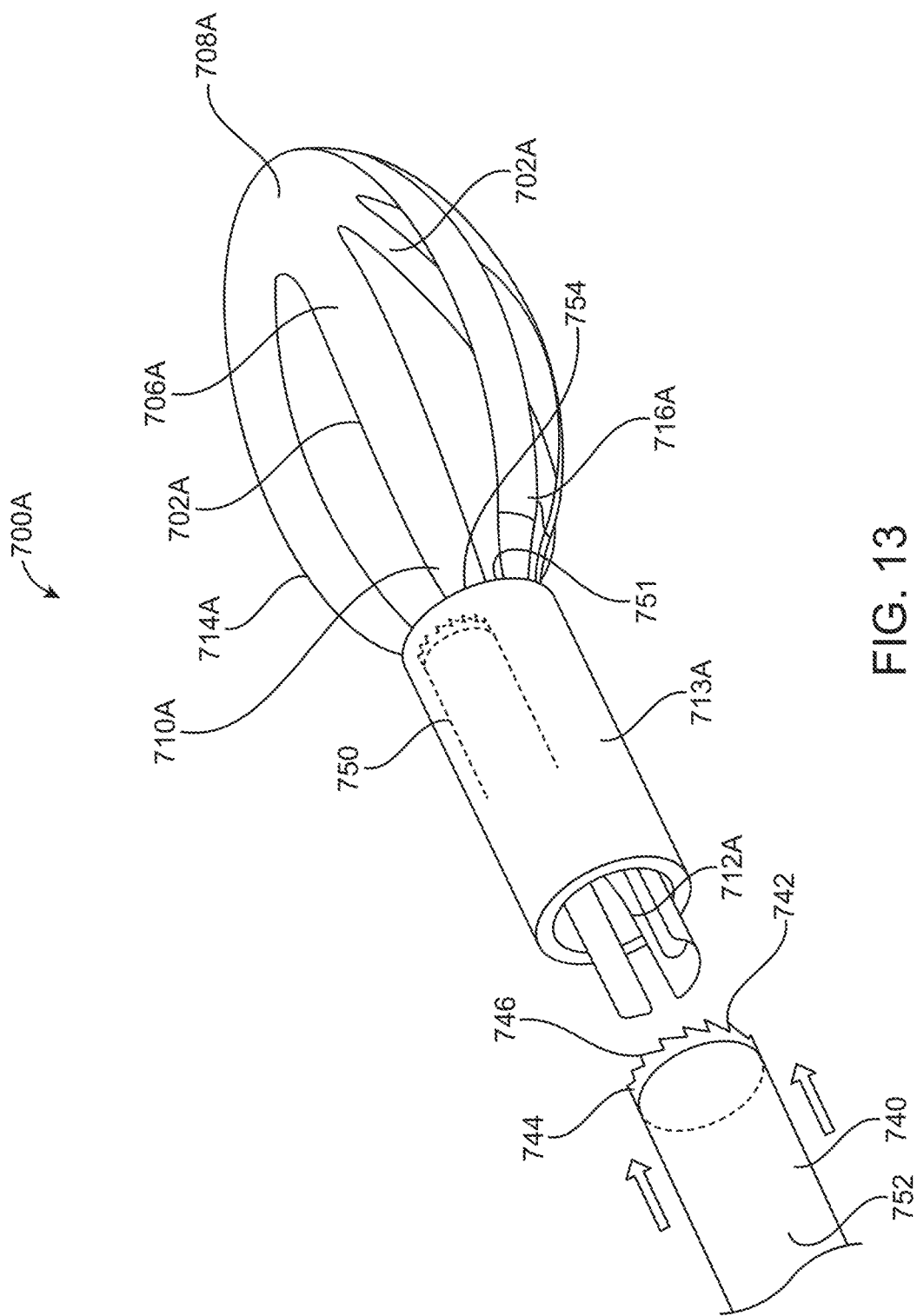
FIG. 13 shows still another tissue manipulator with a rotating cutter.
Figure 14:
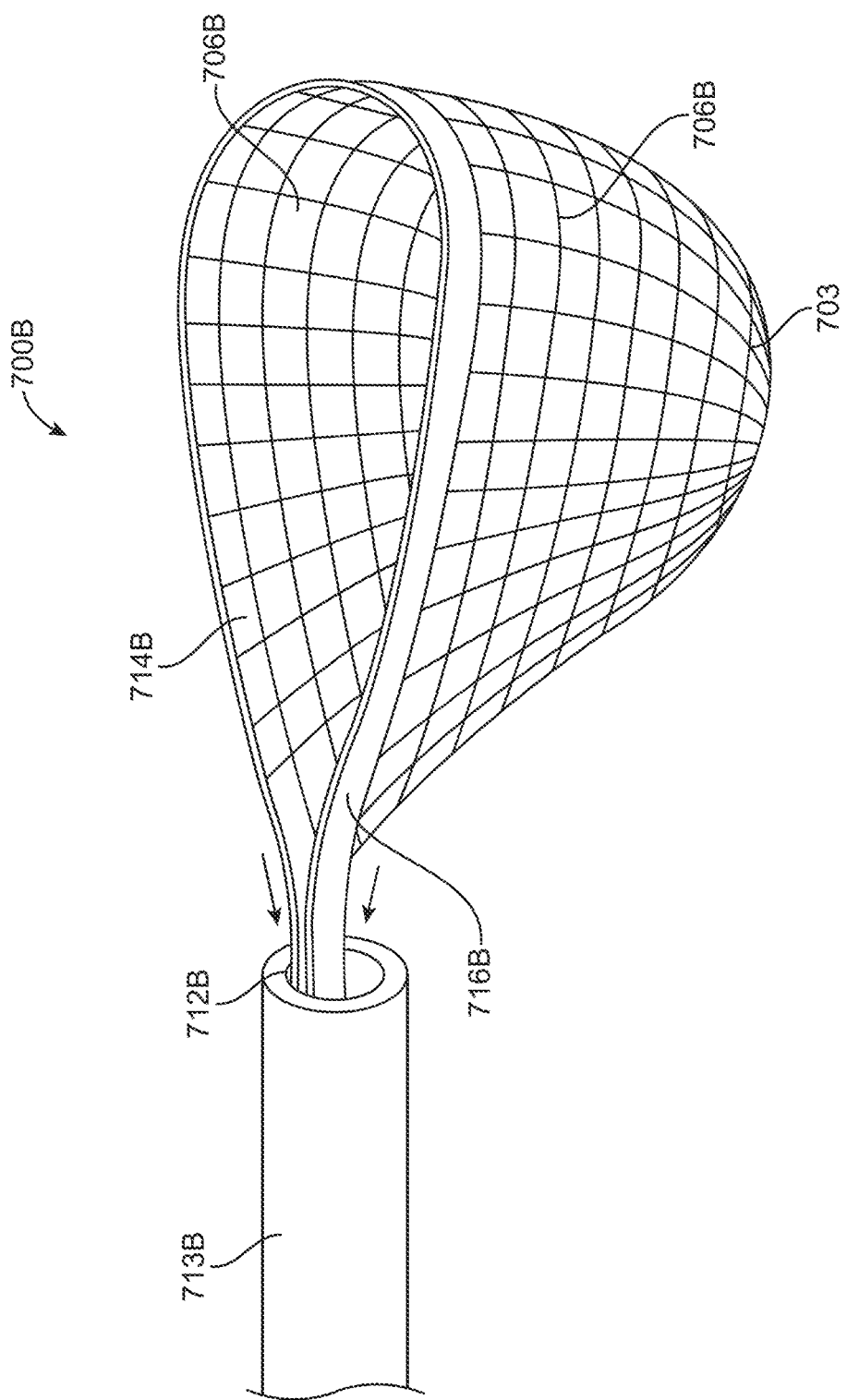
FIG. 14 shows another tissue manipulator with a net-like material.

Another tissue manipulator 700A is shown in FIG. 13 wherein the same reference numbers refer to the same or similar structure. A concave element 702A, which may be 2-3 concave elements 702A. The manipulator 700A has a first loop 704A with a first leg 714A and second leg 716A. A first end 708a of the concave element 702A may be integrally formed with the loop 704A while the second end 710A may be independently movable within a lumen 712A. The loop 704A and the concave element 702A may be made of ribbon-shaped material having a width to thickness ratio of more than 3 to 1 to create a more closed basket 706A compared to wire having a 1 to 1 ratio. Referring to FIG. 14, another tissue manipulator 700B is shown wherein the same or similar reference number refer to the same or similar structure. The manipulator 700B has a first loop 704B with a concave element 702B being a net 703. The net 703 may be integrally formed or a separate element attached to the loop 704B.

Figure 15:
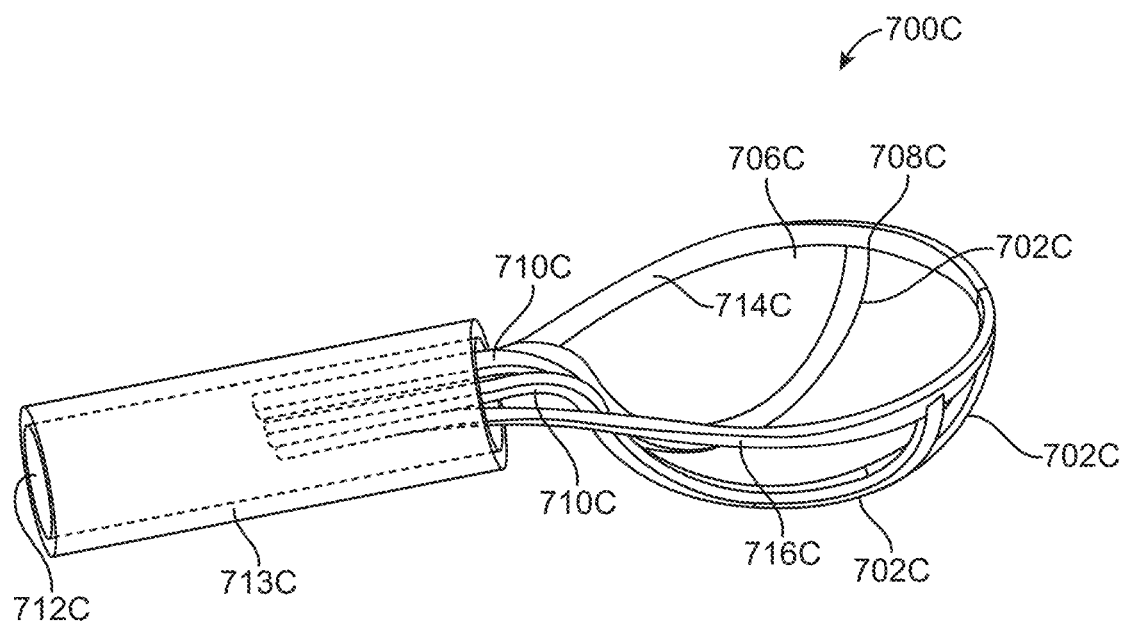
FIG. 15 shows still another tissue manipulator.

Referring to FIG. 15, another tissue manipulator 700C is shown wherein the same or similar reference number refer to the same or similar structure. The manipulator 700C has a first loop 704C with a concave element 702C, which may be 2-3 concave elements 702C, integrally formed at first end 708C and may have a second end 710C independently movable within a lumen 712C within shaft 713C or a separate element attached to the loop 704C. The manipulator 700C is free of interconnecting elements between any two sides of the loop and may also include no interconnecting elements between the concave elements 702C.

Figure 16:
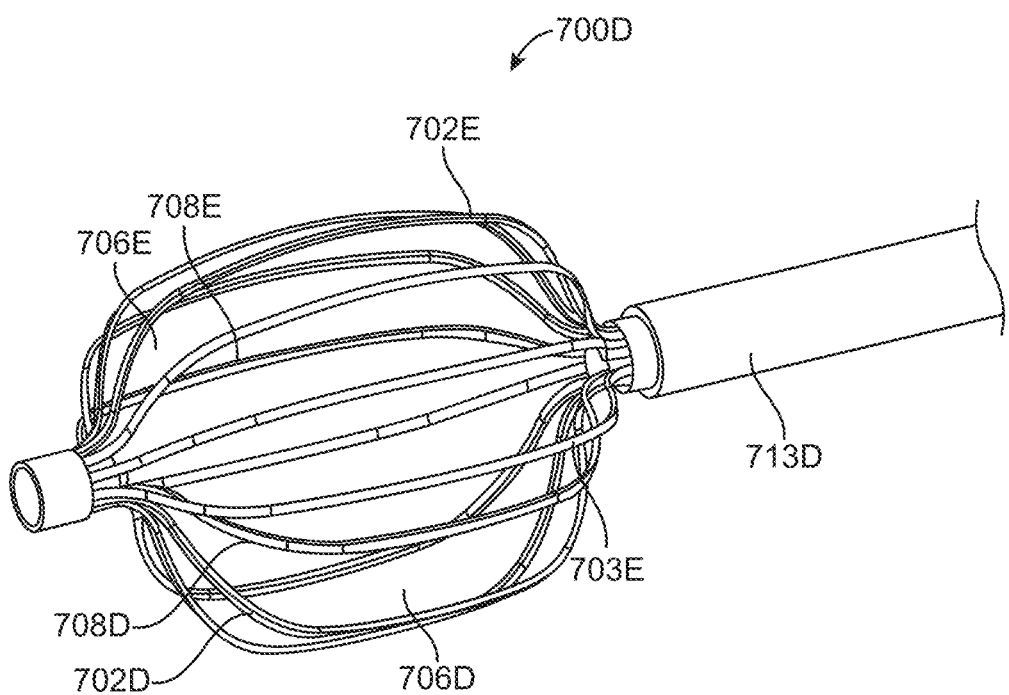
FIG. 16 shows a tissue manipulator having two opposing baskets.
Figure 17:
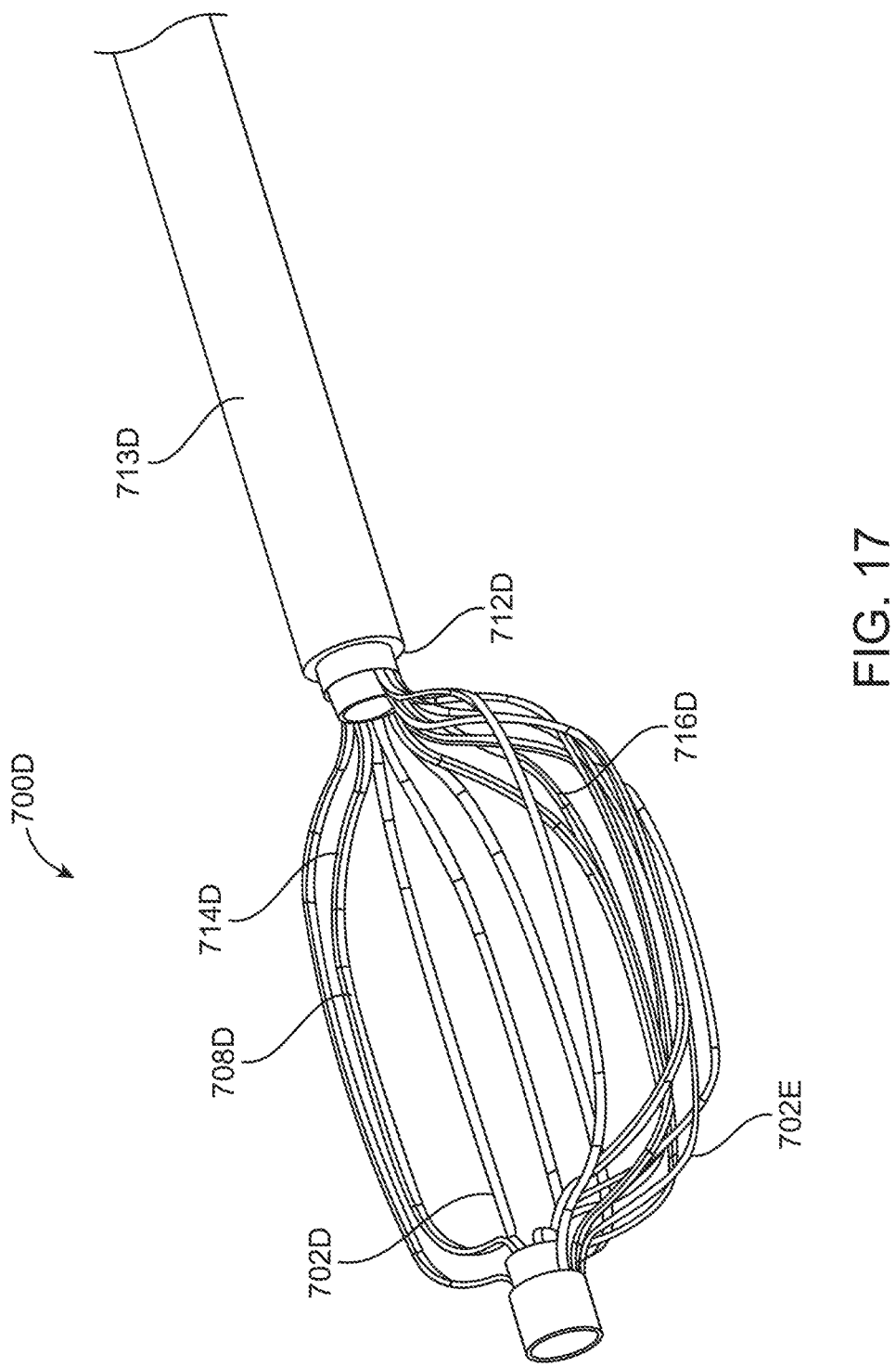
FIG. 17 shows the opposing baskets in a nested position.

Referring to FIGS. 16 and 17, another tissue manipulator 700D is shown in FIG. 16 wherein the same reference numbers refer to the same or similar structure. The tissue manipulator 700D has a first loop 708D and a second loop 708E with corresponding concave elements 702D and 702E, respectively. A first basket 706D and a second basket 706E are movable between a nested position of FIG. 17 and a position in which the two baskets oppose one another as shown in FIG. 16.

Referring again with respect to FIG. 12, the tissue manipulator 700 is described further and it is understood that all aspects described here are applicable to all of the other tissue manipulators 700A-700D and are expressly incorporated for each. The loop 704 has an unbiased shape that bounds an area defined in an orientation OA that maximizes the area. The area has an effective diameter that is equal to the diameter of a circle having the same area. The first loop 704 moves toward the unbiased shape when moving from the collapsed position to the expanded position. The first loop 704 may have effective diameter of 4.5 mm to 6.5 mm or 5.0 mm to 6.0 mm. It should be appreciated that other sized are considered herein. As used herein, the "area" of the loop is determined by the orientation OA that maximizes the area. The first loop is expanded with the first loop orientation being within 45 degrees of perpendicular to a longitudinal axis LA at a distal end of the shaft 713.

Referring again to FIG. 13, a rotating cutter 740 is shown that may be used with any of the device and methods described herein. The rotating cutter 740 has a cutting element 742 at a distal end 744 that may be a series of teeth 746, a sharpened edge, ridges spikes or any other suitable shape. Rotating as used herein may mean rotation in one direction and then back in the other without departing from the scope of the invention. The rotating cutter 740 may be independently positioned and moved for use as desired or may be fixed in a working position shown by dotted-line working position 750. The rotating cutter 740 can be recessed from the distal end 751 of the shaft 713A when in the working position 750 so that the rotating cutter 740 is not exposed from an opening 754 at the distal end of the shaft 713A. The tissue manipulating devices described herein may be used to push, draw, squeeze or otherwise manipulate tissue into engagement with the rotating cutter 740. The rotating cutter 740 may further have a suction lumen 752 therein for suctioning material.

Referring now to FIGS. 18A-18D and FIG. 19, a cutting device 800 for cutting material in the eye and, in a specific application, for cutting a whole lens while contained within a capsular bag is shown. The cutting device 800 has a shaft 802 with a first shaft part 804 and a second shaft part 806 that are movable relative to one another between a first position of FIG. 18A and a second position of FIG. 19. An elongate element 808 has a first end 810 coupled to the first shaft part 804 and a second end 812 coupled to the second shaft part 806. The cutting device 800 forms a loop 814 with at least part of the elongate element 808 forming the loop 814 together with the shaft 802. The loop 814 moves from a collapsed position of FIG. 18A to an expanded position of FIG. 19 when the first and second shaft parts 804, 806 move from the first position to the second position. The loop 814 may be expanded to advance the loop 814 between the capsular bag and the whole lens. Material is positioned in an open area 813 of the loop 814 and then cut by collapsing the loop 804.

Figure 18A:
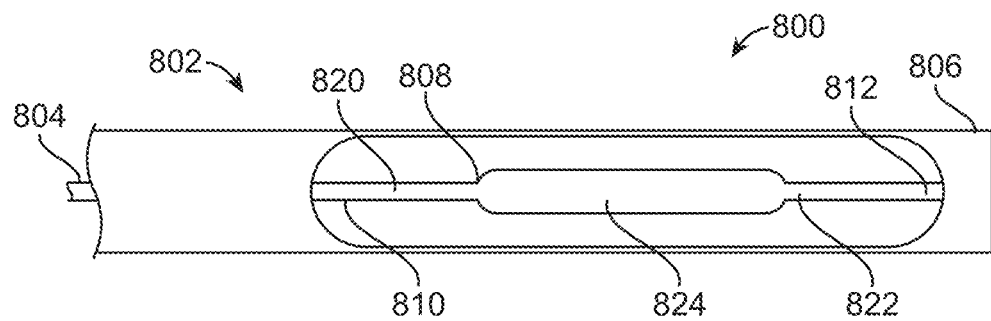
FIG. 18A shows a device for cutting material within the eye.
Figure 18B:
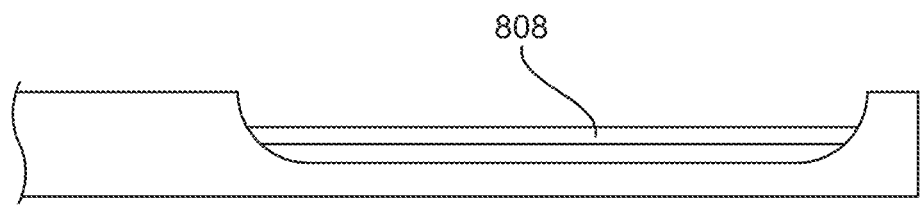
FIG. 18B shows a side view of the device of FIG. 18A.
Figure 18C:
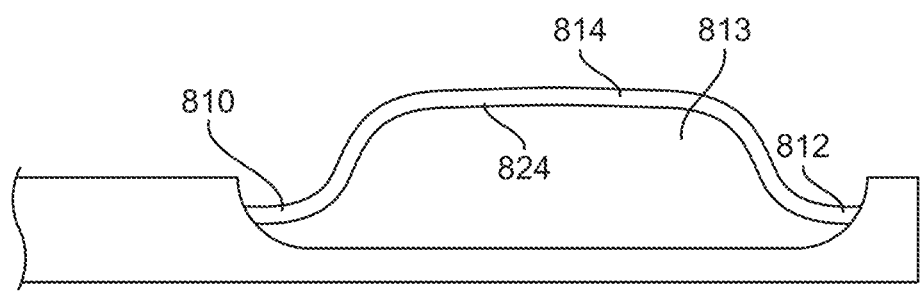
FIG. 18C shows the device of FIG. 18A with an elongate element deformed to expand a loop formed by the device.
Figure 18D:
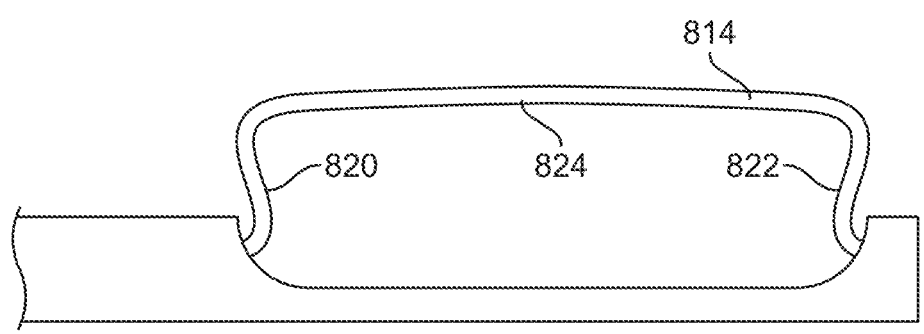
FIG. 18D shows the device of FIG. 18C further expanded.

The elongate element 808 expands in a manner that facilitates cutting the whole lens within the capsular bag. The elongate element 808 may have a first flexible portion 820 and optionally a second flexible portion 822 with an intermediate portion 824 therebetween. The elongate element 808 initially expands laterally outward as shown in FIG. 18C. When the first and second flexible portions 820, 822 begin to bend, the loop 814 has a proximal portion 826 and a distal portion 828 that extend proximally and distally, respectively, from the intermediate portion 824. The flexible portion may be at least 1.5× stiffer in bending than the intermediate portion 824. Furthermore, the elongate element 808 may be in an unbiased position when collapsed as shown in FIG. 18A with the elongate element 808 being deformed to deflect and expand the loop. The elongate element 808 may also have a preset shape that facilitates movement to the expanded position while requiring less force to deform the elongate element 808.

Figure 19:
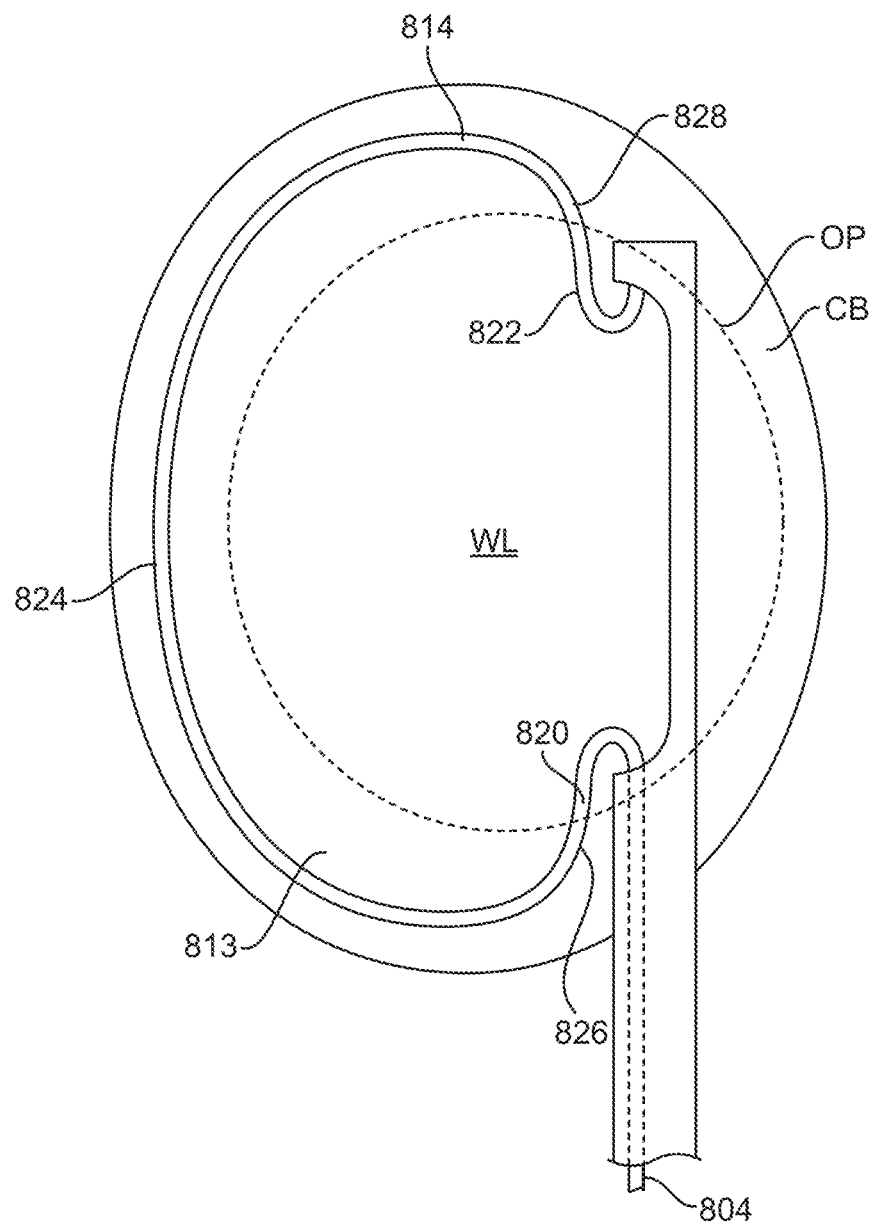
FIG. 19 shows the device of FIGS. 18A-18D full expanded and positioned within a capsular bag and advanced between the capsular bag and the lens when the loop is expanded.
Figure 20A:
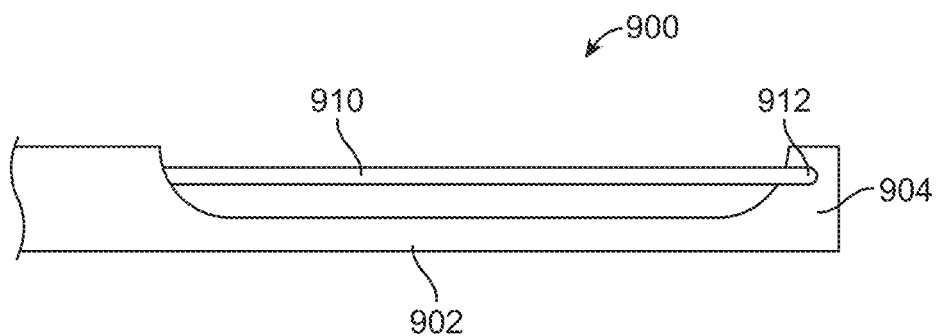
FIG. 20A shows another cutting device in a collapsed position.
Figure 20B:
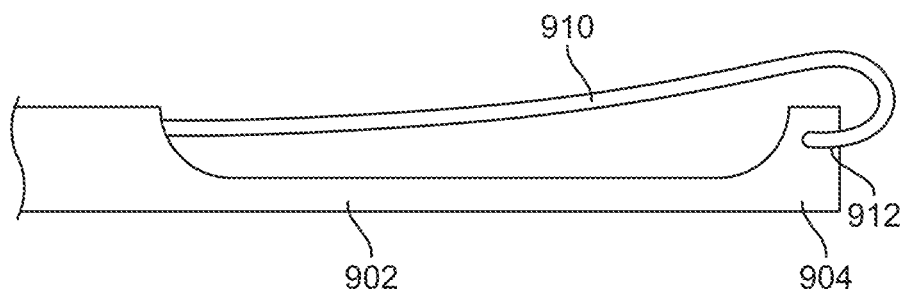
FIG. 20B shows the device of FIG. 20A partially expanded with the distal end changing orientation with respect to the proximal end of the shaft.
Figure 20C:
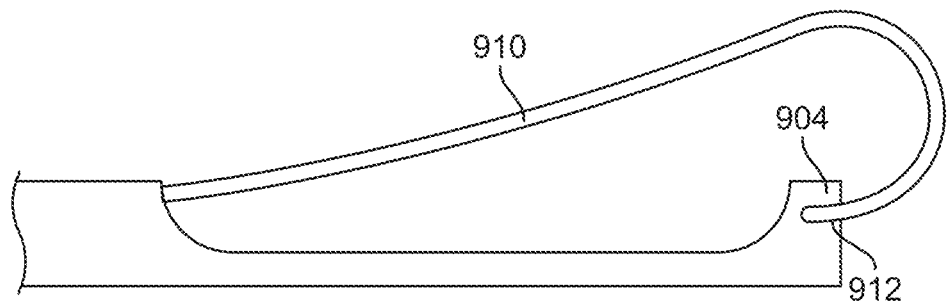
FIG. 20C shows a loop formed by the device advancing distally.

Referring now to FIGS. 20A-20C and FIGS. 21A-21B, another cutting device 900 is shown for cutting material in the eye and, in a specific application, for cutting a whole lens WL within a capsular bag CB through an opening OP (such as a capsulorhexis) that exposes an anterior surface of the lens (see FIG. 19). A shaft 902 has a first shaft part 904 and a second shaft part 906 movable relative to one another between the position of FIG. 20A and FIG. 20B so that a loop 908 formed by the device 900 moves from a collapsed position to an expanded position. An elongate element 910 has a first end 912 coupled to the first shaft part 904 and a second end 914 coupled to the second shaft part 906. The loop 908 is formed at least in part by the elongate element 910 with the loop 908 also being formed by a portion of the shaft 902.

Figure 21A:
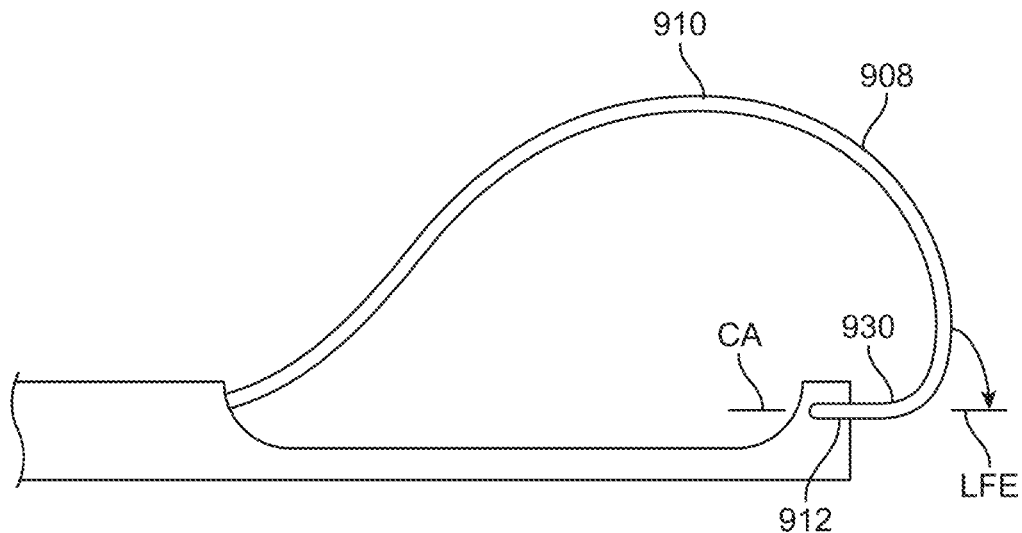
FIG. 21A shows the loop expanded further.
Figure 21B:
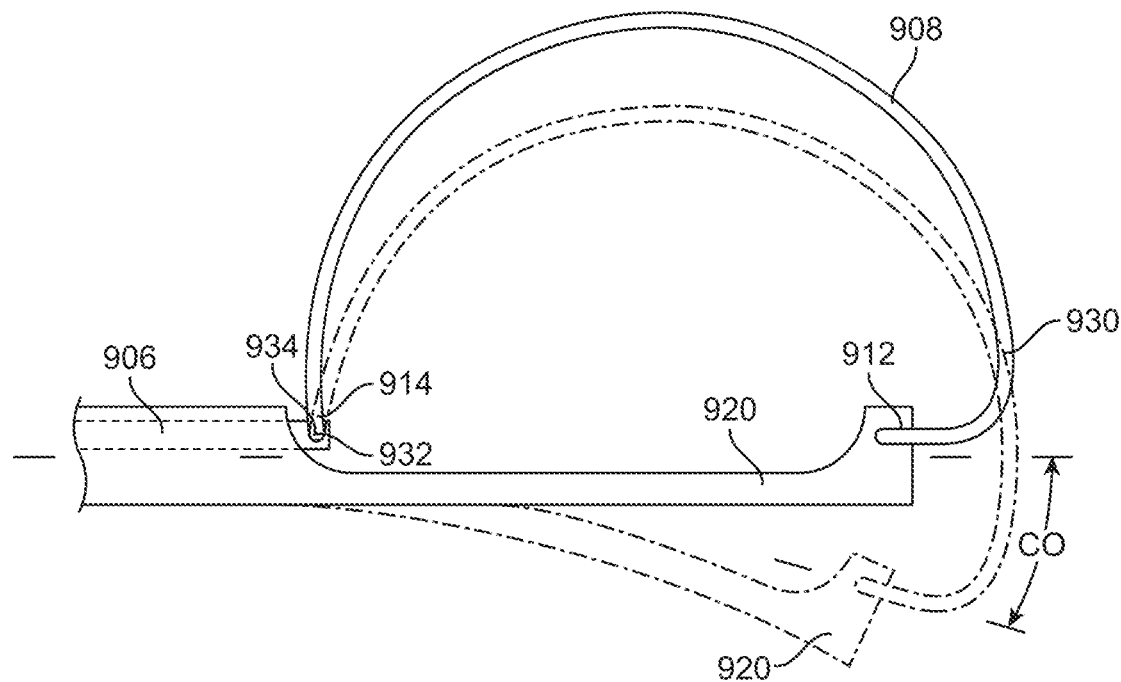
FIG. 21B shows the loop expanded with the proximal end of the elongate element also changing orientation with respect to the shaft.

The loop 908 is expanded so that the first end 912 has a longitudinal orientation LFE that changes by an angle CA at least 120 degrees with respect to the shaft 902 adjacent to the second end 914 of the elongate element 910 when the first and second shaft parts 904, 906 move from the first position to the second position. FIG. 21A shows the angle CA being about 180 degrees.

The 902 shaft may also include a flexible distal end 920 with the first end 912 of the elongate element 910 coupled to the flexible distal end 920 of the shaft 902. The flexible distal end 920 of the shaft 902 may contribute to the changing orientation of the first end 912 with respect to the longitudinal orientation of the shaft 902 adjacent the second end 914. The flexible distal end 920 may change in orientation by an angle CO of at least 30 degrees when the first and second shaft parts move from the first position to the second position.

The first end 912 of the elongate element 910 may be have a pinned connection so that the first end 912 rotates relative to the first shaft part 904 for an angle of at least 120 degrees and may be for 180 degrees+/−45 degrees when the first and second shaft parts move from the first position to the second position. The loop 908 has a distal portion 930 that advances distally beyond a distal end of the shaft 902 as the loop 908 moves from the collapsed position to the expanded position. The first end 912 of the elongate element changes orientation so that the loop 908 advances distally beyond a distal end of the shaft 902 as the loop 908 moves from the collapsed position to the expanded position. The second end 914 may also have a rotatable connection 932, such as a pinned connection 934, to the second shaft part 906. The second end 914 may rotate and change in orientation relative to the shaft adjacent the second end by 90 degrees+/−45 degrees when the first and second shaft parts 904, 906 move from the first position to the second position. The elongate element 912 may be in an unbiased position in FIG. 20A with the elongate element 912 deformed into the positions of FIG. 21A and FIG. 21B. Of course, the elongate element 912 may also have a preset shape similar to FIG. 21B.

Referring to FIGS. 22A, 22B, 23A, and 23B, another device 940 is shown for aspirating material from the eye. As will be described in more detail below, the device 940 is configured to apply pulsed vacuum and optionally pulsed vacuum with a short regurgitation in between pulses. This pulsed vacuum configuration allows for full vacuum pressure to be applied through larger aspiration lumen diameters without causing anterior chamber collapse. Thus, full vacuum can be applied, but the vacuum is applied in short pulses, for example, by valving. All methods and physical characteristics of the other aspiration devices described herein are equally applicable to the device 940 and all such uses and characteristics are expressly incorporated here. For example, the volume of the suction path, the size of the lumen and the distal suction volume and methods of use are all expressly incorporated here.

The device 940 may include a hand-held unit 960 having an elongate shaft 961 coupled to and extending from a housing 962 of the hand-held unit 960. A lumen 963 extends through the shaft 961 to an opening 964 at a distal end 965. The lumen 963 defines part of a suction path 966 extending from a suction source to the opening 964. The suction path 966 defines a suction volume under the influence of the suction pressure by the suction source and a distal suction volume 967. The suction source can be within, on, or attached to the hand-held unit 960.

Figure 22A:
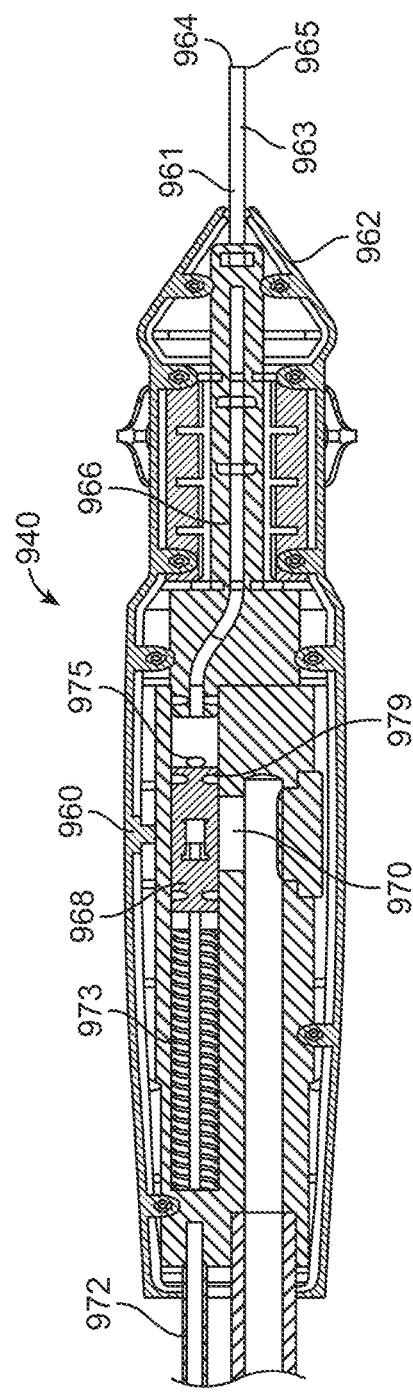
FIG. 22A shows another device for aspirating material from an eye with a valve along the suction path in a closed position.
Figure 22B:
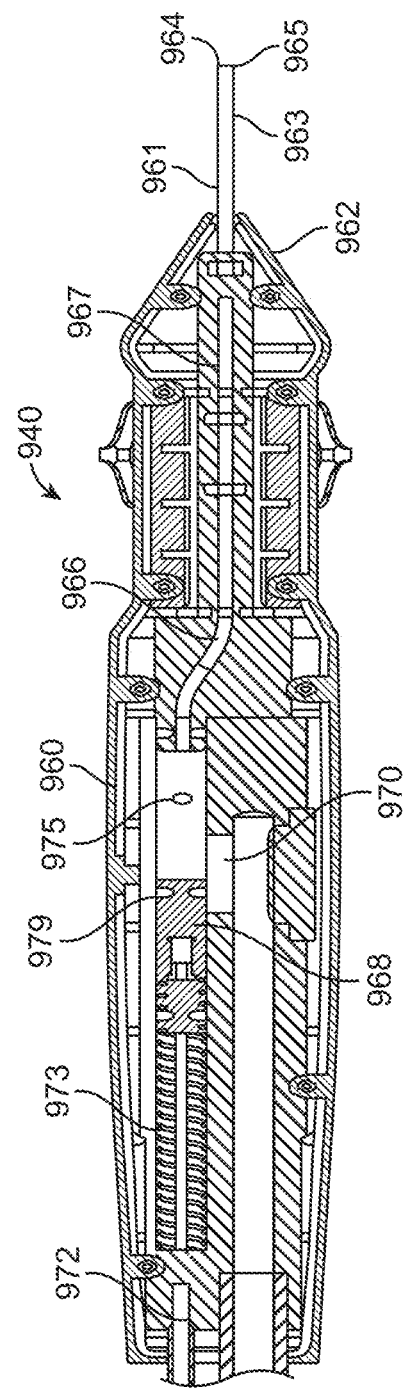
FIG. 22B shows the device of FIG. 22A with the valve in an open position.

The device 940 has a valve 968 coupled to the hand-held unit 960 and positioned along the suction path 966. The valve 968 is movable from a closed position of FIG. 22A, which blocks the suction path 966, to a fully open position, which defines a largest suction path provided by the valve 968. FIG. 22B shows the valve partially open. The valve 968 may also be positioned in any position between the closed and fully open positions as described below. The valve 968 is movable relative to an aperture 970 that is opened and closed by the valve 968 to open and close the suction path 966. The valve 968 can be a movable element 971 coupled to a wire 972 that is used to move and position the valve 968. A spring 973 acts on the valve 968 to bias the valve 968 closed.

The wire 972 can be coupled to an actuator 942 shown in FIGS. 23A and 23B that is configured to displace and position the valve 968. The actuator 942 may include a foot pedal 944 for use as described below. Any other suitable actuator 942 may be used as well. For example, the actuator 942 can be positioned on the hand-held unit 960 or the actuator can be remote from the hand-held unit 960. The foot pedal 944 can be in an off or resting position in that no suction is supplied as shown in FIG. 23A. The foot pedal 944 has a first pivot 945 that is coupled to support mounted to a base 947. The foot pedal 944 has a second pivot 948 that is located near first end 949 of a linkage 950 and may also include a dampener (not shown) to dampen motion of the foot pedal 944. A second end 951 of the linkage 950 has a pivot 939 and may include a sensor 941 that indicates the position of the foot pedal 944. As the foot pedal 944 is depressed, the amount of displacement may be measured in any suitable manner such as the rotational position sensor 941. The second end 951 of the linkage 950 can be attached to a support sled 946 that is slideable relative to the base 947.

The actuator 942 can have a motor 956 that drives a connecting arm 957 coupled to a slider 958. The slider 958 is coupled to the wire 972 (see FIGS. 23A and 23B) so that control of the motor 956 controls the position of the valve 968. The actuator 942 is also coupled to the source of vacuum 974, which may be any suitable source, for example, the suction source may include a pump, a venturi, or may be a syringe with a spring-loaded plunger as described elsewhere herein. The suction source can be within the hand-held portion as described elsewhere herein or remote from the hand-held portion. The actuator 942 controls the magnitude of suction in any suitable manner and as described elsewhere herein. The valve 968 is movable to a partially open position between the closed position and the fully open position and may be positioned at any position therebetween. The partially open position can have a cross-sectional flow area that is 5-15% of a cross-sectional flow area of the fully open position. As used herein, the percentage open is generally proportional to the longitudinal position of the valve 968 relative to the aperture 970. The partially open position may also be an open position that is less than 15% of the cross-sectional flow area of the fully open position.

The support sled 946 is slideably mounted to the base 947 to displace laterally when the foot pedal 944 is displaced. The support sled 946 also carries the motor 956. The vacuum source 974 is independently mounted to the base 947 so that the wire 972 may move independent of the lumen (not shown) coupled to the connector. A control system 991 is coupled to the motor 956 and vacuum source 974 to control each of these components as described herein.

The actuator 942 is operably coupled to the valve 968 and the suction source 974 and may be operated in any conventional manner. For example, the valve 968 may move between a first position and a second position that exposes more of the aperture 970 to increase and decrease the suction pressure periodically.

In accordance with another aspect, the actuator 942 may also control the valve 968 and suction source 974 as now described. When the actuator 942 is initially displaced from the position of FIG. 23A, the actuator 942 moves the valve 968 to the partially open position during a first phase of displacement of the actuator 942 from the off position. During the first phase, the vacuum source 974 increases the vacuum/suction pressure as the actuator 942 displacement increases. The valve 968 may stay in the partially open position until the vacuum pressure reaches at least 75% of a target maximum pressure that may be 570 mmHg (with a target pressure of 760 mmHg). The first phase may also continue until the target pressure is reached. Stated another way, the actuator 942 controls the valve 968 to being no more than half open until the target pressure is reached during the first phase of displacement of the actuator 942. The target pressure may also simply be reached by increasing the suction pressure without modulating the pressure until full suction pressure is reached without regard to the actual pressure as long as the result is reaching the target pressure in the manner described herein.

Once the target pressure has been reached, further displacement of the actuator 942 (e.g. foot pedal 944) defines a second phase of displacement in that the suction pressure is increased and decreased at a rate of at least 1 Hz (or 1-10 Hz). During the second phase, the valve 968 moves between a first position and a second position with the second position providing a larger cross-sectional flow area along the flow path than the first position. The first position may be the partially open position or may be the closed position and, similarly, the second position may be the fully open position or any other intermediate position so long as it provides a larger flow area than the first position. When the valve 968 is open in the first position, the cross-sectional flow area in the first position may be at least 5%, or 5-15%, of the cross sectional flow area related to the fully open position of the valve 968. The first and second phases may provide an improvement over some systems and methods that immediately modulate/cycle the suction pressure. The first phase may help in establishing the desired suction pressure that is then transitioned to the cyclic/periodic or modulated second phase.

The actuator 942 may also have a third phase of displacement following the second phase (or directly after the first phase). During the third phase, the actuator 942 also moves the valve 968 between a first position and a second position with the second position of the valve 968 providing a larger cross-sectional flow area along the flow path than the first position. The third phase of operation moves the valve between a first position and a second position with the second position having a larger cross sectional flow area than the first position, As the actuator 942 displacement is increased, the duty cycle increases so that the valve 968 increases time nearer to the second position relative to the first position. The valve 968 is preferably moved at a rate of at least 1 Hz during this phase of operation.

Alternatively, the actuator 942 is operably coupled to the valve 968 so that an increase in displacement of the actuator 942 during the third phase causes the second position of the valve 968 to define an increasing cross-sectional flow area for the suction path (such as an increasing amount of the aperture being exposed, for example). The first position may stay the same during the third phase and may be the partially open position. Stated another way, during the third phase, the actuator 942 is operably coupled to the valve 968 so that the increase in displacement of the actuator 942 (foot pedal 944) increases a distance between the first position and the second position so that more of the aperture is exposed during each cycle. During the second and third phases the vacuum source may be maintained at full suction pressure. As used herein, the terms "first", "second" and "third" may be interchanged and, in particular, in the claims. For example, the claims may be formed to recite the just described first and third phases as the first and second when the just described second phase is omitted. Furthermore, the second phase may form part of the third phase in that the second phase is established when the third phase is initiated.

The valve 968 may also be movable along the suction path to purge the suction path by moving material through the suction path in an opposite direction to suction of material. To this end, the valve 968 is movable distally beyond the closed position so that the valve 968 pushes material in the direction opposite to suction, that is, distally through the suction path toward the opening 964. The valve 968 may displace material in the opposite direction to suction during each cycle of movement (from the first position to the second position and back to the first position). The material in the suction path is purged in this manner that may help dislodge material caught in the suction path or stuck to the tip. The valve 968 displacement is limited by a stop 975 that defines the volume displaced by the valve 968.

Figure 24A:
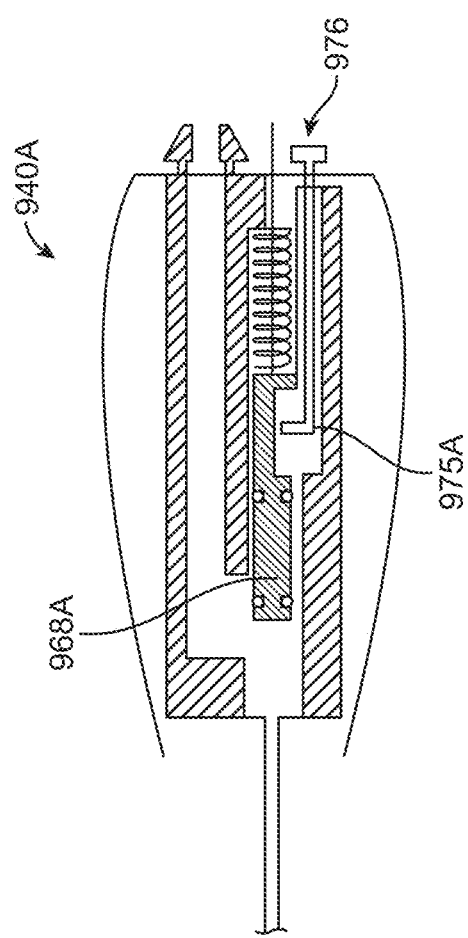
FIGS. 24A-24B shows two views of an alternative embodiment with an adjustable stop for defining a maximum distal displacement of the valve.
Figure 24B:
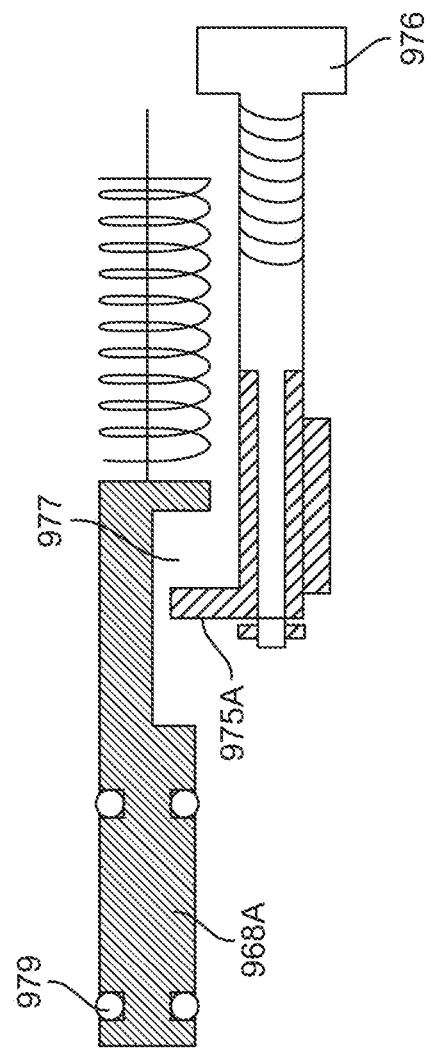
Figure 25A:
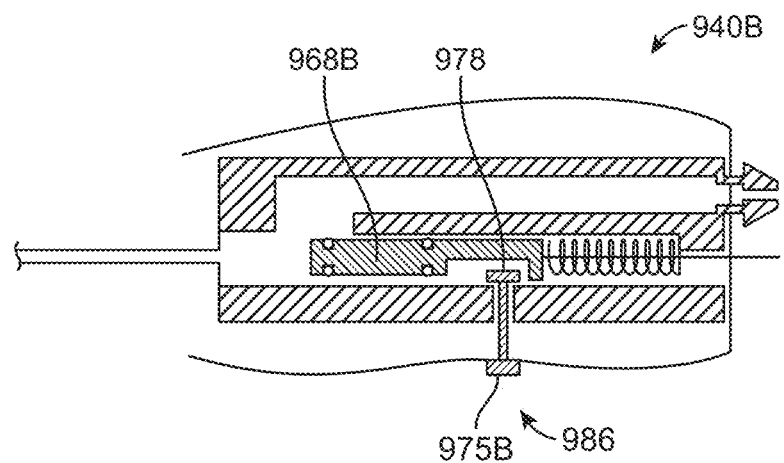
FIGS. 25A-25B shows two views of another alternative embodiment with an adjustable stop in the form of a cam.
Figure 25B:
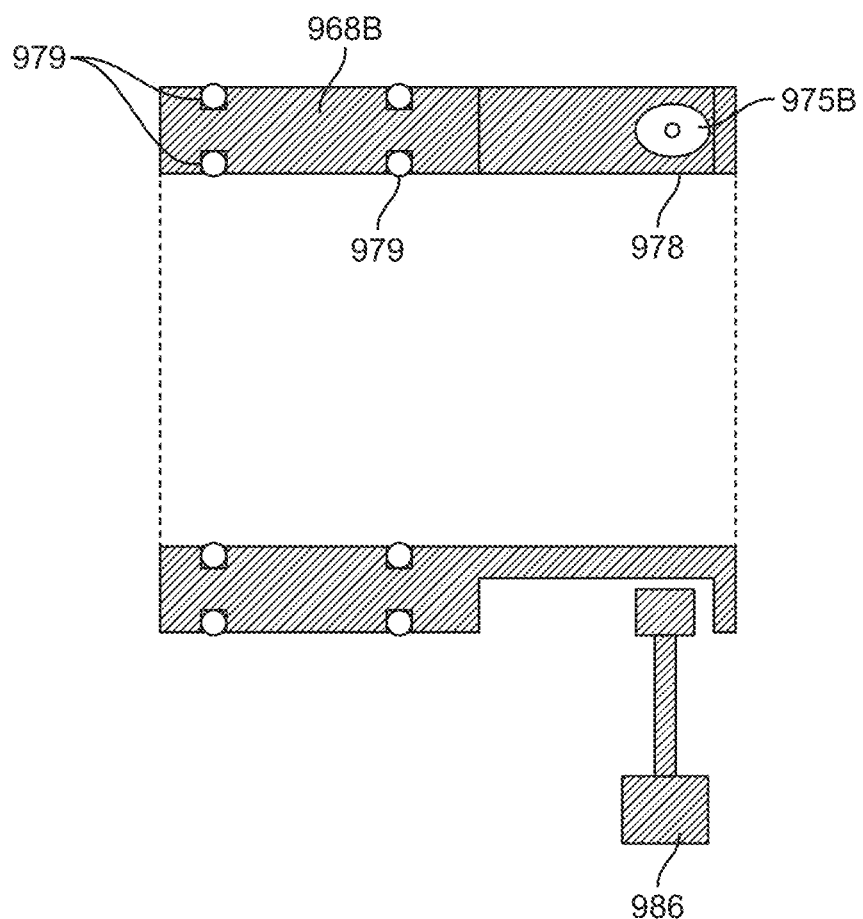

Referring to FIGS. 24A-24B, another device 940A is shown that has an adjustable stop 975A that adjusts the maximum displacement of the valve 968A and, thus, adjusts the volume that is displaced by the valve 968A. The adjustable stop 975A is coupled to a thumb screw 976 that is manually operable by the user to adjust the position of the adjustable stop 975A. The stop 975A is positioned in a cavity 977 in the valve 968A and limits the motion of the valve 968A when the valve 968A contacts the stop 975A. Referring to FIGS. 25A-25B, another device 940B is shown having an adjustable stop 975B coupled to a cam 978 that engages the valve 968B. The cam 978 is rotated by the user with a dial 986 to adjust the maximum displacement of the valve 968B and volume of the displaced material.

The adjustable stops 975A, 975B also provide on-demand purge capability. For example, the stops 975A, 975B may be initially positioned so that the maximum distal displacement corresponds to the closed valve position. When retrograde purging is desired, for example, to dislodge material in the lumen or stuck to the distal end, the stops 975A, 975B can be moved to a position that permits distal travel beyond the closed position. When the valve 968 travels distally beyond the closed position, the valve 968 seals with the suction path along 0-rings 979 so that the valve 968 acts like a positive displacement pump when moving material in the opposite direction to suction (i.e. towards the distal opening). The valve 968 also draws material in the direction of suction (after moving material in the opposite direction) so that the valve 968 acts like a positive displacement pump in the direction of suction, which may aid in reestablishing suction flow during the flow reversal as the aperture 970 is opened.

Figure 26:
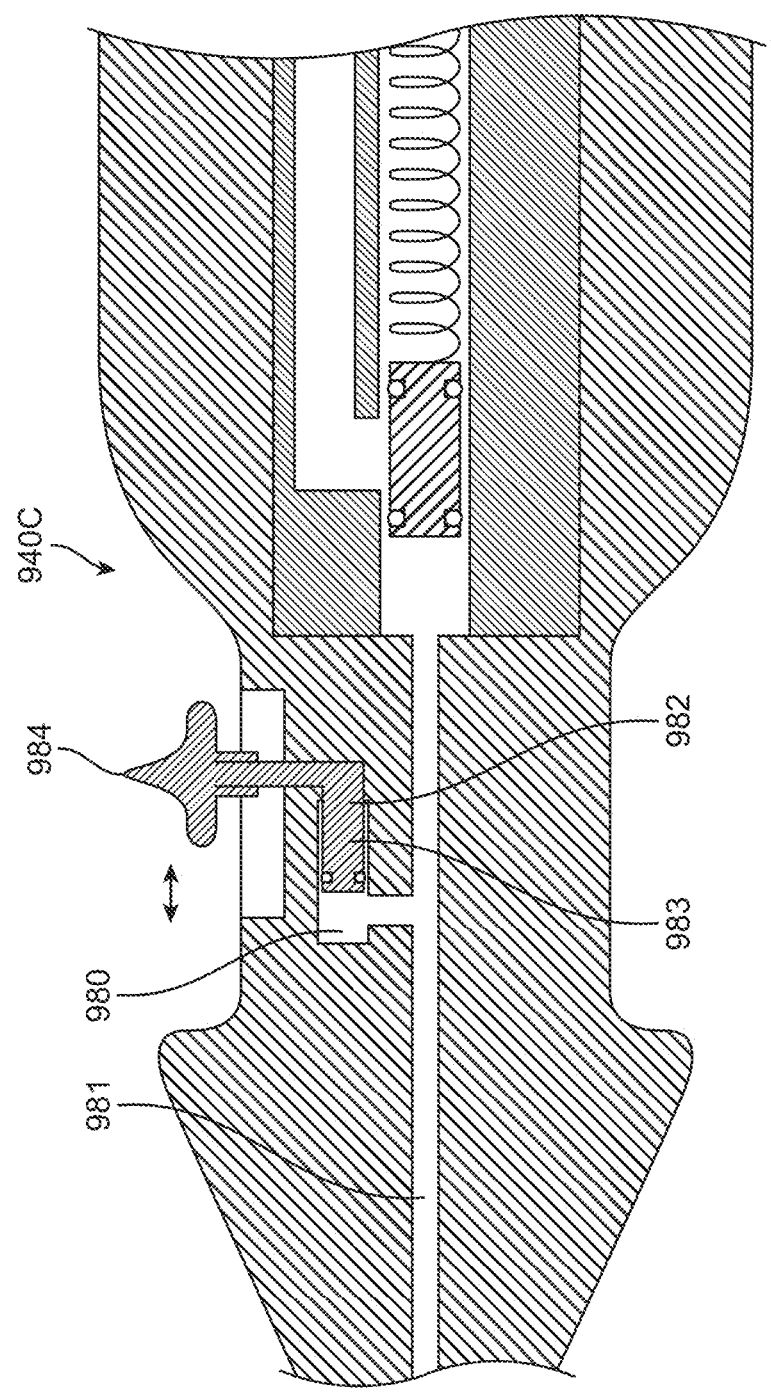
FIG. 26 shows a retrograde flow element positioned in a retrograde channel that is coupled to the main lumen.

Still another device 940C for aspirating material in the eye is shown in FIG. 26. The device 940C includes a retrograde flow channel 980 fluidly coupled to a lumen 981 and a retrograde flow element 982 is configured to move the fluid through the retrograde flow channel 980 into the lumen 981 in the opposite direction to clear the lumen 981 and material stuck to a distal end. The retrograde element 982 may be a plunger/piston 983, bladder or any other suitable mechanism for moving fluid. The piston 983 is coupled to a thumb actuator 984 although any other suitable actuator may be used. The adjustable stops 975A, 975B of the devices of FIGS. 24A-24B and 25A-25B and the retrograde flow channel 980 and retrograde flow element 982 of FIG. 26 may be incorporated into the device 940 of FIGS. 22 and 23

(or any other suitable devices described herein) and such combinations shall include all uses, methods and characteristics of the other devices are applicable to the combination and expressly incorporated herein.

Described herein are various devices configured to perform one or more functions useful in ophthalmic procedures including, but not limited to, cutting, fragmentation, emulsification, aspiration, and/or inspiration of material present at a target location during a procedure in the eye. "Material" as used herein can include fluids (from the eye or provided to the eye), tissues, or fragments of tissues such as lenticular tissue, vitreous tissue, cells, and any other fluid or tissue or other material that may be present during a procedure in the eye (e.g. cataract procedure, vitrectomy procedures, and the like). The devices described herein configured to apply vacuum may also be configured to deliver fluids. The devices described herein that apply vacuum and/or deliver fluids may also be configured to cut, fragment, emulsify, or otherwise make smaller material in and near the surgical site. Devices described herein that allow for vacuum to be applied can provide that vacuum using pulsed vacuum with or without interspersed pulsed positive pressure.

The various features and functions of the devices described herein may be applied to one or more devices described herein even though they may not be expressly described in combination. It should also be appreciated that various features and functions of the devices described herein can be applied to conventional devices and systems known in the art also useful for cutting, fragmenting, emulsifying, or otherwise impacting tissues at or near a surgical site, including, but not limited to phacoemulsification systems, vitrectomy systems, and other tools useful in performing cataract surgeries or vitrectomy surgery, and the like.

FIGS. 27A-27H and FIGS. 28A-28N illustrate interrelated implementations of devices configured to cut and aspirate material during procedures in the eye. The devices allow for performing cataract surgeries in a minimally-invasive, ab interno approach through clear corneal incisions. The devices described herein rely on fewer manipulations and less energy to remove the lens from the eye. The devices are configured to create smaller lens fragments with a single cut that are easier to remove through the small incisions with little to no phacoemulsification. The devices described herein can be all-in-one devices configured to cut a lens in situ into small lens fragments that can be removed by the same device with aspiration and little to no phacoemulsification.

FIGS. 27A-27H illustrate a device 2700 that includes a hand-held unit 2760 having a distal, elongate member or shaft 2761 coupled to and extending longitudinally from a housing 2762 of the hand-held unit 2760. At least a distal end region of the shaft 2761 is configured to be inserted into the eye in a minimally-invasive manner to cut, aspirate, and/or inject material in the eye, such as during a cataract procedure. The shaft 2761 can be an elongate member configured to oscillate.

As used herein, "oscillate" or "oscillating movements" can include any periodic, repetitive movement that occurs according to a pattern and need not be sinusoidal. The oscillating movement can include reciprocating sliding movements that occur in a back and forth manner relative to the hand-held unit. The oscillating movement can include repeatedly advancing and retracting the elongate member along its longitudinal axis. The repeated advancing and retracting may occur along the longitudinal axis, but the path the oscillating movements take need not be linear. The path of movement can occur non-linearly (i.e. away from the longitudinal axis during at least a portion of the movement) along an elliptical pathway or a curvilinear pathway. The path of movement can be rotationally, orbitally, torsionally around the longitudinal axis of the device or other type of movement relative to the longitudinal axis of the device including three-dimensional movements in which the elongate member moves back and forth as well as from side-to-side. The oscillating movements include profiles of repetitive movement patterns that may change depending on where in the cycle of oscillation the movement occurs. The oscillating movements can be asymmetric in profile, as will be described in more detail below.

Any of a variety of configurations of the elongate member are considered herein. In some implementations, the elongate member can include a tubular oscillating elongate member having an internal lumen extending through it such that fluids can be delivered and/or aspirated through the oscillating elongate member. In other implementations, the oscillating elongate member is not tubular, but instead formed as a solid element. In this implementation, the oscillating elongate member can reciprocate within an outer tubular member and a gap between the shafts sized to receive and/or deliver fluids to the treatment site. Where the elongate member is described as having inner and outer members the elongate member can also be formed of a single tubular element configured to oscillate relative to the hand-held unit to cut and aspirate material. Where the elongate member is described as having an inner elongate member coaxially arranged within an outer tubular member the inner elongate member can be a solid rod and need not include an inner lumen. In some implementations, the elongate member has a sharpened cutting tip or bevel, which can include a needle tip.

Use of the term "needle" or "needle tip" need not imply the elongate member has a lumen extending through it as a syringe needle would. For example, an elongate member having a sharpened needle tip can be a solid element extending through an outer tubular member and aspiration forces applied through the lumen of the outer tubular member such that fluids and tissues are drawn into an annular gap extending between the inner and outer members. In other implementations, the elongate member is a cutting tube having an inner lumen and distal edge configured to cut tissue. The distal edge can be sharpened while the opening into the tube can be cut at an angle to the elongate axis of the elongate member or perpendicular to the elongate axis of the elongate member. The cutting tube can have an inner lumen configured to aspirate material therethrough, such as ocular lens material, lens fragments, and/or fluids from the eye. Thus, aspiration forces can be applied through the inner lumen of the inner elongate member. However, aspiration forces can also be applied through a lumen of a tubular outer member. The gap between the tubular outer member and the inner member can vary, for example, between about 0.001" to about 0.100". In some implementations, the aspiration forces can be applied through both the inner elongate member having a lumen and the lumen through the outer tubular member.

Again with respect to FIGS. 27A-27H, the shaft 2761 can be a vitrectomy-style cutting element in that it can have an elongate member 2755 extending through and coaxially arranged within an outer tube 2759 such that the elongate member 2755 slides reciprocally within the outer tube 2759. This style cutting element can be particularly useful for chopping and removing harder lens material compared to tips such as those shown in FIGS. 6A-6C described above. The outer tube 2759 can be a stationary tubular element coupled to a distal end region of the housing 2762. The outer tube 2759 can be fixedly coupled within an interior of the distal end region of the housing 2762 by a retainer 2743. The retainer 2743 can be a donut-shaped element configured to receive the outer tube 2759 therethrough such that the retainer is positioned about a proximal end region of the outer tube 2759. The elongate member 2755 can also be a tubular element, but unlike the outer tube 2759, is movable such that it can be oscillated within the lumen of the outer tube 2759. A distal tip of the elongate member 2755 can be formed into a cutting edge 2754. In some implementations, the cutting edge 2754 is a short, sharpened bevel (see FIG. 27C-27D). Each of the outer tube 2759 and the elongate member 2755 can have an opening 2753, 2758 near their respective distal end regions. In some implementations, the openings 2753, 2758 are formed through respective side walls (see FIGS. 27C-27D). Together, the cutting edge 2754 of the elongate member 2755 and the opening 2753 of the outer tube 2759 form a port 2764. The port 2764 can vary in size depending on the position of the elongate member 2755 relative to the outer tube 2759. In operation, tissue may enter into the shaft 2761 through the port 2764 and be dissected by the cutting edge 2754 as the elongate member 2755 is reciprocated within the outer tube 2759.

The device 2700 can include a removable or retractable, outer sheath for sliding over the openings 2753, 2758, for example, during insertion of the shaft into the anterior chamber. During insertion, the cutting area of the shaft can remain covered with the sheath to prevent snagging on the incision or other eye tissues prior to cutting. After insertion, the sheath can be retracted or otherwise removed when the operator is ready to start cutting and/or aspirating. The retraction can be manually activated by a user or can be automatically retracted by the device upon actuation of cutting and/or aspiration. After cutting/aspiration is complete and the instrument is ready to be removed from the eye, the sheath can be advanced distally to once again cover the openings 2753, 2758.

The shaft 2761 is described above as including an oscillating elongate member 2755 extending through an outer tube 2759. The outer tube 2759 can be stationary and thereby protect the corneal incision or other tissues through which the shaft 2761 extends from being impacted by oscillating movements of the elongate member 2755. The shaft 2761 can include a single tubular elongate member 2755 that oscillates without any outer tube 2759. However, it is preferable the shaft 2761 include a protective sheath surrounding at least a portion of the oscillating elongate member 2755, for example, to protect the cornea from tissue damage due to being exposed to the oscillating movements of the elongate member 2755. The protective sheath can be formed of an elastic material such as silicone or a more rigid metal hypotube. The protective sheath can be exchangeable and/or retractable. The length of the protective sheath can vary. The protective sheath can have a minimum length configured to cover the region where the shaft 2761 extends through the corneal incision. The color of the sheath can provide information regarding the length of the sheath and for what purpose it is useful. A user can cover the oscillating elongate member 2755 and use a different sort of tip during a procedure, for example for polishing or cleaning up after cutting. Longer length of the protective sheath can cover half the stroke of the oscillation to be softer on the eye. The protective sheath can also be useful to prevent clogging of the lumen of the shaft, for example, by preventing tissues from 'lollipopping' the end of the shaft 2761.

As will be described elsewhere herein, the shaft 2761 can also include an irrigation sleeve configured to deliver irrigation to the work site. The irrigation sleeve can extend over at least a portion of the protective sheath. The irrigation sleeve and protective sheath can be removable such that they detach from the hand-held unit 2760. In some implementations, the irrigation sleeve and protective sheath are removed together as a single unit (e.g. as part of a removable cap) from the housing or removed individually. Generally, the shaft 2761 (including the protective sheath and irrigation sleeve, if present) has a maximum cross-sectional diameter that is suitable for minimally-invasive procedures in the eye to minimize the corneal incision size. In some implementations, the maximum cross-sectional diameter of the distal shaft 2761 is about 1.25 mm. The maximum cross-sectional diameter can be smaller than this or can be larger than this diameter, for example, no more than about 2 mm in diameter, no more than about 3 mm in diameter, up to about 4 mm in diameter, or up to about 5 mm in diameter. As described elsewhere herein, a distal opening from the shaft 2761 can have a smaller inner diameter in relation to the inner diameter of the lumen extending through the shaft 2761 to mitigate problems with clogging. In some implementations, the difference between the nominal inner diameter of the shaft 2761 and the inner diameter of the distal opening can be between about 0.003" to about 0.006". In some implementations, the shaft 2761 can have a nominal inner diameter of about 0.0375" that narrows at the distal opening to about 0.033". Thus, eye tissue pieces that are less than the tip diameter can get aspirated into the lumen of the shaft 2761 and once inside the lumen are less likely to get stuck or cause a clog because the inner diameter of the remainder of the lumen is larger than the inner diameter of the distal opening.

The elongate member 2755 can be oscillated relative to the hand-held portion by a drive mechanism operatively coupled to the elongate member 2755. The drive mechanism can vary including electric, piezoelectric, electromagnetic, hydraulic, pneumatic, mechanic, or other type of drive mechanism known in the art. In some implementations, the elongate member 2755 is reciprocated by a drive mechanism including a motor 2756 contained within an interior of the housing 2762. The configuration of the motor 2756 can vary including, any of a variety of rotation motors, stepper motor, AC motor, DC motor, a piezoelectric motor, a voice coil motor, or other motor.

In some implementations, the drive mechanism includes a motor 2756 such as a gear motor having a gear head 2752 coupled (directly or via a motor coupler 2789) to a proximal end of a rotating cam 2769. The rotating cam 2769 can be coupled at an opposite end to a cam follower 2787, which is fixedly coupled to a proximal end of the elongate member 2755. The gear head 2752 can be driven to rotate the rotating cam 2769, which converts the rotary motion of the motor 2756 into linear motion of the cam follower 2787 and thus, linear motion of the elongate member 2755.

In some implementations, as shown in FIGS. 27E-27H, the rotating cam 2769 can be a generally cylindrical element having a bore 2789 in a proximal end configured to receive the gear head 2752. The cam follower 2787 can have a bore 2790 in a proximal end configured to receive the distal end of the rotating cam 2769. The rotating cam 2769 can be a barrel cam. The outer surface of the distal end of the cam 2769 has a channel 2792 configured to receive a corresponding pin element 2793 of the cam follower 2787. As the gear head 2752 turns the cam 2769 around the longitudinal axis of the device, the pin element 2793 moves through the channel 2792 around the outside surface of the cam 2769. The channel 2792 in the outer surface of the cam 2769 follows an elliptical path from a first proximal end region towards a distal end region of the cam 2769 and then from the distal end region back towards the first proximal end region. As the pin element 2793 moves through the channel 2792 during rotation the cam follower 2787 is urged to move axially along a longitudinal axis of the device. The cam follower 2787 moves in a distal direction for at least a fraction of the rotation. The cam follower 2787 then moves in a proximal direction for at least another fraction of the rotation. As such, a complete revolution of the cam 2769 provides reciprocating axial movement of the cam follower 2787 and the elongate member 2755. It should be appreciated that other drive mechanisms to create oscillating movements of the elongate member are considered herein.

Figure 27A:
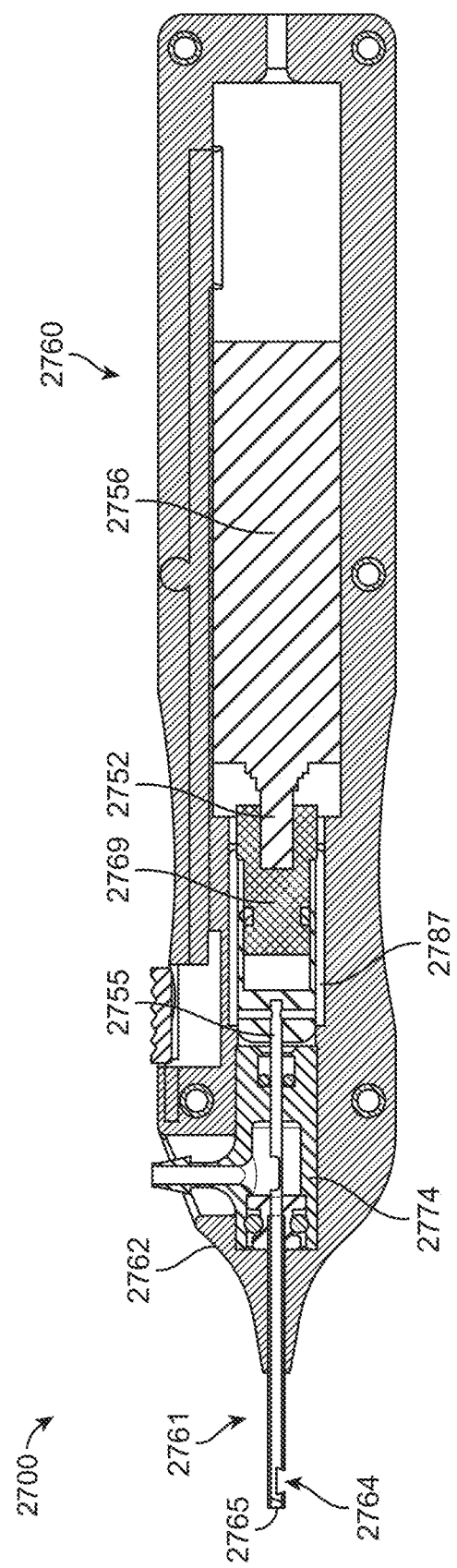
FIGS. 27A-27B show cross-sectional views of an implementation of a device for cutting and aspirating material from an eye.
Figure 27B:
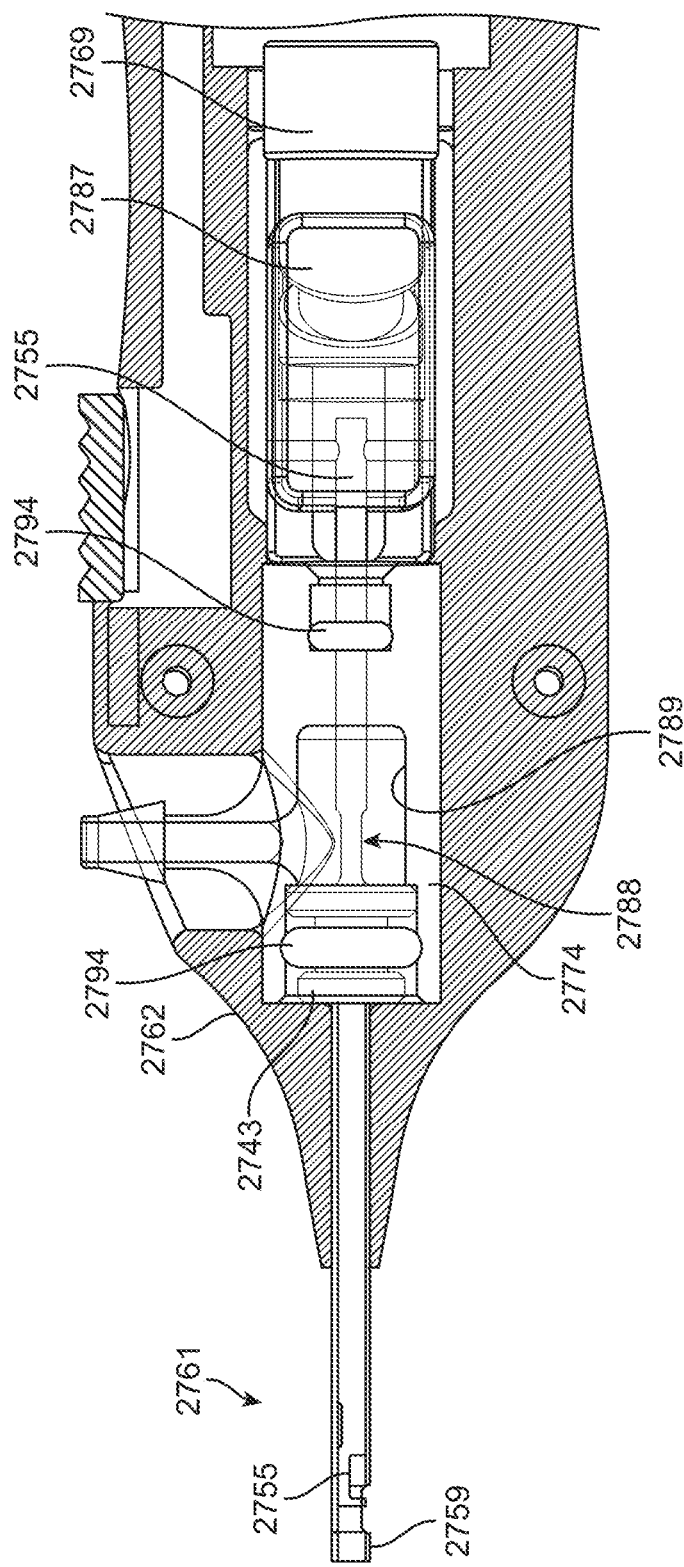
Figure 27C:
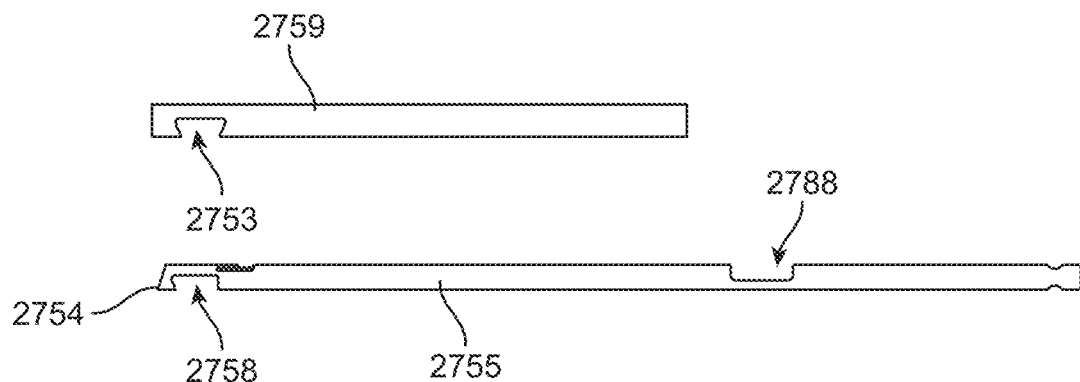
FIGS. 27C-27D show view of the cutting tool of the device of FIGS. 27A-27B.
Figure 27D:
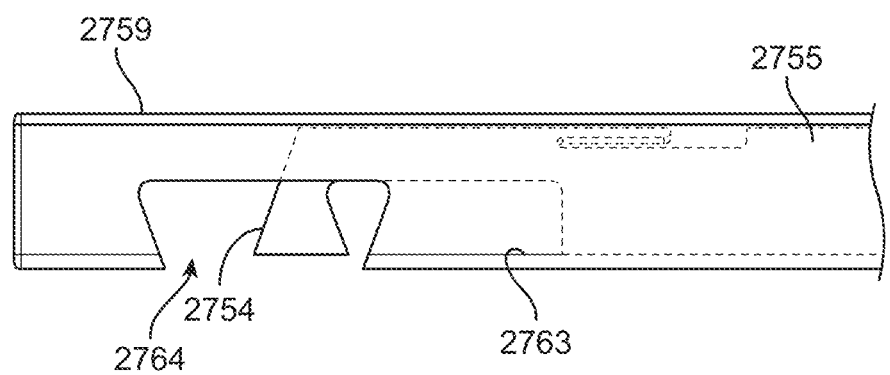
Figure 27E:
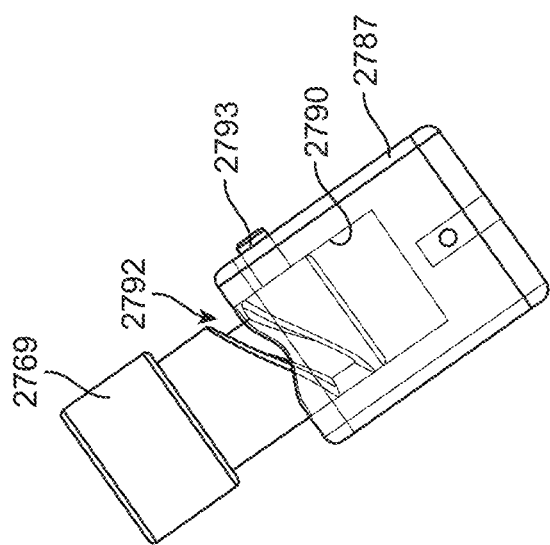
FIGS. 27E-27H show various perspective views of a barrel cam of the device of FIGS. 27A-27B.
Figure 27F:
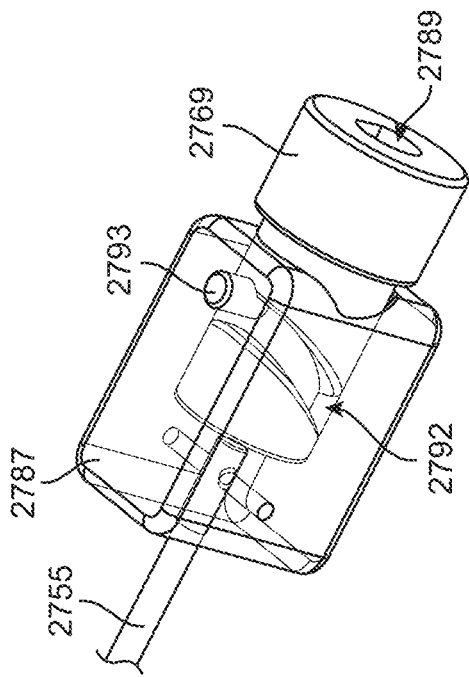
Figure 27G:
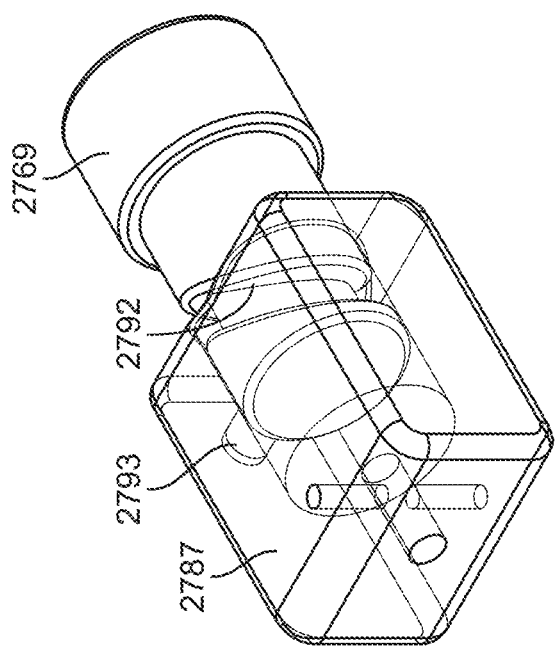
Figure 27H:
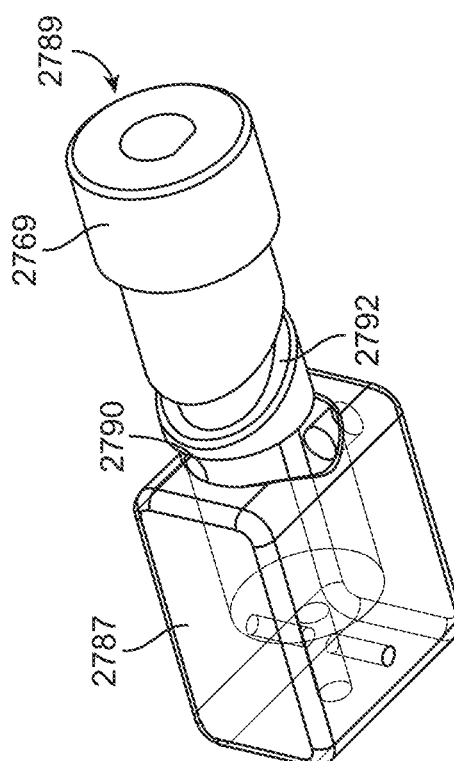

Again with respect to FIGS. 27A-27D, the elongate member 2755 can be covered at least in part by the outer tube 2759. The outer tube 2759 may be fixedly coupled to the housing 2762, for example, by the retainer 2743. The oscillating elongate member 2755 can trap lens material between cutting edge 2754 and the opening 2756 to cut small pieces of the lens material drawn into the port 2764. The port 2764 near a distal end 2765 of the shaft 2761 communicates with a lumen 2763 forming a suction path leading from the port 2764. The lumen 2763 forming the suction path can extend through the elongate member 2755 and/or between the elongate member 2755 and the outer tube 2759. In some implementations, the lumen 2763 extends through the elongate member 2755 to a proximal opening 2788. As best shown in FIG. 27B, the elongate member 2755 can be coupled at a proximal end region to the cam follower 2787. The elongate member 2755 extends through a vacuum manifold 2774 located within the interior of the hand-held unit 2760 such that the proximal opening 2788 communicates with a chamber 2789 of the vacuum manifold 2774. The proximal opening 2788 is maintained within this chamber 2789 during oscillating movements of the elongate member 2755. A vacuum is applied within the vacuum manifold 2774 to aspirate the dissected tissue from the eye through the lumen 2763. The dissected tissue enters the lumen 2763 at port 2764 and exits the lumen 2763 through the proximal opening 2788. A plurality of seals 2794, such as sliding O-rings that provide low resistance to movement, can prevent and/or substantially reduce the passage of fluid around the shaft 2761. The device 2700 can be coupled to a suction source that is either remote from the hand-held unit 2760 or within an interior of the hand-held unit 2760 such that the device 2700 is a fully hand-held device as described elsewhere herein. Also, as described elsewhere herein, the elongate member 2755 need not include an outer tube 2759 and can perform fragmentation of tissues on its own. In some implementations, the elongate member 2755 can include a wall having a port 2764 through the wall where the port has a cutting surface. In other implementations, the elongate member 2755 can include a cutting tip such as a beveled cutting tip. The cutting tip can include a distal opening from the lumen extending through the elongate member 2755. Ocular material can be aspirated through the lumen of the elongate member 2755, a lumen of the outer tube 2759, or both lumens.

The port 2764 can have a width that is optimized for fully chopping and aspirating the eye tissue. In some implementations, the port 2764 can have an axial length that is greater than 0.05" up to about 0.175". The port 2764 can have a width that can be between 0.015" and 0.06". The wider port 2764 under full vacuum conditions (e.g. about 15 inHg up to about inHg) can increase the risk of anterior chamber collapse. Thus, as described elsewhere herein, the vacuum can be applied in pulses of negative pressure, for example, by actuation of one or more valves. Additionally, the cycles of negative pressure can be interspersed with short regurgitation via application of positive pressure between pulses of negative pressure. As described elsewhere herein, the cycling of the negative pressure pulses and positive pressure pulses can be very fast (e.g. 1 Hz) and very small volumes (e.g. 5 cc).

As mentioned, the devices described herein can include one or more user inputs or actuators such as a button, slider, switch, or other input. The one or more user inputs can be on the device itself, remote from the device, or both. The device can include separate inputs to activate each function of the device (i.e. aspiration, including pulsed vacuum with regurgitation between pulses, cutting, infusion, etc.). Alternatively, the input can be a multi-way button to activate more than a single function of the device. For example, the device can be configured for vacuum and cutting. The one or more inputs can activate vacuum-only function and vacuum-plus-cutting function. Generally, cutting without vacuum is not desired, however, a cutting-only function is considered herein as well. As an example and not to be limiting, a user can activate a first button or place the button in a first position to turn on the vacuum-only function. After the first button is activated, the user can then activate a second button or place the button in a second position to turn on the vacuum-plus-cutting function. The user can then commence cutting while vacuum continues. In some implementations, the second button activation is only possible after the first button activation occurs. In another implementation described in more detail below, the input can be a multi-way actuator that has a first position configured to turn on both vacuum and oscillate the elongate member (i.e. vacuum-plus-cutting function) and a second position configured to pause oscillation of the elongate member while the vacuum through the elongate member continues.

Figure 28C:
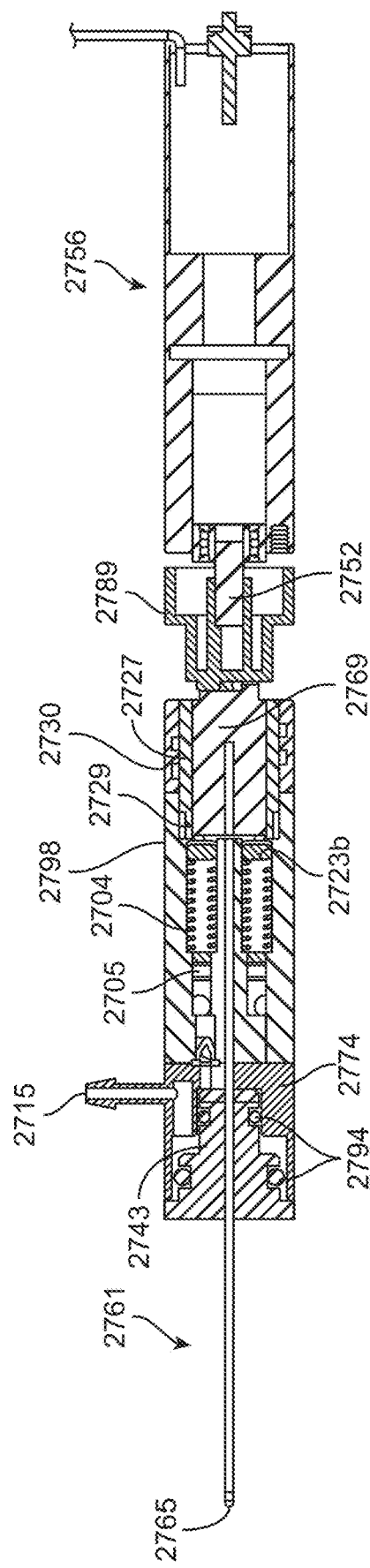
FIGS. 28C-28D show cross-sectional view of the device of FIGS. 28A-28B taken along line C-C and D-D, respectively.
Figure 28D:
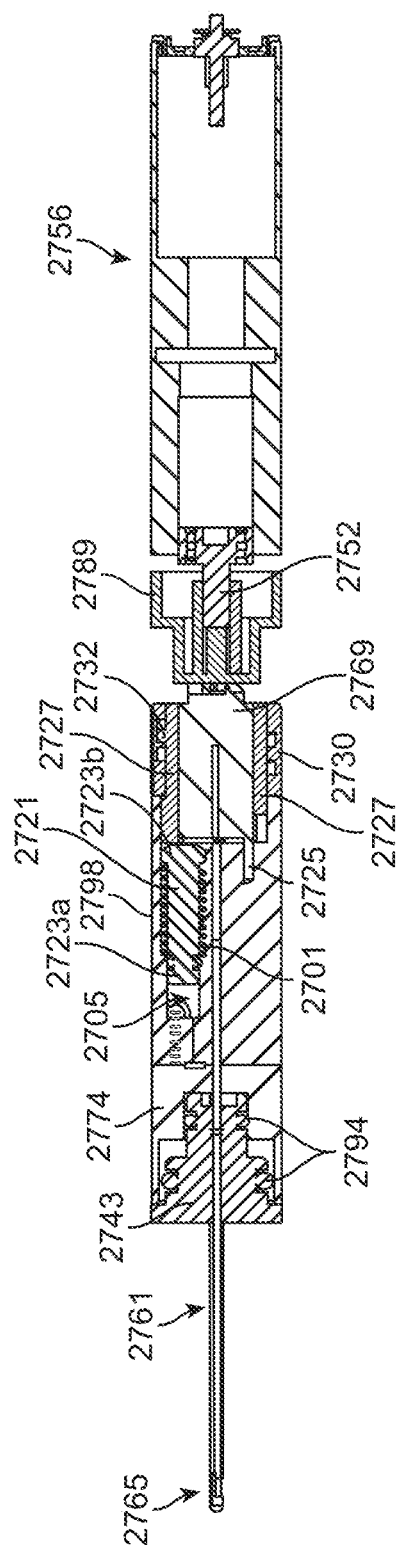
Figure 28E:
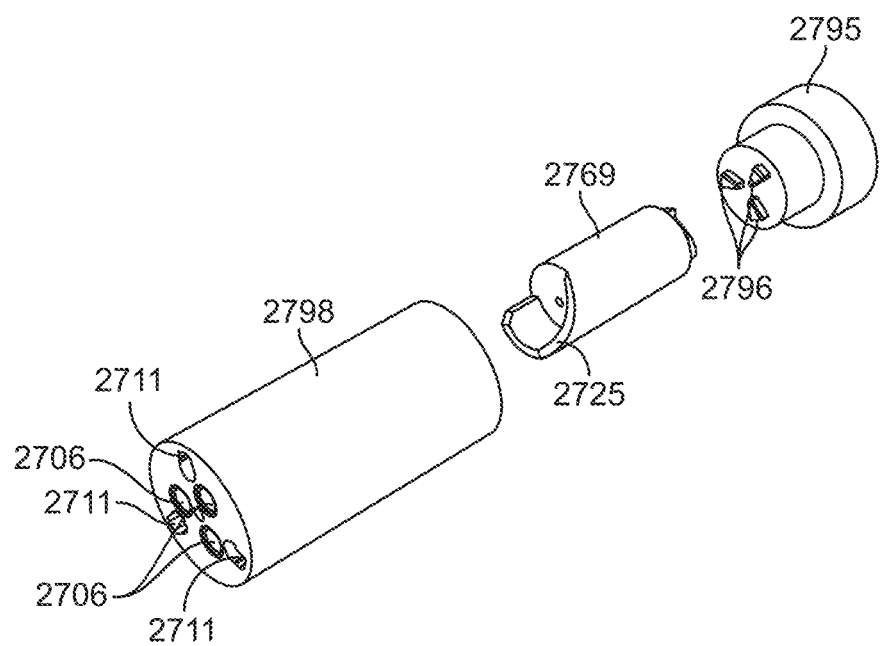
FIGS. 28E-28G show various view of a rotating cam of the device of FIGS. 28A-28B.
Figure 28F:
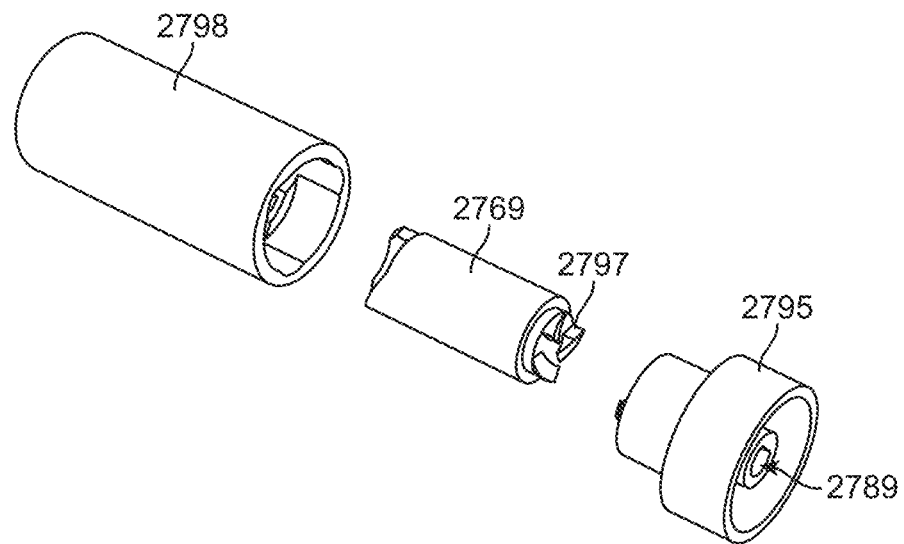
Figure 28G:
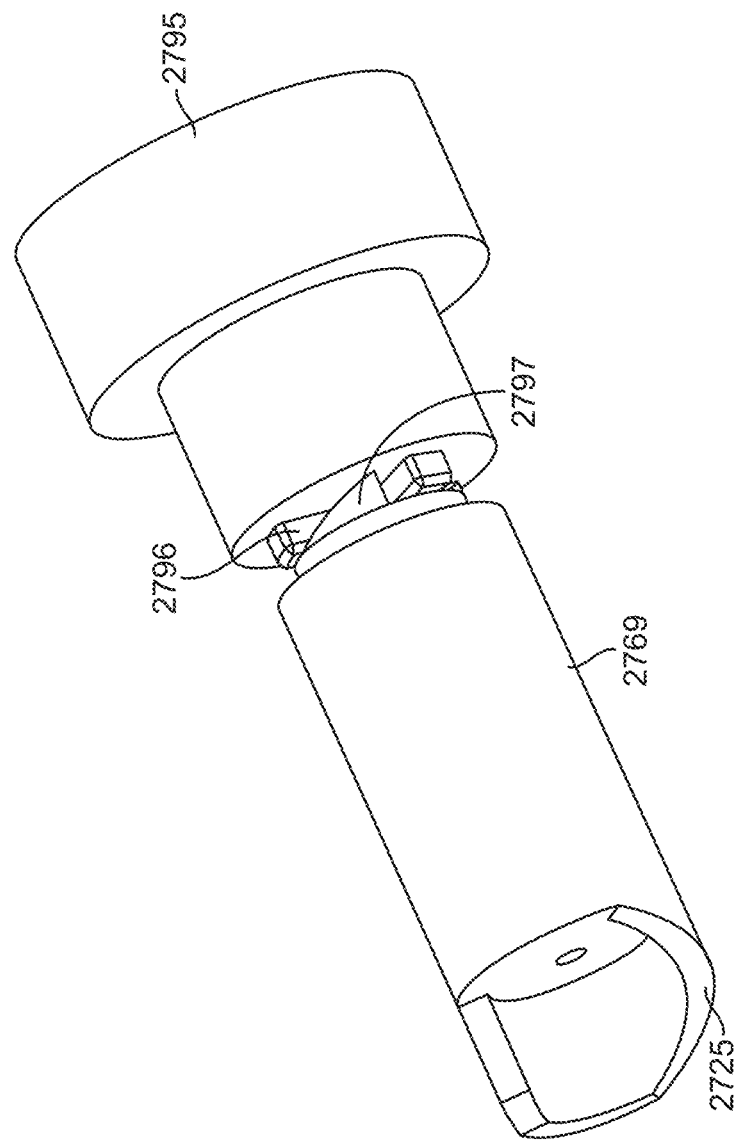
Figure 28H:
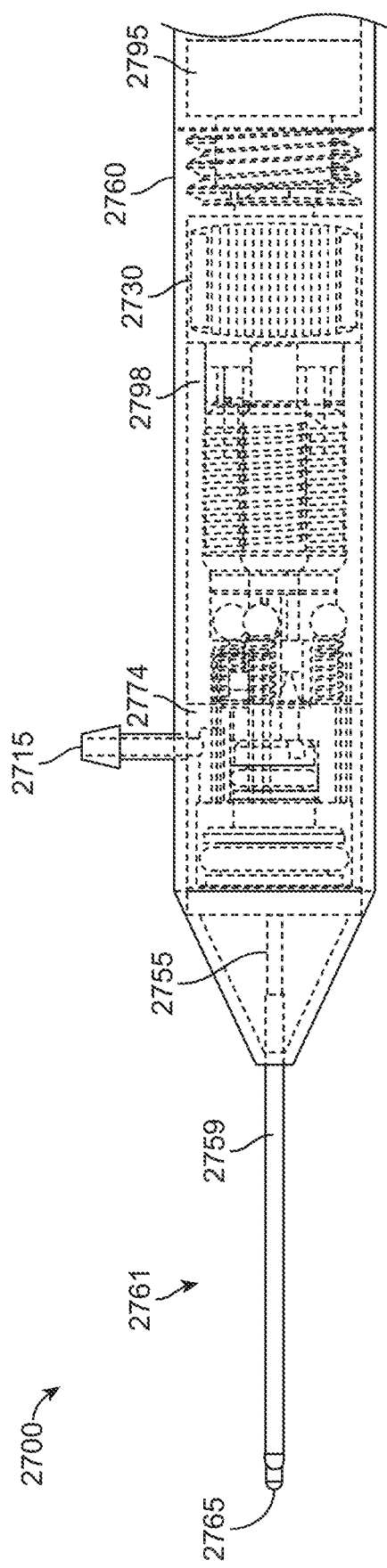
FIGS. 28H-28N are additional views of various components of the device of FIGS. 28A-28B.
Figure 28I:
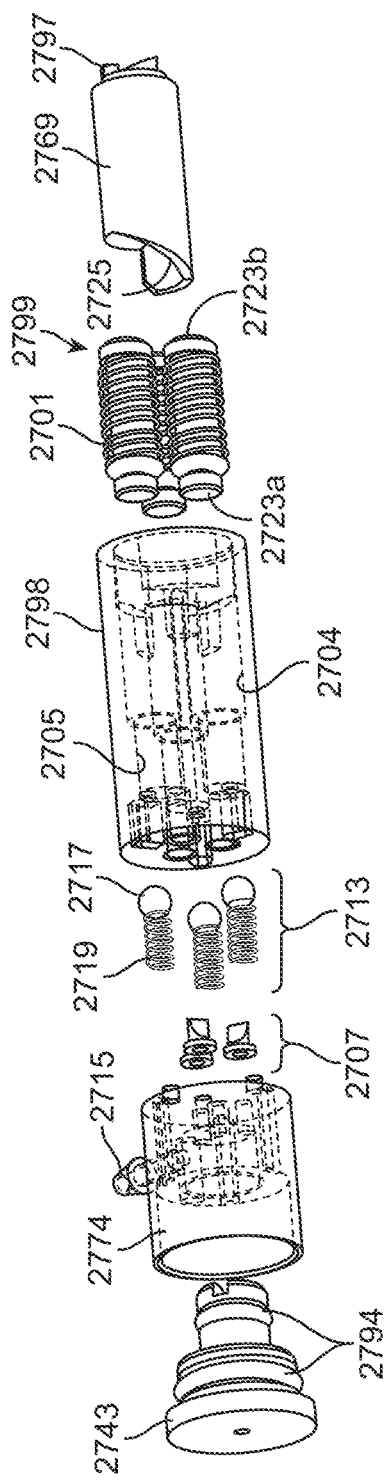
Figure 28J:
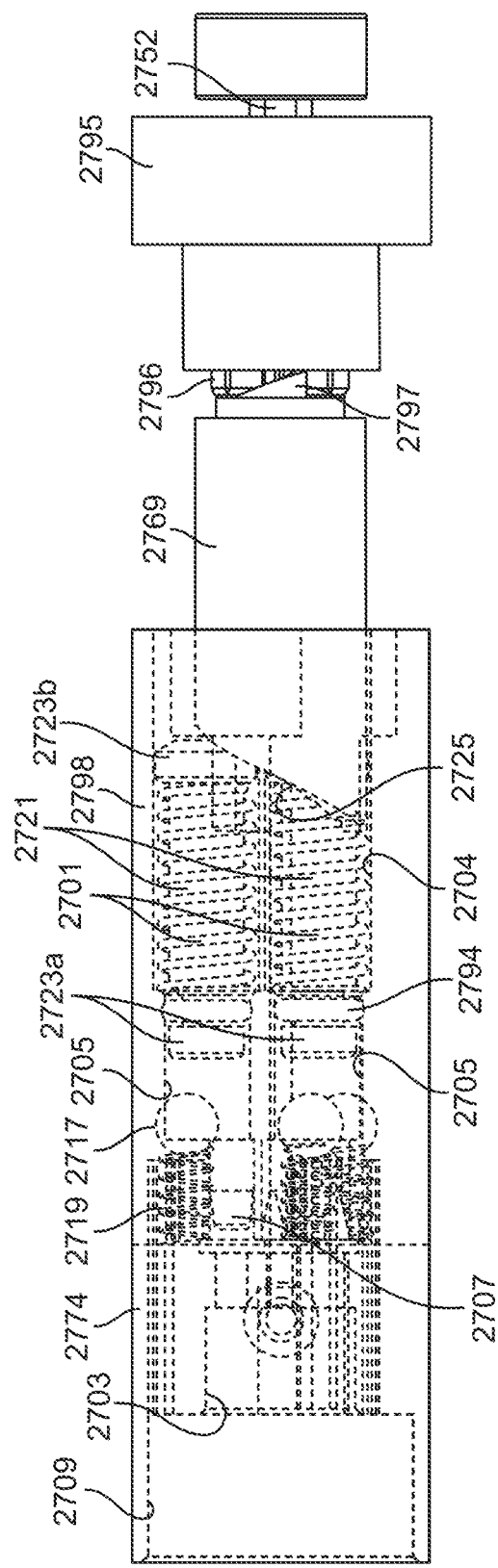
Figure 28K:
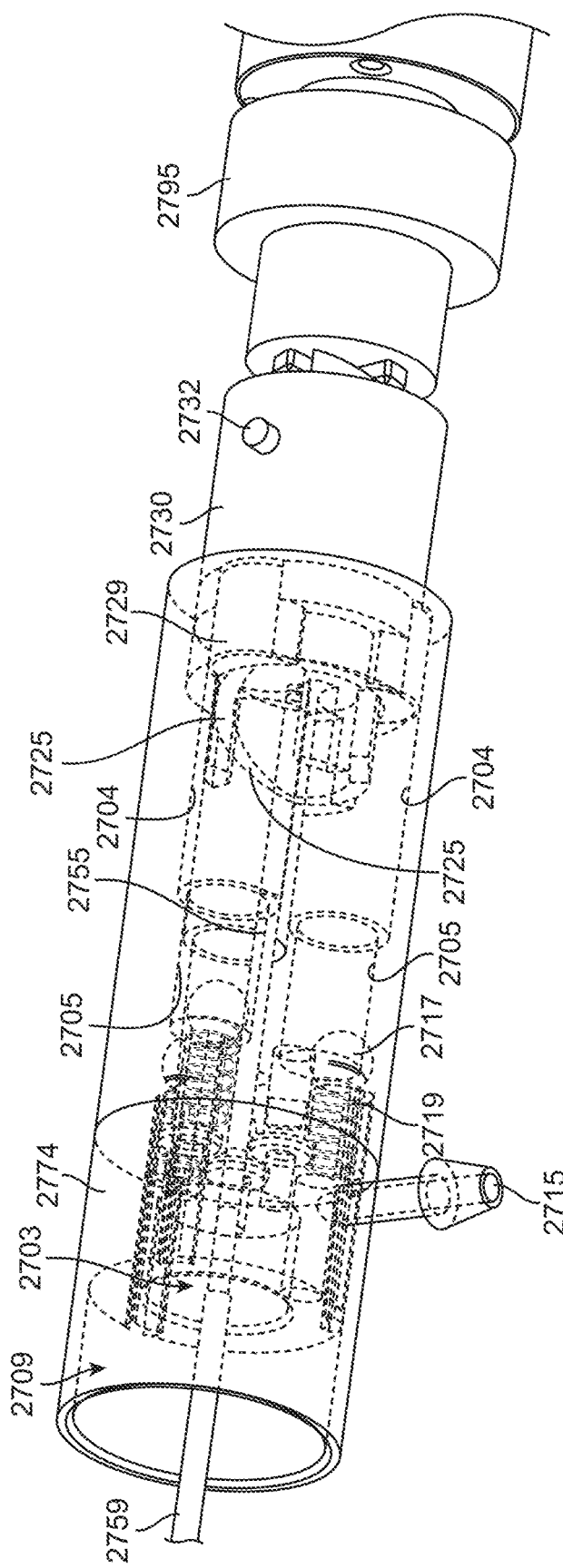
Figure 28L:
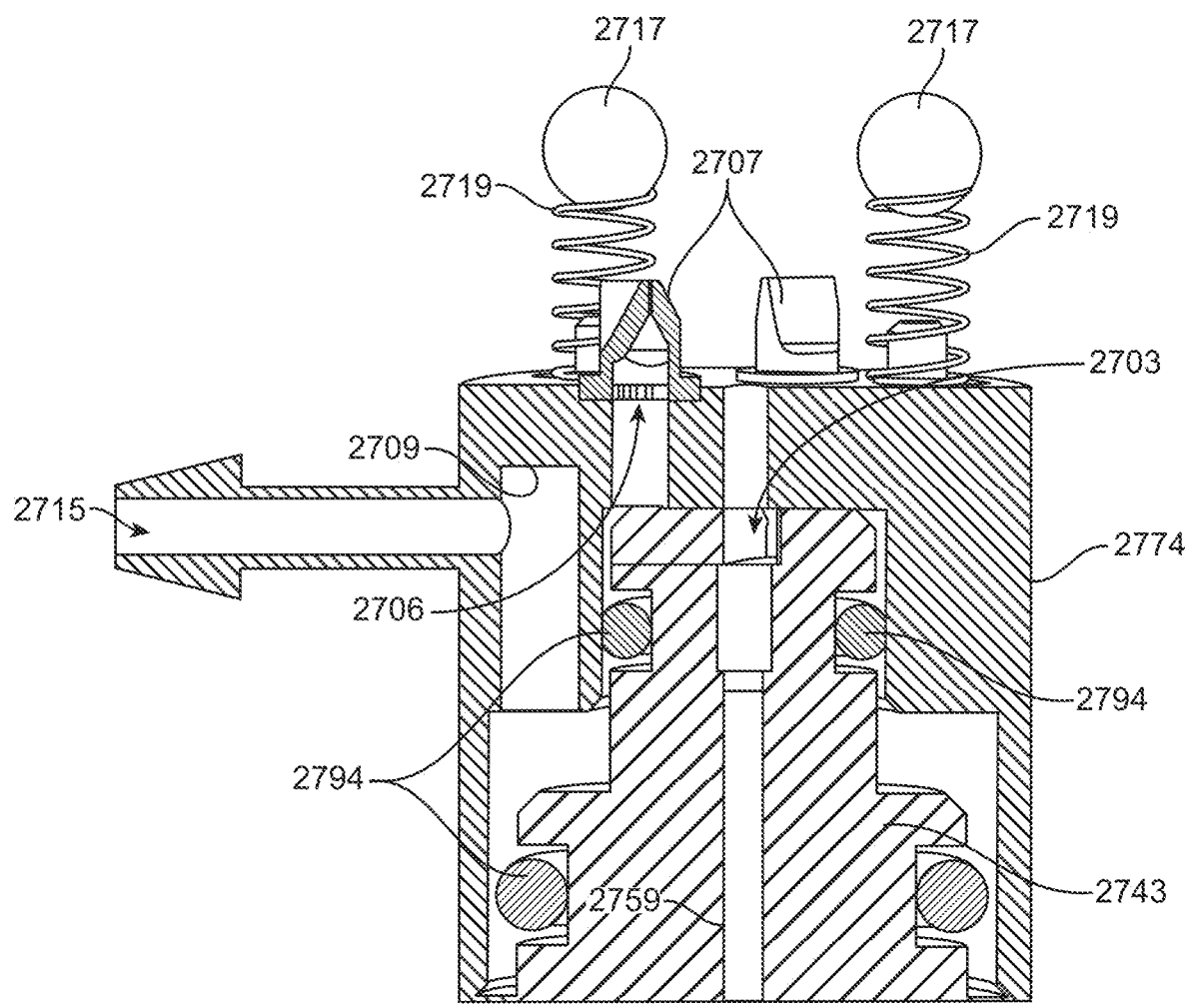
Figure 28M:
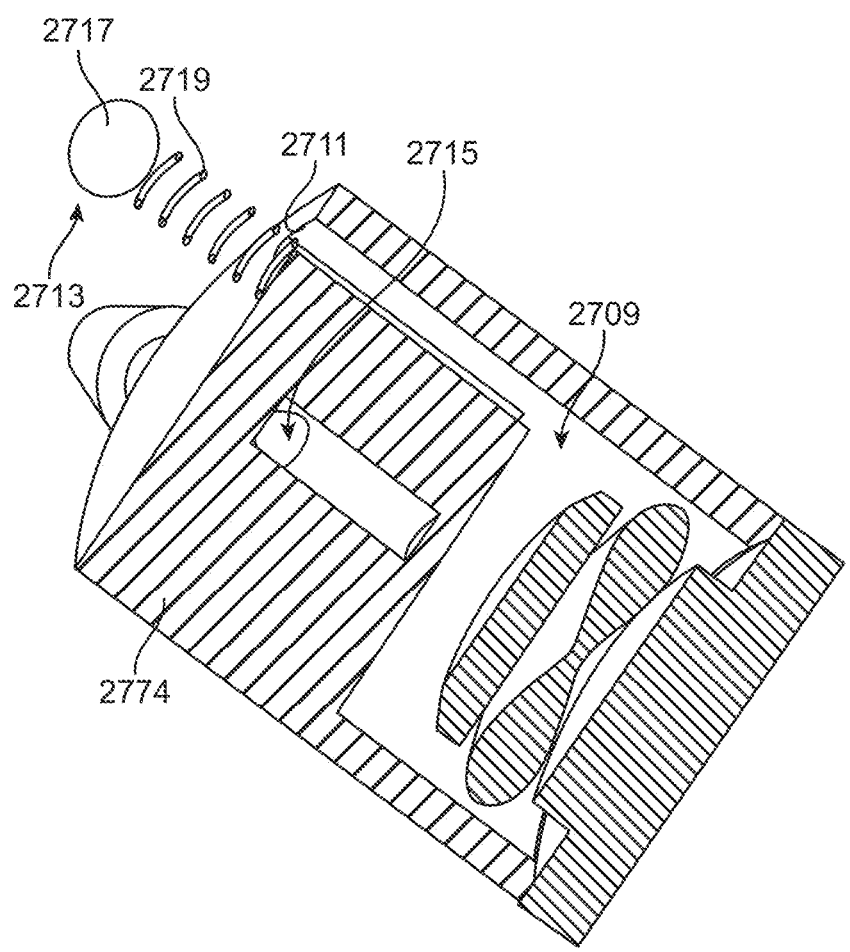
Figure 28N:
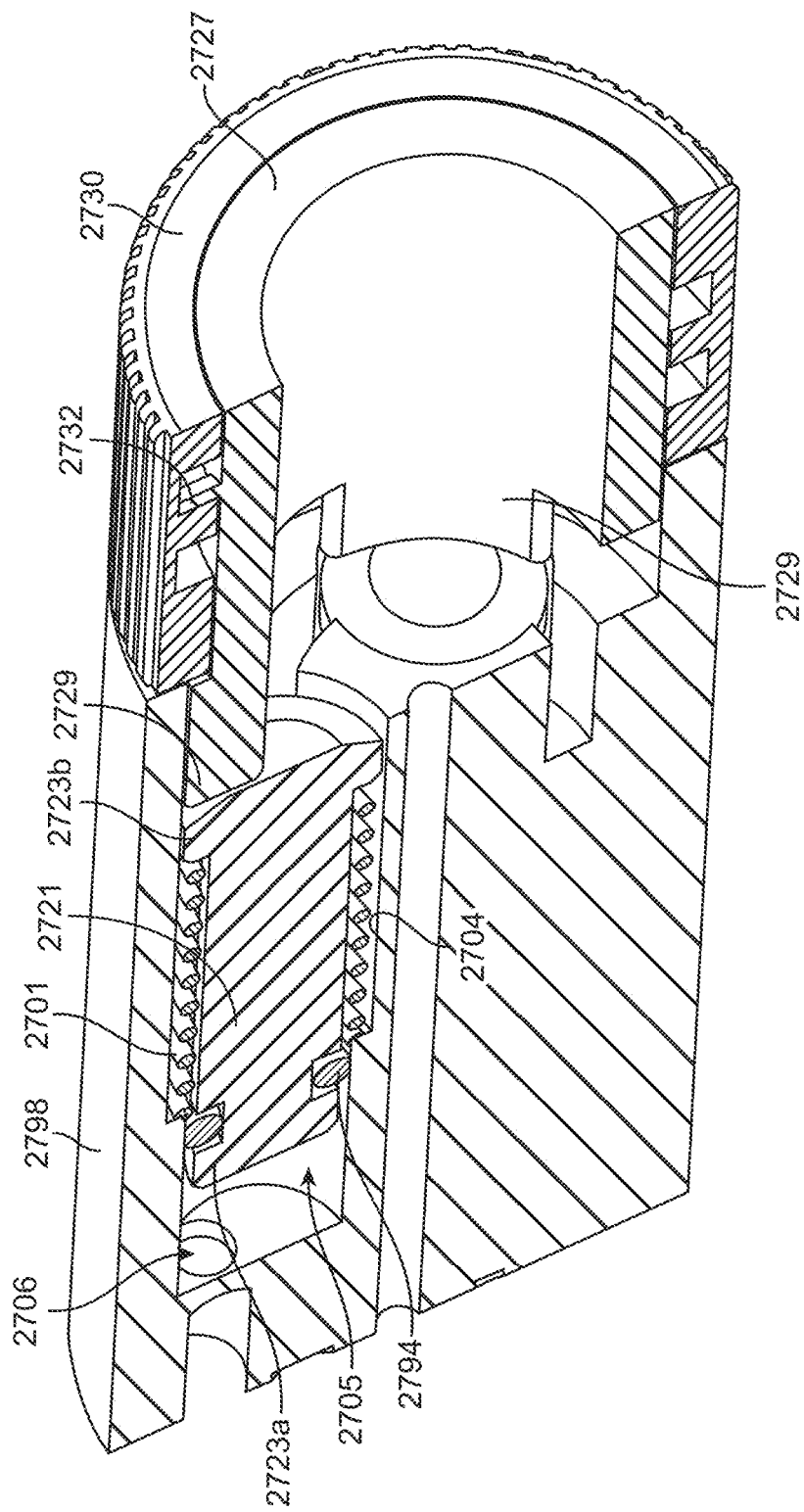

FIGS. 28A-28N illustrate a fully hand-held implementation of the device 2700. The device 2700 includes a hand-held unit 2760 having a distal elongate member or shaft 2761 coupled to and extending longitudinally from the housing 2762. The shaft 2761 can be an oscillating elongate member configured to slide reciprocally relative to the hand-held unit 2760. As described elsewhere herein, the shaft 2761 can be configured to undergo other types of movements including rotational, orbital, etc. Additionally, the oscillating elongate member can be tubular and have an internal lumen extending through it such that fluids can be delivered and/or aspirated through the oscillating elongate member. In other implementations, the oscillating elongate member is not tubular, but instead formed as a solid element. In this implementation, the oscillating elongate member can reciprocate within an outer tubular member and a gap between the shafts sized to receive and/or deliver fluids to the treatment site.

Again with respect to FIGS. 28A-28N, the shaft 2761 can be a vitrectomy-style cutting element having an elongate member 2755 extending through and coaxially arranged within the outer tube 2759 that is operatively coupled to a drive mechanism configured to slide the elongate member 2755 in a reciprocating, oscillating fashion as described above. The port 2764 near a distal end 2765 of the shaft 2761 communicates with a lumen 2763 forming a suction path leading from the port 2764 towards the vacuum manifold 2774. The lumen 2763 can extend through the elongate member 2755 to a proximal opening 2788 of the elongate member 2755. In other implementations, the lumen 2763 can extend through the outer tube 2759 between the inner surface of the outer tube 2759 and the outer surface of the elongate member 2755 to a proximal opening 2788 from the lumen 2763. The proximal opening 2788 communicates with a vacuum chamber 2703 of the vacuum manifold 2774. A vacuum can be applied within the vacuum manifold 2774 to aspirate the dissected tissue from the eye through the lumen 2763 such that material from the lumen 2763 empties into the vacuum chamber 2703.

As mentioned above, the device 2700 can include a suction or vacuum source that is found within an interior of the hand-held unit 2760. The vacuum source can be a pump having any of a variety of configurations, including but not limited to bellows mechanism, diaphragm pump, venturi pump, entrapment pump, positive displacement pump, regenerative pump, momentum transfer pump, micro pumps, or the like. The vacuum source need not be limited to a piston pump and can incorporate any of a variety of mechanisms configured to generate a negative pressure within the lumen of the elongate member.

As best shown in FIGS. 28E-28K, the vacuum manifold 2774 can be coupled to a piston manifold 2798 such that the vacuum chamber 2703 of the vacuum manifold 2774 is in fluid communication with one or more pumping chambers 2705 in the piston manifold 2798. The piston manifold 2798 houses pistons 2799 movable within the respective pumping chambers 2705 that are powered by a drive mechanism such as a motor 2756 located within the proximal end of the device. The one or more pistons 2799 powered by the motor 2756 generate a vacuum within the pumping chambers 2705 as well as the vacuum chamber 2703 for aspiration of material through the shaft 2761. In an implementation, the device 2700 can include one, two, or three, pistons 2799 movably positioned within respective pumping chambers 2705. It should be appreciated that any number of pistons 2799 can be positioned within respective pumping chambers 2705. Multiple pistons 2799 bouncing back and forth within their pumping chambers 2705 create a pulsatile vacuum or full vacuum delivered to a distal portion of the lumen of the elongate member in pulses of negative pressure. The pulsatile vacuum allows for application of full vacuum through the distal shaft 2761 without risk for collapse of the anterior chamber.

In some implementations, the cycles of negative pressure include short periods of vacuum interspersed by short periods of decreasing vacuum or no vacuum. In some implementations, the cycles of negative pressure include short periods of vacuum interspersed by short periods of positive pressure thereby resulting in a short regurgitation of fluid through the distal shaft 2761 during each cycle of piston movement. Whether or not positive pressure is applied between the pulses of vacuum, the pulsatile vacuum creates pulses of discontinuous negative pressure through the elongate shaft that can be between about 10 inHg up to about 30 inHg, preferably as close to full vacuum as possible. In some implementations, the device can create pulses of discontinuous negative pressure through the internal lumen of the elongate member at a cycling frequency. The device can also create pulses of discontinuous positive pressure having the same cycling frequency. Thus, the pulses of discontinuous negative pressure are interspersed by the pulses of discontinuous positive pressure. The cycling frequency of the pulses can be a relatively fast frequency, for example, at least about 0.5 Hz up to about 5000 Hz, or between 1 Hz and 4000 Hz, or between about 10 Hz up to about 2000 Hz. The pulses of discontinuous negative pressure aspirate a first amount of material into the internal lumen through the opening at the cycling frequency. The pulses of discontinuous positive pressure expel a second amount of material at the cycling frequency from the internal lumen through the opening. The volume of material being moved per cycle can vary, but is generally relatively small, for example, between about 0.1 mL up to about 1.0 mL, or approximately 0.5 mL. In some implementations, the nominal amount of fluid removed per pulse is about 100 microliters, or between 10 microliters up to about 1000 microliters. The second amount of material can be substantially less than the first amount of material within this general range of fluid amounts. The pulses of discontinuous negative pressure can be interspersed by discontinuous periods of lessening vacuum, no vacuum, or positive pressure at the same frequency.

The vacuum chamber 2703 is configured to be in fluid communication with the one or more pumping chambers 2705 via a respective opening 2706 regulated by a one-way valve 2707. The configuration of the one-way valve 2707 can vary including a duckbill valve, ball check valve, lift-check valve, stop-check valve and other types of valves that allow flow of fluid in a single direction and cut-off flow of fluid in the opposite direction. Movement of the pistons 2799 in a first direction within the pumping chambers 2705 creates a vacuum such that material from the eye is drawn into the lumen 2763 of the shaft 2761, emptied into the vacuum chamber 2703, and pulled through the one-way valve 2707 into the pumping chamber 2705. Movement of the pistons 2799 in a second, opposite direction within the pumping chambers 2705 expels material from the pumping chamber 2705 and out of the system. The material can be expelled from the system into a disposal enclosure coupled to an exit port as described elsewhere herein.

The vacuum manifold 2774 can additionally include an evacuation chamber 2709. The evacuation chamber 2709 is sealed off from the vacuum chamber 2703 such that material drawn into the system can be purged from the system without being pushed back out through the shaft 2761. The seal between the chambers 2703 and 2709 can be provided by one or more 0-rings 2794. As mentioned, the vacuum chamber 2703 is configured to be in fluid communication with the one or more pumping chambers 2705 through respective one-way valves 2707 positioned within openings 2706 (see FIG. 28L). The evacuation chamber 2709 is in fluid communication with each of the one or more pumping chambers 2705 through other openings 2711 regulated by respective valves 2713 (see FIG. 28M). The configuration of the valves 2713 can vary including a ball type check valve. As described above, movement of the pistons 2799 in a first direction within their respective pumping chambers 2705 (e.g. towards a proximal end of the device 2700) draws material from the vacuum chamber 2703 into the pumping chamber 2705 through the valves 2707. Movement of the pistons 2799 in a second, opposite direction within their respective pumping chambers 2705 (e.g. towards the distal end of the device 2700) forces the material into the evacuation chamber 2709 through the valve openings 2711. During this purge of material, the one-way valves 2707 between the one or more pumping chambers 2705 and the vacuum chamber 2703 prevents the backflow of material into the vacuum chamber 2703, the lumen 2763, and out the cutting tip. However, the openings 2711 between the one or more pumping chambers 2705 and the evacuation chamber 2709 allows for the material to freely enter the evacuation chamber 2709 and ultimately out an exit port 2715 of the evacuation chamber 2709 at least until flow is cut off by the valves 2713. As described above, movement of the pistons 2799 in a proximal direction creates a vacuum within the pumping chamber 2705. The ball 2717 of the valve 2713 is pushed proximally by the spring 2719 away from opening 2711 between the pumping chamber 2705 and the evacuation chamber 2709 thereby opening the valve 2713. Upon movement of the pistons 2799 in a distal direction, fluid pressure builds within the pumping chamber 2705 increasing fluid pressure within the chamber and urging the material towards the opening 2711 of the valve 2713. The ball 2717 of the valve 2713 is pushed distally against the spring 2719 such that the spring 2719 compresses and the ball 2717 is urged against the valve opening 2711 thereby closing the valve (see FIG. 28M). The pumping chambers 2705 are substantially devoid of material upon closure of the valve 2713. In some implementations, one or more of the valves may be slightly compliant such as a silicone valve like a duckbill valve. Compliant valves may deform as a reverse positive pressure is imparted on them. If the valve between the vacuum chamber 2703 and the pumping chamber 2705 is a compliant valve, then as the piston is travelling distally and generating positive pressure to evacuate the material from the pumping chamber 2705, the positive pressure may cause a deformation of the compliant valve. The deformation may cause a small purge or regurgitation of an amount of fluid out the shaft 2761. This regurgitation may occur on every back and forth cycle of the piston 2799. In some embodiments, the regurgitation may be optimized further by the design of the pumping chamber 2705. In the pumping chamber 2705, the outlet opening connecting the pumping chamber 2705 to the evacuation chamber 2709 may be located, for example, on the side of the chamber and configured such that the piston 2799 may travel beyond the outlet opening. In this embodiment, after the piston 2799 has moved distally beyond the outlet opening there is no other route for fluid evacuation. Therefore, as the pistons 2799 continue to travel distally creating a moment of positive pressure within the pumping chamber 2705 after closure of the valves 2713 that causes a short regurgitation of material at the distal end of the shaft 2761.

As best shown in FIG. 28J and also FIG. 28N, each of the pistons 2799 can include an elongate central piston rod 2721 surrounded by a spring 2701 extending between piston heads 2723a, 2723b. A distal piston head 2723a and sliding O-ring seal 2794 are positioned within the pumping chamber 2705. The piston rod 2721, spring 2701, and proximal piston head 2723b are positioned within a piston chamber 2704 within the piston manifold 2798 located proximal to the pumping chamber 2705. The distal piston head 2723a, sliding seal 2794, and piston rod 2721 are capable of sliding within the pumping chamber 2705 from a proximal end region to a distal end region to create the vacuum pressure. The pumping chamber 2705 has an inner dimension that is smaller than the piston chamber 2704 and the outer dimension of the spring 2701. Thus, as the piston 2799 move towards the distal end region of the pumping chamber 2705, the spring 2701 gets compressed within the piston chamber 2704 between the proximal piston head 2723b and the lower end of the pumping chamber 2705.

The spring 2701 is biased to urge the piston 2799 proximally towards a proximal end of the pumping chamber 2705. A rotating cam 2769 positioned proximal to the pistons 2799 is configured to urge the pistons 2799 distally towards the distal end of their respective pumping chambers 2705. As the cam 2769 rotates, it applies a distally-directed force sequentially against the proximal piston heads 2723b of the pistons 2799. The springs 2701 of the pistons 2799 are, in turn, sequentially compressed. Upon further rotation of the cam 2769, the distally-directed force against the proximal piston heads 2723 is sequentially removed and the springs 2701 sequentially urge the pistons 2799 backwards creating a vacuum within the respective pumping chambers 2705 through the one-way valves 2707.

As best shown in FIGS. 28J-28K and also FIGS. 28E-28G, a gear head 2752 of the motor 2756 can be coupled to the rotating cam 2769 via a motor coupler 2795. The motor coupler 2795 can have a bore 2789 in a proximal end configured to receive the gear head 2752 and one or more projections 2796 on a distal end. The projections 2796 are configured to abut and engage with corresponding wedged-shaped projections 2797 on the proximal end of the cam 2769. The cam 2769 rotates as the gear head 2752 rotates. A distal end of cam 2769 has a cam surface 2725 configured to provide reciprocal linear motion of the pistons 2799. The cam surface 2725 can be elliptical, eccentric, egg, or snail-shaped. During a first fraction of rotation of the cam 2769, the proximal piston heads 2723b slide along the ramped portion of the cam surface 2725 and the piston 2799 is moved distally along the longitudinal axis of the device. During a second fraction of rotation of the cam 2769, the proximal piston heads 2723b slide past the cam surface 2725 such that the distally-directed force against the pistons 2799 by the cam 2769 is released. The spring 2701 surrounding the piston rod 2721 urges the proximal piston head 2723b in a proximal direction towards the proximal end region of the piston chamber 2704. A complete revolution of the cam 2769 therefore allows for axial movement of each piston 2799 in succession. Movement of the elongate member 2755 can occur using a similar rotating cam mechanism, as will be described in more detail below.

As best shown in FIG. 28N, a piston stop 2727 can be coupled to a proximal end region of the piston manifold 2798. The piston stop 2727 can be a generally cylindrical element surrounding the rotating cam 2769. A distal end region of the piston stop 2727 can define one or more projections 2729 configured to project into a proximal end region of each of the piston chambers 2704 in the piston manifold 2798. The projections 2729 abut against the proximal piston heads 2723b of respective pistons 2799 when positioned at a proximal-most end region of their respective piston chambers 2704. For example, if the device 2700 includes three pistons 2799 positioned in three piston chambers 2704, the piston stop 2727 includes three projections 2729 configured to abut against the proximal piston head 2723b of each of the three pistons 2799. The piston stop 2727 provides a hard stop to the linear travel of the pistons 2799 in a proximal direction upon expansion of the springs 2701 and thus, the overall volume of the pumping chamber 2705 that can be achieved. The relative position of the projections 2729 within the piston chambers 2704 can be adjustable. In some implementations, an adjustment ring 2730 can be positioned around an outer surface of the piston stop 2727 and available to a user through one or more windows 2731 in the housing of the hand-held portion 2760 (see FIGS. 28A-28B). The adjustment ring 2730 can have a threaded inner surface configured to engage with a corresponding pin 2732 on an outer surface of the piston stop 2727. The pin 2732 is configured to slide within the threads of the adjustment ring 2730 such that the piston stop 2727 travels axially along the longitudinal axis of the device. As the piston stop 2727 is adjusted to be positioned further distal relative to the piston manifold 2798, the projections 2729 extend further into the piston chambers 2704 and limit the linear travel of the pistons 2799 in the proximal direction upon expansion of the springs 2701. This, in turn, limits the size of the pumping chamber 2705. As the piston stop 2727 is adjusted to be positioned more proximally relative to the piston manifold 2798, the projections 2729 are withdrawn from the piston chambers 2704 and do not limit (or limit to a lesser degree) the linear travel of the pistons 2799 in a proximal direction upon expansion of the springs 2701. This, in turn, maximizes the size of the pumping chamber 2705.

The hand-held portion 2760 of the device 2700 can be formed of a relatively rigid, lightweight material(s). At least a portion of the hand-held portion 2760 can be removable such that the device 2700 includes a durable portion configured to be reused (e.g. the motor 2756 and related components) and a disposable portion (e.g. the components coming into contact with human tissue or fluids). In some implementations, the hand-held portion 2760 includes a disposable front housing portion configured to couple with a durable back housing portion. The two housing portions can couple together using a variety of mechanisms such as threads, snap-lock, and the like. The coupling mechanism can include a release button configured to uncouple the two housing portions.

As discussed above, the amount of pulsatile vacuum can be adjusted by limiting the travel of the pistons in a rearward direction such as with a piston hard stop. In some implementations, the relative relationship of the disposable to reusable portions is adjustable and, in turn, can limit the distance the pistons can travel backwards. For example, the further the reusable portion is positioned onto the disposable portion, the more limited the piston travel is due to the piston hard stop. The position of the piston stop can be adjustable to provide a plurality of selectable vacuum settings. In some procedures or certain steps of a procedure, higher pressures may be more desirable than in other procedures or steps of the procedure. The higher pressure can be selected, for example, by actuating the piston stop to a wider setting such that the piston can travel a longer distance per cycle and maximum vacuum achieved. In some implementations, the piston stop position can be toggled between a "high vacuum" position and a "low vacuum" position by clicking an adjustor. In other implementations, the piston stop positioned can be "dialed in" to any of a plurality of vacuum settings that are conveniently selected during use.

In some implementations, the vacuum source can create a sudden rise in vacuum forming a vacuum profile that causes the cornea and the eye to effectively "bounce" up and down during application of pulsed vacuum. For example, when the pistons 2799 are sprung backwards they can create the sudden rise in vacuum forming a vacuum profile that resembles a "saw tooth" (i.e. suction-pause-suction). Limiting the backwards travel of the pistons 2799 inside their respective pumping chambers 2705 can reduce the amount of suction impact or shock that is created each time the pistons are sprung backwards. The piston limit thereby limits the maximum suction created with each piston travel reducing the impact this abrupt suction can have on the eye. The aspiration forces created with each backwards travel of the piston 2799 can be greater than 500 mmHg up to about 700 mmHg.

In some implementations, the device is limited from achieving maximum vacuum by incorporating a feature that automatically bypasses the shaft 2761 depending on whether a threshold vacuum is reached. For example, a bleed valve or other bypass mechanism can be incorporated to prevent a threshold amount of vacuum from being applied at a distal opening of the shaft 2761 and into the eye. A bypass to turn on or off the suction can limit the maximum amount of vacuum that can be generated within the eye even if the opening into the shaft 2761 is clogged. This bypass can prevent the vacuum from building in the event of a blockage to create less surge upon removal of that blockage. The bypass mechanism can be adjustable or selective such that a user can choose whether or not they want the potential for maximum vacuum or something less than maximum vacuum applied.

Figure 32A:
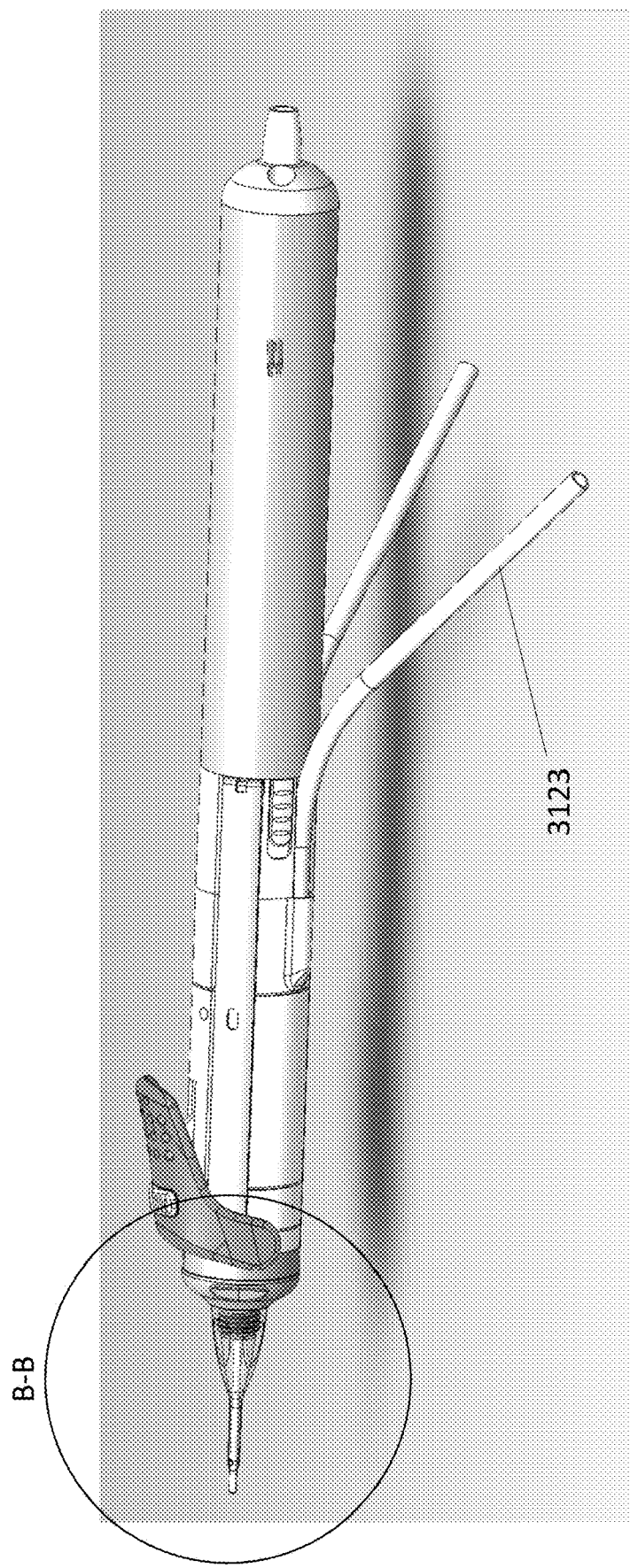
FIG. 32A shows a perspective view of a device having an elongate member.
Figure 32B:
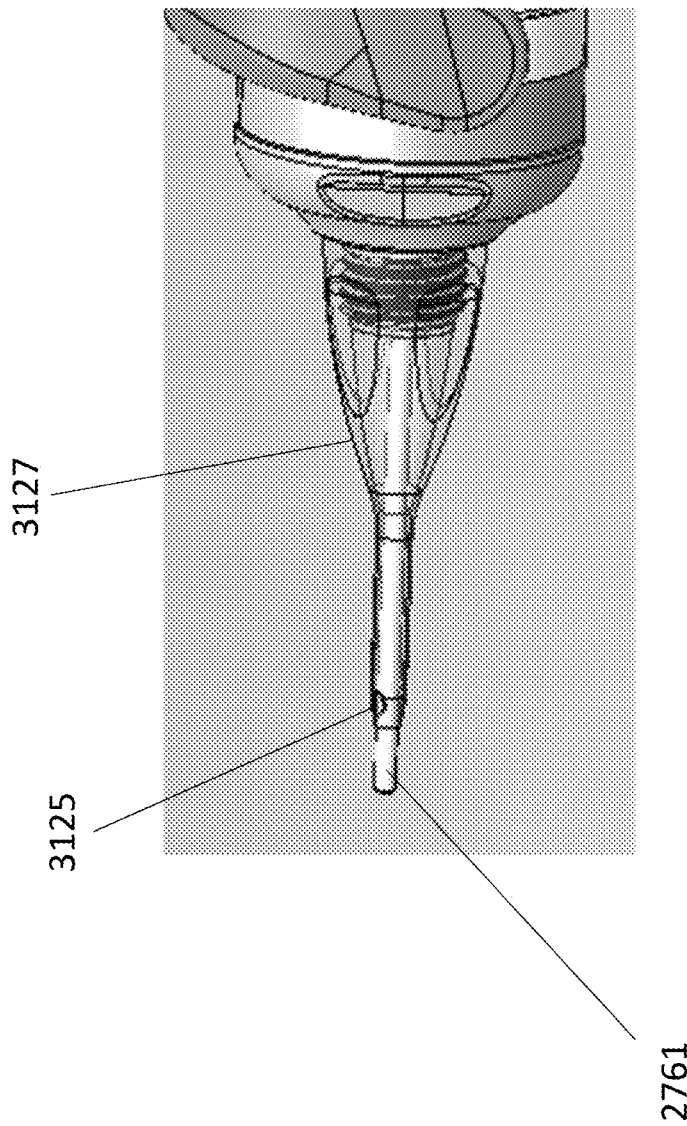
FIG. 32B is a detailed view of FIG. 32A taken along circle B-B.

As mentioned above, the shaft 2761 can include an irrigation sleeve configured to deliver irrigation to the work site. FIGS. 32A-32B illustrates an implementation of the device having an irrigation sleeve 3127 near a distal end region of the shaft 2761. The irrigation sleeve 3127 can include one or more irrigation openings 3125 configured to deliver fluid from the irrigation lumen 3123 to the eye during use. In some implementations, the device can incorporate a compliant element in communication with the irrigation flow path. The compliant element can be a balloon or other fillable element or reservoir configured to store an amount of fluid from the irrigation lumen 3123. The compliant element can fill with irrigation fluid such that in the event of a blockage and a sudden rush of vacuum through the distal opening of the shaft 2761, the irrigation fluid stored up in the compliant element can be available to fill in the volume removed by the increased vacuum. The fluid from the compliant element can be pulled into the eye upon the increase in negative pressure to maintain a balance in pressure within the eye to avoid damage or collapse of the anterior chamber.

As described elsewhere herein, the elongate member or shaft of the devices described herein can be oscillated relative to the hand-held portion of the device by a drive mechanism operatively coupled to the elongate member. The drive mechanism can be powered via a cable extending through the housing or by one or more batteries. Power can be applied to the device 2700 via one or more actuators or inputs such as a trigger, button, slider, dial, keypad, touchscreen, footswitch, or other input device as described elsewhere herein. The input and power can be positioned on the device itself or remote from the device. The device can further include a control processor responsive to the user input and power. The control processor can control one or more aspects of the drive mechanism. The control processor can be programmable and accept user input to adjust various adjustable functions of the device (i.e. travel distance of the elongate member, oscillation frequency of the elongate member, extension speed profile, retraction speed profile, maximum extension speed, maximum retraction speed of the elongate member, vacuum level, etc.). The control processor can be programmed by an input on the device itself or programmed remotely such as by an external computing device having an input. The control processor can operate according to program instructions stored in a memory.

Control of the drive mechanism can be completed through the use of a motion controller, electronic speed controller, or the like. The actuator or input for the motion controller of the can be an on/off sort of input to initiate cutting and/or vacuum. Alternatively, the input for the motion controller can be a multi-way input that causes, for example, the motor 2756 to spin faster depending on degree of actuation of the input (e.g. pressing further down on a button, dialing up a dial, tapping a displayed key on a touchpad, or sliding a further distance in a direction relative to the housing). The controller can be programmed (e.g. remotely or on the device itself) to have a minimum and/or maximum speed upon actuation of the input, as will be described in more detail below.

FIGS. 33A-33C illustrate different configurations of an implementation of a multi-way input 3125, such as a trigger, on the device configured to control various functions of the device. The input 3125 can have a plurality of positions configured to turn on or off (or increase or decrease) one or more functions of the device. For example, the input 3125 can have a resting position as shown in FIG. 33A. The user can actuate the input 3125 to move into a first actuated position (e.g. a partially depressed position) configured to start or increase at least one or more functions of the device (see FIG. 33B). The first actuated position can turn on both vacuum and oscillation of the distal shaft 2761 thereby providing vacuum-plus-cutting function. The input 3125 can have a second actuated position (e.g. fully depressed position) configured to pause or decrease one or more functions of the device (see FIG. 33C). For example, the input 3125 in the second actuated position can suspend oscillation of the shaft 2761 while the vacuum through the shaft 2761 continues thereby providing a vacuum-only function.

Various configurations of the input are considered herein. As an example configuration, the input 3125 can be mechanical such that it couple to a rod 3127 that is movable along a longitudinal axis of the device as the input 3125 is actuated into one of a plurality of positions (shown in FIGS. 33B-33C). For example, when the input 3125 is moved from the resting position into the first actuated position, the input 3125 can move the rod 3127 such that a proximal end of the rod 3127 extends a first distance into a proximal portion of the hand-held portion of the device (FIG. 33B). When the input 3125 is moved from the first actuated position into the second actuated position, the input 3125 can move the rod 3127 such that the proximal end of the rod 3127 extends a second distance into the proximal portion of the handheld portion of the device (FIG. 33C). The proximal end of the rod 3127 can interact with an element within the handheld portion of the device configured to change the speed of the motor configured to oscillate the elongate shaft 2761, for example, by a potentiometer.

The rod 3127 in addition to changing the speed of oscillation can prevent movement of the shaft 2761 altogether. As described above, movement of the rod 3127 can cause it to change the speed of the motor by interacting with a potentiometer or other feature. Movement of the rod 3127 in a proximal direction P can also move the shaft 2761 in a proximal direction thereby preventing the proximal end of the shaft 2761 from interacting with the drive mechanism configured to cause the shaft 2761 to oscillate (e.g. camming teeth). FIGS. 34A-34C correspond to FIGS. 33A-33C and FIGS. 35A-35C. Each of the figures illustrate how movement of the actuator 3125 and the rod 3127 affect movement of the shaft 2761 relative to a camming mechanism. In the resting state of the actuator 3125 shown in FIG. 34A, the rod 3127 is in a distal-most position and moved away from a proximal spline 3162 of the shaft 2761. Under normal operation and as described elsewhere herein, the rotating cam 3169 can continuously spin. As it spins, the rotating cam 3169 causes the teeth 3132 of the cam follower 3190 to engage and effectively pull the cutter spline 3162 backward until it reaches the step 3933 (see FIGS. 35A-35C) at which point the force of the spring 3135 urges the shaft 2761 forward or in a distal direction D. The shaft 2761 oscillates back and forth as the cam 3169 spins. Upon full actuation of the actuator 3125, the rod 3127 is moved further in a proximal direction P until a feature 3163 of the rod 3127 engages with the spline 3162 of the shaft 2761 (see FIGS. 34C and 35C). The rod 3127 pulls the spline proximally. The movement disengages the cam 3169 from the cam follower 3190 preventing the teeth 3132 from engaging such that no motion of the shaft 2761 occurs.

In some implementations, the device 2700 is an all-in-one device in which the only linkage to the instrument may be for power. Thus, the all-in-one device may not have any foot pedal or other linkage for control.

The device 2700 may also battery-powered. The battery can be incorporated within a region of the housing, either internally or coupled to a region of the housing such as within a modular, removable battery pack. The battery can have different chemical compositions or characteristics. For instance, batteries can include lead-acid, nickel cadmium, nickel metal hydride, silver-oxide, mercury oxide, lithium ion, lithium ion polymer, or other lithium chemistries. The device can also include rechargeable batteries using either a DC power-port, induction, solar cells, or the like for recharging. Power systems known in the art for powering medical devices for use in the operating room are also to be considered herein. In some implementations, rather than the battery back mounted on or in the handle, which can increase the size of the handle, the battery pack can be mounted elsewhere such as on a user's arm or wrist of the arm holding the instrument during a procedure. A short cable connector can connect the mounted battery back to the device such that only this linkage extends from the handle of the device 2700 during use. Thus, no foot pedal or other tethering connection need be linked to the device 2700. This can provide the user with more portability, flexibility, and freedom of movement and without worrying about catching cables or other tethers during use.

As mentioned above, the devices described herein can include a shaft configured to be inserted into the eye in a minimally-invasive manner to cut, aspirate, and/or inject material in the eye. The shaft can be a vitrectomy-style cutting element having a hollow, elongate member extending through an outer member with a side opening configured to capture and cut pieces of tissue. The shaft can also include a phacoemulsification ("phaco") style tip, which also includes a movable elongate member with or without an outer member. Oscillating movements of the elongate member can occur using any of a variety of mechanisms, such as a rotating cam element as described elsewhere herein. The oscillating movements can be created in a manner that avoids the deleterious effects typical of phacoemulsification on the delicate eye tissues such as corneal endothelial cells.

Phacoemulsification can incorporate two main methods of action: 1) mechanical jack hammering, and 2) cavitation. In the case of jackhammering, the oscillating movements of the tip mechanically knocks into the lens tissue at a high speed to break up the tissue into ever smaller fragments. Cavitation involves the creation of a vacuum and fluid bubbles during oscillating movements of the tip. As the phaco tip retracts in the fluid, the speed of its movement is so fast that it cavitates, or creates a vacuum created by the retracting tip causing the formation of bubbles as gas is drawn out of the fluid. These bubbles implode under very high temperature (e.g. 3000° C.) and very high pressure (e.g. 10,000 atm). It is generally thought that the combination of high temperatures and high pressure helps to break down the lens tissue fragments. While the role cavitation plays in breaking up the lens material is debatable, the role cavitation plays as the primary driver behind the deleterious effects of phacoemulsification on the surrounding lens tissue during cataract surgery is not.

High temperatures, shock waves, and the creation of free-radicals in the eye are of concern to the health of the corneal endothelial cells.

In an implementation, one or more of the devices described herein can include an oscillating tip configured to move in a manner that reduces, attenuates, or prevents problems of cavitation during phacoemulsification. The oscillating tip can be incorporated in an "all-in-one" sort of device having a vacuum source within the handle to apply pulsatile vacuum. Alternatively, the oscillating tip can be incorporated in a device used in connection with another device configured to apply pulsatile vacuum remotely. As described above, the various features and functions of the devices described herein can be applied to conventional devices and systems known in the art to be useful for cutting, fragmenting, emulsifying, or otherwise impacting tissues at or near a surgical site. For example, the pulsatile vacuum and/or asymmetric motion profiles described herein can be incorporated into phacoemulsification systems and vitrectomy systems known in the art. For example, the features described herein can be incorporated as an additional hardware or software feature of the phacoemulsification systems that are conventionally used to cause oscillation of an elongate shaft in the ultrasonic range of frequencies (e.g. above 20,000 Hz).

Figure 29G:
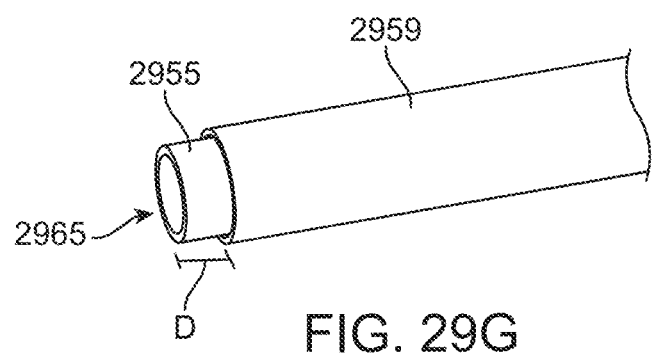
FIGS. 29G and 29H are partial views of an elongate member having inner and outer tubes in an extended and a retracted state, respectively.

FIGS. 29A-29C illustrate an implementation of a device 2900 having a hand-held portion 2960 coupled to a distal shaft 2961. The distal shaft 2961 can include an elongate member 2955 configured to oscillate relative to the hand-held portion 2960. The elongate member 2955 can, but need not, extend through a tubular outer member 2959 (see FIGS. 29G-29H). The elongate member 2955 can include a distal tip 2965. The device 2900 can include a drive mechanism operatively coupled to the distal shaft 2961 and configured to drive movement of the tip 2965. As will be described in more detail below, the drive mechanism can be operatively coupled to the elongate member and configured to oscillate the elongate member. When in use, the drive mechanism is capable of retracting the elongate member in a proximal direction with a retraction speed profile and advancing the elongate member in a distal direction with an extension speed profile. The retraction speed profile can be different from the extension speed profile.

In some implementations, the elongate member 2955 can be connected to a hub 2987. The hub 2987 can have camming surfaces 2992 on its distal surface that engages with a rotating cam 2969. The proximal surface of the hub 2987 can be connected to a spring 2935 that pushes the hub 2987 distally. The distal shaft 2961 can include an elongate member 2955 extending through an outer member 2959, although it should be appreciated that no outer member 2959 is necessary. The elongate member 2955 is also connected to an orientation locking feature 2928 such as a rectangular block that prevents the elongate member 2955 and the hub 2987 from rotating. As the rotating cam 2969 rotates, the camming surfaces 2992 cause the hub 2987 to move proximally, compressing the spring 2935 further. The camming surfaces 2992 have a step 2933 that allows the hub 2987 to drop forward (i.e. distally) again at a certain point in the rotation. At this point, the spring 2935 pushes the hub 2987 quickly forward until the camming surfaces 2992 engage again. Through such a mechanism, the tip 2965 of the elongate member can retract with a retraction speed profile that is at least in part a function of the rotational speed of the rotating cam 2969. The rotational speed of the rotating cam 2969 can be controlled so that the maximum tip retraction speed remains below a 'cavitation threshold speed' for generating cavitation bubbles in the eye. The tip 2965 of the elongate member can then extend with an extension speed profile that is at least in part a function of the force of the spring 2935 and mass of the tip assembly. In this way, the average retraction speed can be slow, i.e. below the cavitation threshold, but the average extension speed can be fast, i.e. close to or higher than the average retraction speed of a typical phacoemulsification tip. Thus, the benefits of mechanical jackhammering can be achieved while the deleterious effects of cavitation are substantially avoided.

Figure 30A:
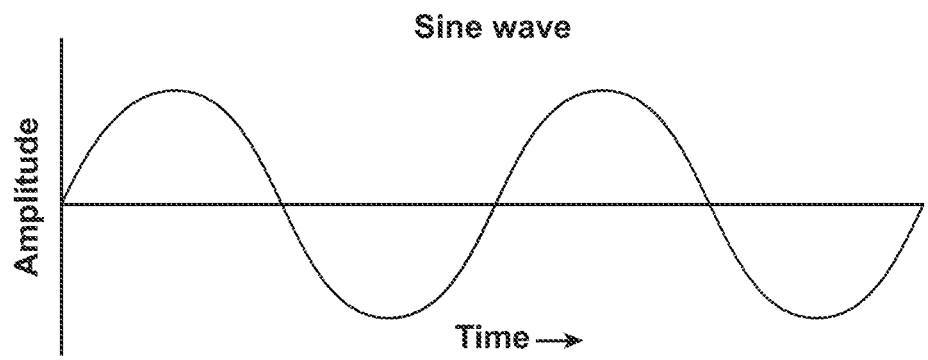
FIG. 30A shows a symmetric, sinusoidal motion profile of an elongate member of conventional phacoemulsification systems.
Figure 30B:
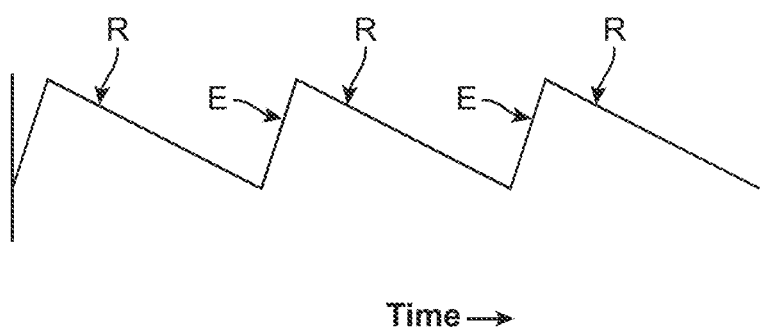
FIG. 30B shows an asymmetric, non-sinusoidal motion profile of an elongate member.
Figure 30C:
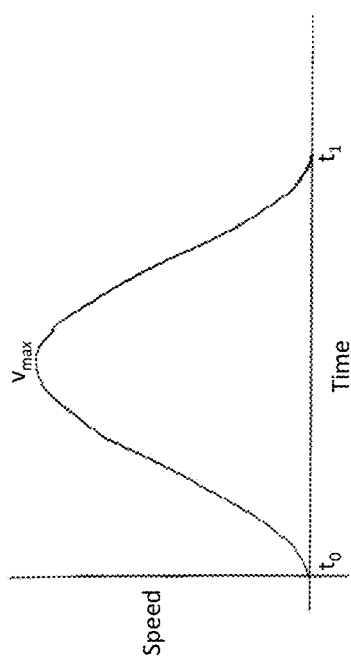
FIG. 30C shows a symmetric motion profile for an elongate member where an extension speed profile is the same as a retraction speed profile of the elongate member.

FIGS. 30A and 30C illustrate typical motion profiles of conventional phacoemulsification tips. Conventional phacoemulsification tips have a substantially sinusoidal motion profile in which the average speed of the tip is substantially the same during proximal retraction as during distal extension (see FIG. 30A). In contrast, the oscillating elongate member of the devices described herein have a generally non-sinusoidal motion profile in which the average tip speed of the retraction speed profile and the average tip speed of the extension speed profile can be substantially different providing an overall asymmetric movement profile for the oscillating elongate member (see FIG. 30B). Additionally, conventional phacoemulsification tips have maximum tip speed ($V_{maxR}$) of the retraction speed profile R that is substantially the same as the maximum tip speed ($V_{maxE}$) of the extension speed profile E and thus, their motion profiles substantially overlap (see FIG. 30C). The oscillating elongate member of the devices described herein have maximum tip speed ($V_{maxR}$) of the retraction speed profile R that is substantially the lower than the maximum tip speed ($V_{maxE}$) of the extension speed profile E and thus, their motion profiles do not substantially overlap (see FIG. 30D).

Figure 30D:
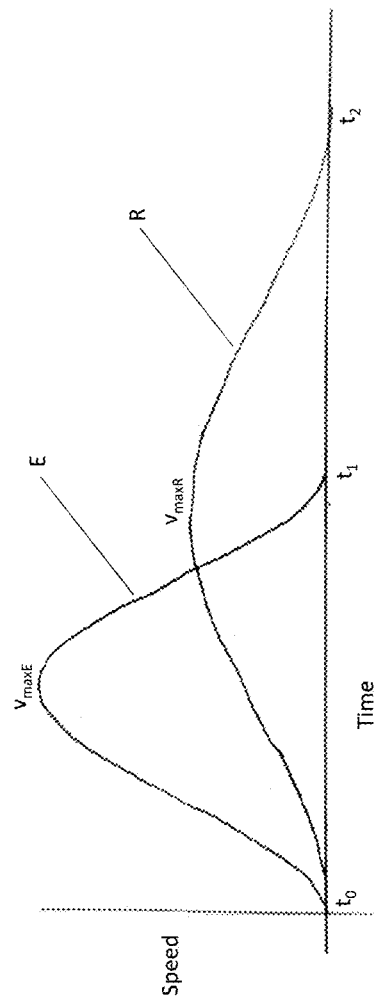
FIG. 30D shows an asymmetric motion profile for an elongate member where an extension speed profile differs from a retraction speed profile of the elongate member.

FIG. 30C illustrates a motion profile provided by a conventional phacoemulsification machine in which the extension and retraction speed profiles are substantially the same. For example, a 40,000 Hz phaco machine having a 0.1 mm amplitude speed may have a $V_{max}$ of approximately 12.6 meters/second where the time $T_1$ is approximately 0.0125 ms. FIG. 30D illustrates a motion profile provided by the devices described herein. The $V_{maxE}$ may be substantially the same as $V_{maxE}$, of a conventional phacoemulsification machine, but the $V_{maxR}$ may be substantially lower such that full retraction is complete at time $T_2$. Thus, the device may have a lower $V_{avg}$.

Figure 30E:
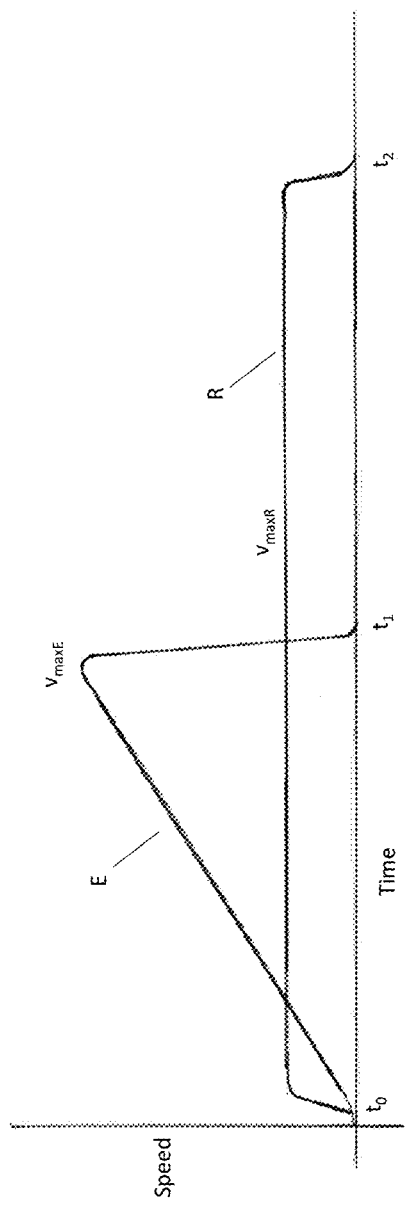
FIGS. 30E-30F show additional examples of extension speed profiles and retraction speed profiles of an elongate member where the profiles are different.
Figure 30F:
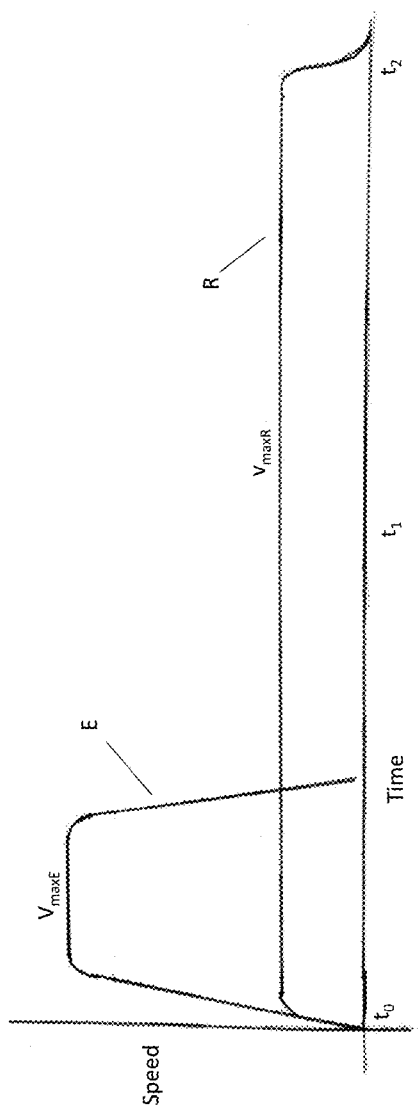

FIGS. 30E-30F illustrate additional asymmetric motion profiles considered herein. The extension speed E can increase linearly to $V_{maxE}$ as the spring force compels the elongate member forward until it reaches its stroke limit and drops back off to zero before being retracted. As the elongate member is retracted (e.g. as the cam rotates it pulling the elongate member back at a roughly constant speed), the retraction speed R increases to $V_{maxR}$ before slowing back down to a stop. The retraction speed profile R can form a plateau during which time the retraction speed is roughly constant. Retraction phase is complete at time $T_2$, which is longer than the time $T_1$ it took to complete the extension phase. There can include period of dwell or a pause between extension and retraction phases. The $V_{maxE}$ can be roughly the same as conventional phaco machines (e.g. between about 8 to 12 meters/second). The $V_{maxR}$ can be much lower than conventional phaco machines (e.g. less than about 0.02 meters/second). It should be appreciated that speeds of extension and retraction can vary and that any of a number of non-sinusoidal tip motion profiles are considered herein. In some implementations the $V_{maxE}$ can be between about 2 meters/second and 50 meters/second and the $V_{maxR}$ can be between about 0.001 meters/second and 2 meters/second.

Figure 30G:
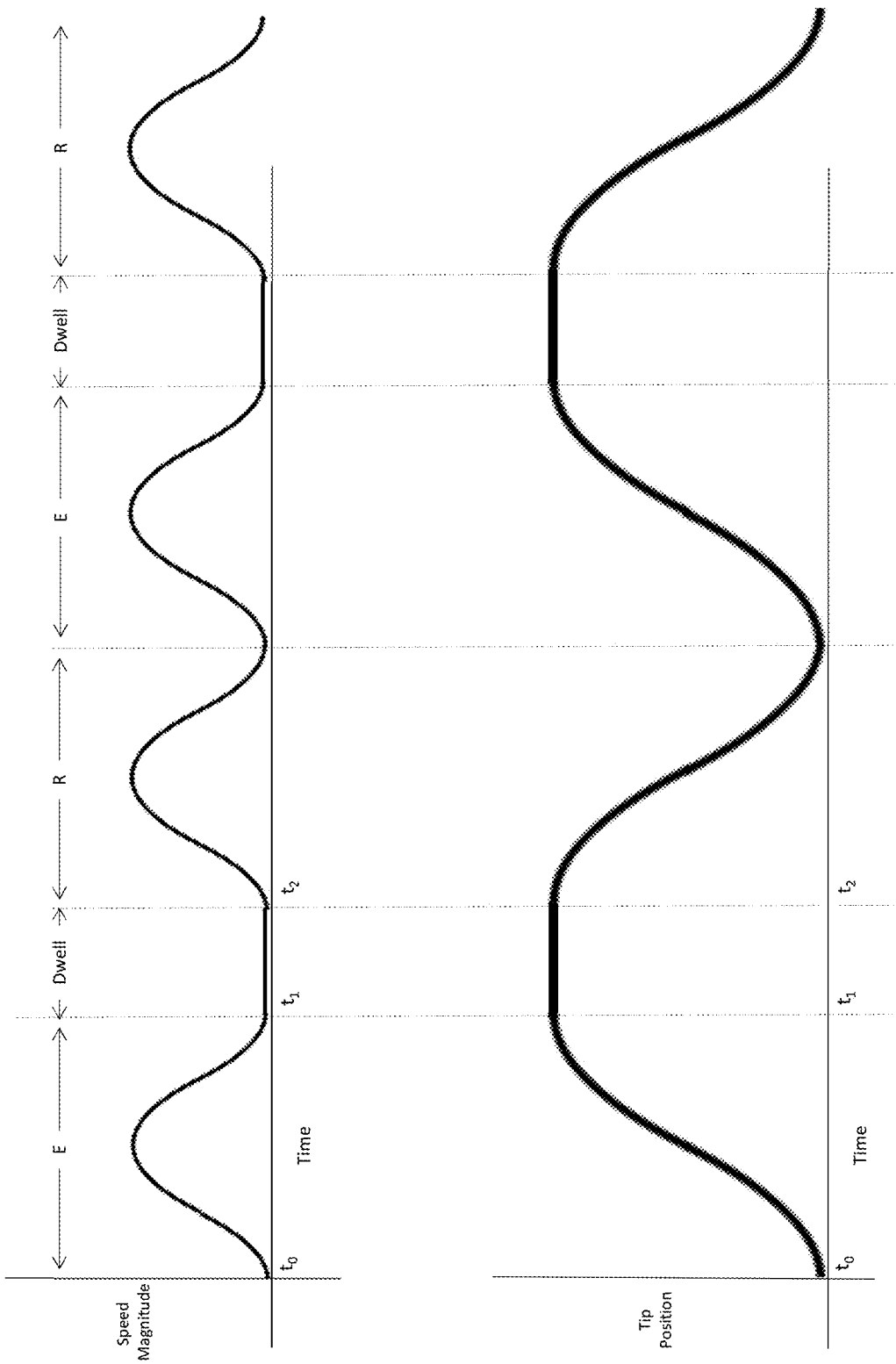
FIG. 30G shows a non-sinusoidal movement of the distal tip of an elongate member (bottom panel) relative to its extension speed profile (top panel).

In conventional phacoemulsification, the speed profile and movement profile of the movable elongate member are generally sinusoidal. Meaning, the movement of the distal tip of the elongate member oscillates in a sine wave pattern, for example, corresponding to a supplied voltage to the piezoelectric crystal. The speed of the distal tip therefore also oscillates in a sinusoidal manner as the derivative of the movement profile. FIG. 30G shows an implementation of non-sinusoidal movement of the distal tip of an elongate member (bottom panel) relative to its extension and retraction speed profiles (top panel). Both the speed profiles and the corresponding movement profiles are shown as being non-sinusoidal. The distal tip can have a dwell time between the extension and retraction cycles. Between $t_0$ and $t_1$, the distal tip can extend forward with a speed profile that may be a sine wave or any other profile. At $t_1$, the distal tip can pause for a dwell period between $t_1$ and $t_2$. The dwell period can be about 0.050 milliseconds, or between about 0.001 and 0.025 milliseconds. At $t_2$, the distal tip can retract with a speed profile that may also follow a sine curve. The movement of the distal tip resembles a sine wave having a dwell at its most extended position.

The non-sinusoidal patterns, for example as shown in FIG. 30G, can reduce the likelihood of cavitation because the dwell time allows for the fluid in the eye that is displaced by movement of the elongate member during extension to return to a zero momentum state before retraction of the elongate member begins. During conventional sinusoidal patterns, the elongate member pushes the fluid away from the distal tip and then retracts immediately while the fluid may still be traveling away from the distal tip thereby increasing the likelihood of cavitation due to the relative velocity of the fluid to the distal tip. The relative velocity of the fluid to the distal tip is higher if the fluid of the eye is being carried away from the tip by momentum while the distal tip itself begins retracting. The dwell period can allow the fluid being displaced to return towards a zero momentum or zero velocity state before the distal tip begins to retract. In this implementation, the extension speed profile and the retraction speed profile may be similar or identical, but the overall speed profile and movement of the distal tip is non-sinusoidal. Other implementations are contemplated herein. For example, the elongate member can slow down more gradually as it approaches its fully extended position than a typically sine wave pattern would. As the elongate member retracts, the profile would follow a more symmetric path. Any number of other non-sinusoidal patterns are considered.

It should be appreciated that the term "non-sinusoidal" as used herein can be defined as a movement or speed profile that does not follow a simple sine wave pattern of oscillating movement. A simple sine wave may be defined by a single frequency, a single phase shift, and a single amplitude. Certain complex profiles may be generated by adding or subtracting sine waves. However, these complex profiles may also be considered non-sinusoidal because their addition or subtraction does not follow a simple sine wave pattern.

The drive mechanism is capable of retracting the elongate member in a proximal direction with a retraction speed profile and advancing the elongate member in a distal direction with an extension speed profile such that the retraction speed profile is different from the extension speed profile. The average retraction speed of the elongate member from the retraction speed profile can be lower than the average extension speed of the elongate member from the extension speed profile. Thus, the drive mechanism operatively coupled to the elongate member is configured to asymmetrically oscillate the elongate member. The extension speed profile E can include a $V_{maxE}$ and the retraction speed profile R can include a $V_{maxR}$ where the $V_{maxR}$ is less than the $V_{maxE}$. The $V_{maxR}$ of the elongate member is generally kept below a threshold speed at which cavitation bubbles would be generated in the eye. Without limiting this disclosure to any particular threshold speed, one of skill in the art would understand the theoretical speed of retraction at which cavitation bubbles may be generated is generally about 5 meters/second. As such, the $V_{maxR}$ of the elongate member may be maintained below about 5 meters/second.

The oscillating movements of elongate members driven by conventional phacoemulsification systems may have a degree of variability due to normal losses during movement (e.g. due to friction or other environmental factors). This variability may impact the average speeds achieved during retraction and extension such that the retraction speed profile and extension speed profile are not identical or perfectly sinusoidal. However, this normal variability during movements of component parts is not intentionally engineered or designed to occur (i.e. a control processor operating according to program instructions stored in a memory; or hardware in operable communication with the control processor designed to achieve different speeds depending on phase of cycling). Thus, normal variability in speed during movement is not considered to be contributing to or resulting in an asymmetric motion profile. The asymmetric motion profiles described herein are consciously engineered or designed motion profiles intended to be substantially reproducible during each cycling and not merely due to chance variability.

Figure 31A:
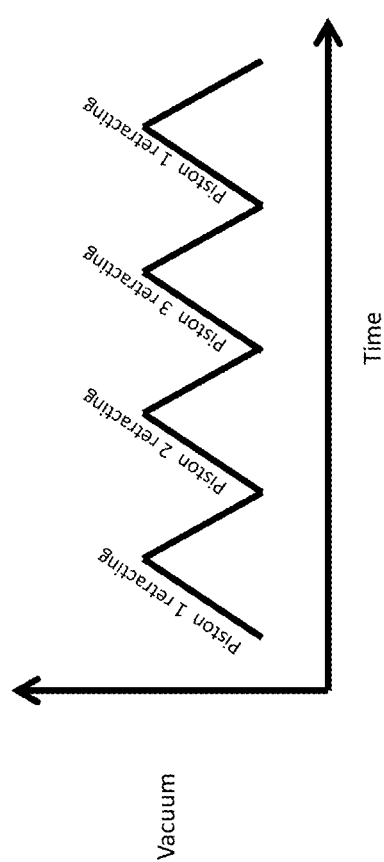
FIG. 31A shows an implementation of a vacuum profile.
Figure 31B:
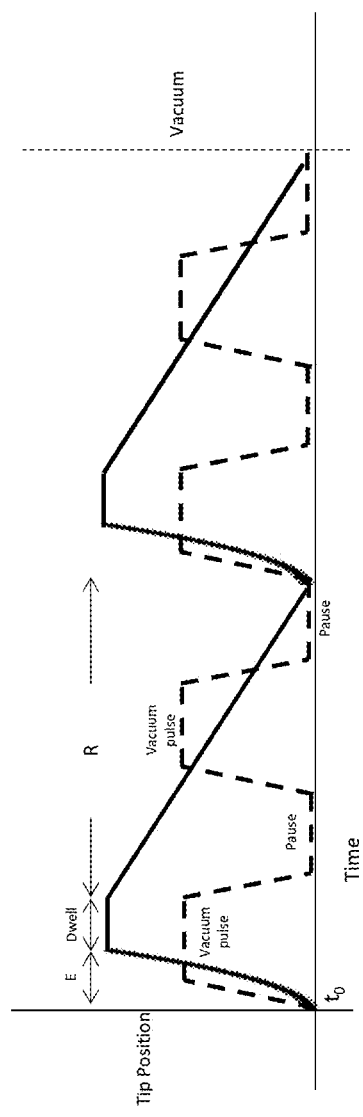
FIGS. 31B-31C show overlap between an asymmetric, non-sinusoidal motion profile for an elongate member (solid line) and a vacuum profile for aspiration through the elongate member (hatched line).
Figure 31C:
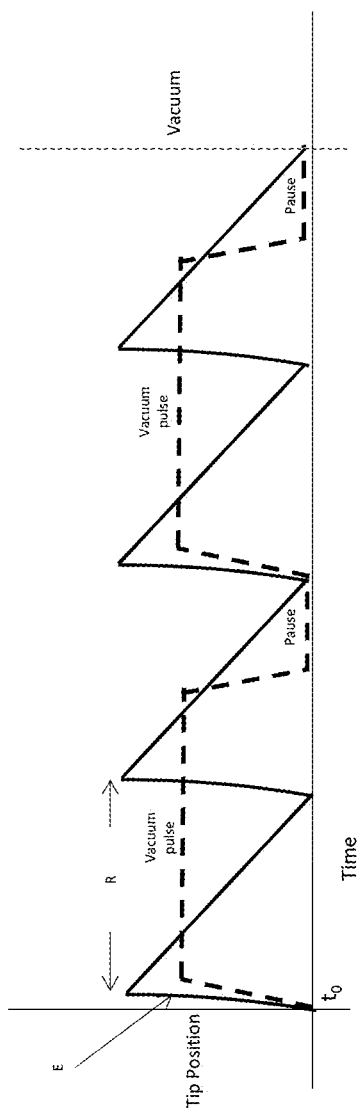

As described elsewhere herein, the vacuum source of the device can be configured to provide pulses of discontinuous negative pressure. A pulse of aspiration can be drawn through the lumen of the elongate member during at least a portion of the extension as the elongate member moves in a distal direction and/or during at least a portion of the retraction as the elongate member moves in a proximal direction. FIG. 31A illustrates an implementation of a vacuum profile over time for the pulsatile vacuum applied through the distal end region of the lumen of the elongate member. As described elsewhere herein, the vacuum source can include a pump having a plurality of pistons configured to move sequentially within their respective pumping chambers creating periods of increasing vacuum interspersed by periods of decreasing vacuum. In some implementations, the increase in vacuum can occur faster than the decrease in the vacuum providing a vacuum profile. The pulsatile vacuum profile applied through the lumen of the distal shaft can be synchronized with the motion profile of the elongate member performing the cutting such that at least a part of the period of negative pressure is applied during a certain phase of movement. FIGS. 31B-31C show the movement of the elongate member (solid lines) relative to the periods of negative pressure (hatched lines) applied through the elongate member. The period of negative pressure (i.e. vacuum pulse) can occur during at least part of the forward stroke or distal extension E of the elongate member, dwell time after distal extension E and before proximal retraction R, and/or during at least part of the proximal retraction R of the elongate member. For example, FIG. 31B shows a first pulse of vacuum pressure occurs during the extension E of the elongate member as well as the dwell time after extension E and before retraction R. The first pulse of vacuum pressure ends during the retraction R phase and a second pulse of vacuum begins and ends before the same retraction phase ends. FIG. 31C shows another implementation where a first pulse of vacuum pressure begins during extension E of the elongate member and is maintained during retraction R phase of the elongate member as well as during a second extension E of the elongate member. FIG. 31B shows the vacuum pulse having about 2× the frequency of tip movement and FIG. 31C shows the tip movement having about 2× the frequency of the vacuum pulse. Both FIG. 31B and FIG. 31C show vacuum pulse occurring during a portion of the extension E and retraction R. It should be appreciated that any number of various relative frequencies are considered herein and that these are illustrations of some examples of the relative speed profiles and vacuum profiles.

The displacement or travel distance of the tip 2965 can vary, but is generally greater than phacoemulsification tips known in the art. Typical phacoemulsification tips have a tip displacement of on the order of about 0.1 mm and move at a frequency of between about 20-40 kHz. The tips 2965 described herein can have a greater displacement distance and a lower frequency. For example, the displacement achieved by the tip 2965 can be between about 0.05 mm-1.0 mm at a frequency of about 10-2,000 Hz. In this way, the devices described herein may not be ultrasonic and may not generate the heat associated with harmful effects in the eye during cataract surgery. In some implementations, the tip 2965 is pushed forward by a spring 2935. A longer stroke distance can allow for the tip to achieve a higher final speed $V_{maxE}$ at the time of impact with eye tissue.

Figure 29H:
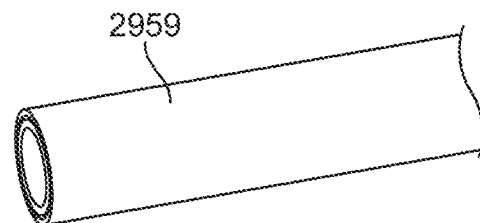

In some implementations, the device 2900 can have an outer tube 2959 that extends over an elongate member 2955 (see FIGS. 29G-29H). Relative lengths of the inner and outer members 2955, 2959 can be such that a distal tip 2965 of the elongate member 2955 extends beyond a distal end of the outer member 2959 when it is fully extended in a distal direction forming a fully extended configuration. The distal tip of the elongate member 2955 in the fully extended configuration is positioned distal of a distal opening of the outer member 2959. A distance between the distal opening of the outer member 2959 and the distal tip of the elongate member 2955 in the fully extended configuration defines an extension distance D. The elongate member 2955 fully retracts into the outer member 2959 when it is in a fully retracted position. The distance the distal tip of the elongate member 2955 moves relative to the outer member 2959 from the fully retracted configuration to the fully extended configuration defines a travel distance. The extension distance can be less than the travel distance, for example, half the travel distance. In some configurations the travel distance is between about 0.05 mm to about 1.0 mm and the extension distance is between about 0.1 mm to about 0.5 mm. Therefore, the distal tip 2965 of the elongate member 2955 can be only exposed to the lens material for a portion of its motion profile. For example, the elongate member 2955 may extend forward about 0.5 mm from its fully retracted position and approximately half of this stroke may be within the outer member 2959 such that only the last 0.25 mm of the stroke the elongate member 2955 extends beyond the outer member 2959. In this way, the elongate member 2955 can accelerate to a high speed before it impacts the lens material. Retraction of the elongate member 2955 fully into the outer member 2959 provides a further benefit in that it may help separate lens material from the distal tip 2965 of the elongate member 2955 as it retracts into the outer member 2959 preventing the lens material from 'lollipopping' onto the distal tip 2965 of the elongate member 2955.

The drive mechanism operatively coupled to the elongate member 2955 configured to cause oscillating movements of the elongate member 2955 can vary as described elsewhere herein. In some implementations, the elongate member 2955 can be driven by a drive mechanism incorporating a spring element 2935. However, other energy modalities are considered herein for driving the elongate member 2955 in the asymmetric or non-sinusoidal manner discussed herein. For example, the elongate member 2955 can be driven mechanically, hydraulically, pneumatically, electromagnetically, or via a piezoelectric drive system as described below. One of skill in the art would understand the structures necessary to implement various drive mechanisms so as to move the elongate member as described herein.

In some implementations, the drive mechanism of the device can incorporate a piezoelectric element configured to drive the elongate member, such as by driving the hub 2987 forward and backward. The piezoelectric element can respond to changes in voltage by decreasing or increasing in size. A high frequency voltage connected to the piezoelectric element can generate a motion profile of the tip 2965 that matches the frequency of the supplied voltage. The voltage signals sent to the piezoelectric element can be generally non-sinusoidal in shape and therefore the tip 2965 moves in a generally non-sinusoidal pattern as described elsewhere herein. The voltage may have a waveform that contracts the piezoelectric elements slower than it allows them to expand. This moves the tip 2965 slower on the retraction stroke than on the extension stroke. Any number of motion profiles may be commanded based on the voltage waveform supplied to the piezoelectric element. For example, two or more overlapping voltage sinusoidal waveforms can be supplied to the piezoelectric element that creates an interference effect such that a non-sinusoidal wave form is created.

In still further implementations, a combination of mechanisms and modalities are incorporated in the device to drive the elongate member with a non-sinusoidal motion profile. For example, an electromagnetic coil can be configured to move a ferritic core forward with the application of a current through the coil. The core can be configured to be driven forward by the electromagnetic coil, but then retract backwards (i.e. proximally) through the force of a compressed spring. Therefore, with an increase in current through the coil, the core is driven forward. With the current is reduced, the core retracts backward. In this manner, the core may be connected to a cutter member so that the extension forward can be executed quickly by the sudden increase in current in the coil, but the retraction may be slower by the force of the compressed spring.

The devices described herein can be actuated using one or more inputs including a trigger, button, slider, dial, keypad, switch, touchscreen, foot pedal, or other input that can be retracted, pressed, squeezed, slid, tapped, or otherwise actuated to activate, modify, or otherwise cause the oscillation, aspiration, and/or infusion of fluid through the elongate member. The actuators can be incorporated into the device itself or can be remote from the device, but in wired or wireless communication with the device such as on an external computing device having its own inputs. As described elsewhere herein, the device the one or more inputs can be urged by a user into a position that causes the drive mechanism to increase the frequency of oscillation of the elongate member the more the trigger is actuated (e.g. by increasing the spinning of a motor).

The devices described herein can also be programmed to provide limits on a particular action upon actuation of the input. For example, the drive mechanism can be programmed to have a minimum and/or maximum speed upon actuation of the input or, in the case of fluid infusion and aspiration, the device can be programmed to have a minimum and/or maximum fluid pressure upon actuation of an input. Thus, the devices described herein can be programmed using inputs adjustable by a user as well as by pre-programmed instructions that impact the one or more aspects of the device upon actuation of the inputs.

The devices described herein can include a controller in operative communication with one or more components of the drive mechanism, the vacuum source, or other components of the device including an external computing device. The controller can include at least one processor and a memory device. The memory can be configured for receiving and storing user input data. The memory can be any type of memory capable of storing data and communication that data to one or more other components of the device, such as the processor. The memory may be one or more of a Flash memory, SRAM, ROM, DRAM, RAM, EPROM, dynamic storage, and the like. The memory can be configured to store one or more user-defined profiles relating to the intended use of the device. The memory can be configured to store user information, history of use, measurements made, and the like.

The devices described herein can include a communication module in operative communication with one or more components of the device, such as the controller. The communication module can communicate with an external computing device having a communication module. The connection between the communication module of the device and the external computing device can include a wired communication port such as a RS22 connection, USB, Firewire connections, proprietary connections, or any other suitable type of hard-wired connection configured to receive and/or send information to the external computing device. The communication module can also include a wireless communication port such that information can be fed between the device and the external computing device via a wireless link, for example, to display information in real-time on the external computing device about operation of the device, and/or control programming of the device. For example, a user can program the speed profile of the motor 2756 of the device on the external computing device. Any of a variety of adjustments to and programming of the device can be performed using the external computing device. The wireless connection can use any suitable wireless system, such as Bluetooth, Wi-Fi, radio frequency, ZigBee communication protocols, infrared, or cellular phone systems, and can also employ coding or authentication to verify the origin of the information received. The wireless connection can also be any of a variety of proprietary wireless connection protocols. The external computing device with which the device communicates can vary including, but not limited to, desktop computer, laptop computer, tablet computer, smartphone, or other device capable of communicating and receiving user input.

The processor, memory, storage devices, input/output devices can be interconnected via a system bus. The processor can be capable of processing instructions for execution within the system. Such executed instructions can implement one or more of the processes described herein related to the use of the device. The processor of the controller can be a single-threaded processor or a multi-threaded processor. The processor of the controller can be capable of processing instructions stored in the memory and/or on a storage device to provide an output of information to the user about operation of the device.

One or more aspects of the device can be programmed by a user. For example, one or more aspects of the drive mechanism can be programmed by a user to control the motion of the elongate member including, but not limited to travel distance of the elongate member, frequency of oscillation of the elongate member, maximum extension speed ($V_{maxE}$), minimum extension speed ($V_{minE}$), maximum retraction speed ($V_{maxR}$), minimum retraction speed ($V_{minR}$), average extension speed ($V_{avgE}$), average retraction speed ($V_{avgR}$), or any other aspect of the motion profile. In some implementations, the distance the elongate member moves with each cycle can be adjustably programmed such that the amplitude of its oscillation is selectable within a range of about 0.5 Hz to about 5000 Hz, or in a range of about 10 Hz to about 2000 Hz. The amplitude of oscillation can be less than ultrasonic, for example, less than about 20,000 Hz or within the ultrasonic range (e.g. about 20,000 Hz, to about 120,000 Hz, up to the gigahertz range).

One of more aspects of the vacuum source can also be programmed by a user to control the vacuum applied at the distal end region of the elongate member including, but not limited to flow rate of aspiration, minimum vacuum pressure, maximum vacuum pressure, frequency of vacuum pulses, or any other aspect of the vacuum profile. In some implementations, the flow rate of aspiration can be adjustably programmed within a range of between about 5-100 ml/min.

The devices described herein can be used such that one or more aspects are manually controlled and/or adjusted according to manual inputs by the user. The devices described herein can be programmed to control the one or more aspects. The controller can include software capable of being programmed to adjust or provide limits on the one or more aspects of the device. Thus, the software run by the controller can provide certain aspects of the device without any user input during use. In an implementation, the adjustments or programming can be via a controller that is controlled by software, either within the device or on an external computer device. A user can program the controller remotely via an external computing device in communication with the device via a wireless connection such as BlueTooth.

It should also be appreciated that the asymmetric motion profile with or without the vacuum pulse described herein can be applied to known phacoemulsification systems typically used for cataract surgery and vitrectomy. Conventional phacoemulsification systems configured to move an elongate member at ultrasonic frequency to remove lens material can implement the one or more motion profiles and/or vacuum profiles as described herein via software or hardware, for example by circuits providing a certain voltage causing the asymmetric movements. Thus, the asymmetric motion profiles and pulsed vacuum profiles described herein can be applied to a machine configured to oscillate at ultrasonic frequencies.

Aspects of the subject matter described herein may be realized in digital electronic circuitry, integrated circuitry, specially designed ASICs (application specific integrated circuits), computer hardware, firmware, software, and/or combinations thereof. These various implementations may include an implementation in one or more computer programs that are executable and/or interpretable on a programmable system including at least one programmable processor, which may be special or general purpose, coupled to receive signals, data and instructions from, and to transmit signals, data, and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of an anchoring delivery system to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A medical device for removing lens tissue from inside a capsular bag of an eye, the device comprising:
    a cam assembly operatively coupled to at least one vacuum generation source, at least a first portion of the cam assembly capable of rotating about an axis to cause the at least one vacuum generation source to generate vacuum; and
    an elongate member operatively coupled to the cam assembly, at least a distal portion of the elongate member positioned distally of the cam assembly, and wherein at least a second portion of the cam assembly is capable of rotating about the axis to cause the elongate member to oscillate.

2. The medical device of claim 1, wherein the causing the elongate member to oscillate comprises causing the elongate member to reciprocate along a longitudinal axis of the elongate member.

3. The medical device of claim 2, wherein the elongate member reciprocates in a distal direction with a first maximum speed, and reciprocates in a proximal direction with a second maximum speed, wherein the first maximum speed is greater than the second maximum speed.

4. The medical device of claim 2, wherein the longitudinal axis of the elongate member is coincident with the axis about which the cam assembly rotates.

5. The medical device of claim 1, wherein the first portion of the cam assembly comprises a first surface, the at least one vacuum generation source comprises a piston and a cylinder, and wherein rotation of the first surface causes the piston to reciprocate within the cylinder to generate vacuum.

6. The medical device of claim 1, wherein the second portion of the cam assembly comprises a second surface, wherein a proximal portion of the elongate member is coupled to a third portion of the cam assembly comprising a third surface, and wherein the second surface rotating over the third surface causes the elongate member to oscillate.

7. The medical device of claim 1, wherein the at least one vacuum generation source comprises a plurality of vacuum generation sources, and the rotation of the first portion of the cam assembly causes each of the plurality of vacuum generation sources to generate vacuum.

8. The medical device of claim 1, wherein the cam assembly is operatively rotated by a motor positioned within an interior of a housing containing the cam assembly.

9. The medical device of claim 1, further comprising a housing, wherein the housing comprises the cam assembly, the at least one vacuum generation source, the elongate member and a motor for rotating the first and second portions of the cam assembly.

10. The medical device of claim 9, wherein a speed of the motor is variably controlled by an input on the housing.

11. The medical device of claim 1, wherein rotation of the first and second portions of the cam assembly causes generation of a plurality of pulses of vacuum synchronized with a plurality of oscillations of the elongate member.

12. The medical device of claim 11, wherein the plurality of oscillations of the elongate member generated has a greater frequency than the plurality of pulses of vacuum generated.

13. The medical device of claim 11, wherein the plurality of pulses of vacuum generated has a greater frequency than the plurality of oscillations of the elongate member generated.

14. The medical device of claim 1, wherein the cam assembly is configured to generate a period of vacuum during at least a portion of a distal stroke of the elongate member or at least a portion of a proximal stroke of the elongate member.

15. The medical device of claim 1, wherein the cam assembly is configured to generate a period of vacuum during at least a portion of a distal stroke of the elongate member and at least a portion of a proximal stroke of the elongate member.

16. The medical device of claim 1, wherein the cam assembly is configured to generate a period of vacuum during at least a first extension and a first retraction of the elongate member and at least a second extension of the elongate member.

17. The medical device of claim 1, wherein the elongate member undergoes a dwell time of no movement after a distal stroke and before a proximal stroke.

18. The medical device of claim 17, wherein a first period of vacuum occurs during the distal stroke and during the dwell time.

19. The medical device of claim 18, wherein the first period of vacuum is maintained during at least a second distal stroke and at least a second proximal stroke of the elongate member.

* * * * *